US010995217B2

(12) United States Patent
Falber

(10) Patent No.: US 10,995,217 B2
(45) Date of Patent: May 4, 2021

(54) COMPOUNDS AS POTENTIAL DYE MOLECULES

(71) Applicant: LLEAF PTY LTD, New South Wales (AU)

(72) Inventor: Alexander Falber, Valley Village, CA (US)

(73) Assignee: LLEAF PTY LTD, Strathfield (AU)

( * ) Notice: Subject to any disclaimer, the term of this patent is extended or adjusted under 35 U.S.C. 154(b) by 0 days.

(21) Appl. No.: 16/637,024

(22) PCT Filed: Aug. 8, 2018

(86) PCT No.: PCT/AU2018/050828
§ 371 (c)(1),
(2) Date: Feb. 6, 2020

(87) PCT Pub. No.: WO2019/028508
PCT Pub. Date: Feb. 14, 2019

(65) Prior Publication Data
US 2020/0199367 A1   Jun. 25, 2020

(30) Foreign Application Priority Data

Aug. 8, 2017   (AU) ................................ 2017903150

(51) Int. Cl.
*C07D 471/22* (2006.01)
*C09B 5/62* (2006.01)

(52) U.S. Cl.
CPC .............. *C09B 5/62* (2013.01); *C07D 471/22* (2013.01)

(58) Field of Classification Search
CPC ................................ C07D 471/22; C09B 5/62
USPC .................... 546/29, 27; 106/31.27
See application file for complete search history.

(56) References Cited

U.S. PATENT DOCUMENTS 7,910,736 B2 * 3/2011 Koenemann ......... C07D 471/06
257/27
2007/0259475 A1   11/2007 Konemann et al.

FOREIGN PATENT DOCUMENTS

| EP | 2824138 | | 8/2017 | |
| JP | 2002038044 A | * | 2/2002 | ............. C09B 48/00 |
| KR | 2017066951 A | * | 6/2017 | ............... C09B 5/30 |
| WO | WO 2014/010305 A1 | | 1/2014 | |

OTHER PUBLICATIONS

Oh, S.H., et al., "The synthesis of symmetric and asymmetric perylene derivatives and their optical properties", Dyes and Pigments, vol. 85, No. 1-2, Oct. 13, 2009 (Oct. 13, 2009), pp. 37-42.
Debije, M. G., et al.: "Promising fluorescent dye for solar energy conversion based on a perylene perinone", Applied Optics, vol. 50, No. 2, Jan. 10, 2011 (Jan. 10, 2011), pp. 163-169.
International Search Report and Written Opinion in related PCT Application No. PCT/AU2018/050828, dated Sep. 18, 2018 (8 pages).
Yuan et al. (2009) "Efficient synthesis of regioisomerically pure bis (trifluoromethyl)-substituted 3, 4, 9, 10-perylene tetracarboxylic bis (benzimidazole)", Organic Letters, 2009, 11(13), pp. 2808-2811.

* cited by examiner

*Primary Examiner* — Charanjit Aulakh
(74) *Attorney, Agent, or Firm* — Lathrop GPM LLP; Brian C. Trinque

(57) ABSTRACT

Disclosed herein are a series of compounds based on Formula (I). These compounds comprise perylene core which has been extended with optionally functionalised imidazoles at the 3,4;9,10 positions. The compounds of Formula (I) can be functionalised at two positions on the perylene core, such as the 1,6 or 1,7 positions. Also disclosed herein are compositions comprising said compounds, methods of forming said compounds and potential applications of said compounds, such as applying the compounds as a dye whose absorbance and fluorescence spectrum are red-shifted.

20 Claims, 15 Drawing Sheets

R = alkyl, heterocycle or aryl

COMPOUNDS AS POTENTIAL DYE MOLECULES

CROSS-REFERENCE TO RELATED APPLICATIONS

The present application claims priority from Australian Provisional Patent Application No 2017903150 filed on 8 Aug. 2017, the content of which is incorporated herein by reference.

TECHNICAL FIELD

Disclosed herein are a series of perylene based compounds which may be dye molecules, with tailored absorbance and emission spectral maxima.

BACKGROUND

Red light absorbing and near-IR absorbing perylene dyes are useful in a range of applications, including in vat dyes[1-4] and organic solar cells.[5-9]

Perylene 3,4,9,10 tetracarboxylic dianhydride (FIG. 1) is a useful precursor to generate numerous perylenes dyes. For example, a primary amine may be reacted with the anhydride group to form the corresponding perylenes diimide (FIG. 2).

To achieve a red shifted perylene absorbance, numerous synthetic techniques can be applied, one of which is to expand the conjugated pi system of the perylene molecule at the 3,4 and/or 9,10 positions to generate an aryl imidazole group (for example, a benzimidazole, naphthyl imidazole or phenanthracyl imidazole). This may be accomplished by condensation of an o-aryl diamine with a perylene bearing a carboxylic anhydride group on one or both of the 3,4 or 9,10 positions Another technique that is used to both further red shift aryl imidazole appended perylenes and greatly increase solubility is to substitute the 1,6,7 and 12 positions (also known as the "bay" positions) of the perylene with chlorides. The resulting tetrachloro-pereylene can form tetraphenoxy perylenes by reaction with a phenol. A variety of functionalised tetraphenoxy perylenes have been previously synthesised.[10-12] It has been shown that appending aryl imidazoles groups on tetraphenoxy perylenes generates red shifted, soluble dyes. FIG. 3 highlights the possible condensation of 1,6,7,12-tetraphenoxy-3,4:9,10-perylenetetracarboxydianhydride with a range of aryl o-diamines. In this Figure, "R" may be a straight chain alkyl group. The resulting imidazole appended perylenes products may be used as dyes.

In all cases where the combined aryl imidazole and phenoxy chemistry is applied, the tetraphenoxy perylene core is utilised to achieve red shifted molecules. The actual production of these dyes may begin with condensation of the tetra halogenated core (e.g., 1,6,7, 12-tetrachloro-3,4;9,10-perylenetetracarboxydianhydride) and perform the phenoxy substitution reaction as a second step.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Herein, the inventors have taken a different approach to provide perylene dyes with an extended aryl imidazoles at the 3,4;9,10 positions. Disclosed herein are compounds functionalised at 2 bay positions, for example the 1,6 or 1,7 positions. Compounds obtained accordingly, may be used as a dye whose absorbance and fluorescence spectrum are red-shifted.

Disclosed herein are a series of compounds based on the generation of an extended aryl imidazole structure on a 1,6 or 1,7 di-substituted perylene core to achieve a series of perylene molecules that may display unique spectroscopic properties (namely absorption and fluorescence maxima) compared to the analogous tetra substituted perylenes bearing the same aryl imidazole groups, thus forming a different series of perylenes dyes.

In a first aspect, provided herein is a compound of Formula (I):

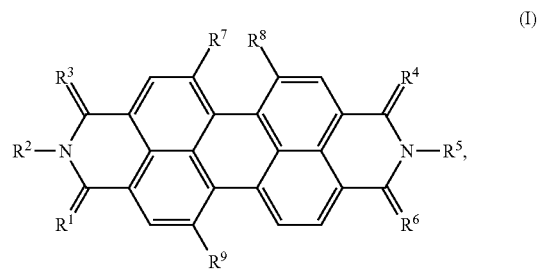

or an isomer or salt thereof, wherein:

for $R^1$, $R^2$ and $R^3$ either:

(i) $R^1$ is O, $R^3$ is N, and $R^2$ and $R^3$ are joined by a

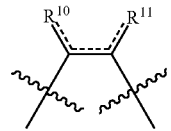

group; or (ii) $R^3$ is O, $R^1$ is N, and $R^1$ and $R^2$ are joined by a

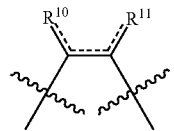

group;

for $R^4$, $R^5$ and $R^6$ either:

(i) $R^4$ is O, $R^6$ is N, and $R^5$ and $R^6$ are joined by a

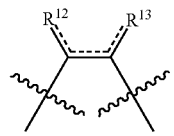

group; or (ii) $R^6$ is O, $R^4$ is N, and $R^4$ and $R^5$ are joined by a

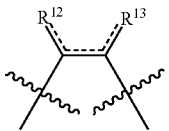

group;

$R^{10}$ and $R^{11}$:
- (i) are joined to form an optionally substituted monocyclic aromatic ring; or
- (ii) are joined to form an optionally substituted polycyclic aromatic group;

$R^{12}$ and $R^{13}$:
- (i) are joined to form an optionally substituted monocyclic aromatic ring; or
- (ii) are joined to form an optionally substituted polycyclic aromatic group;

each of $R^7$, $R^8$ and $R^9$ is either:

independently selected from hydrogen or

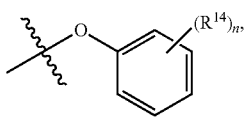

with the proviso that two of $R^7$, $R^8$ and $R^9$ are

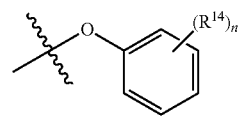

and the other is hydrogen; or independently selected from: hydrogen, bromine, or chlorine, with the proviso that two of $R^7$, $R^8$ and $R^9$ are either bromine or chlorine, and the other is hydrogen;

each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, each of which optionally comprises one or more substituents;

===== represents the presence of a single or double bond; and n is an integer selected from 0, 1, 2, 3, 4 or 5.

In a second aspect, provided herein is a dye composition comprising a compound according to the first aspect.

In a third aspect, provided herein is a method of synthesising a compound according to the first aspect, the method comprising the step of contacting a compound of Formula (II)

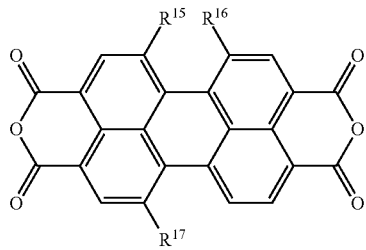

Formula (II)

wherein each of $R^{15}$, $R^{16}$ and $R^{17}$ is independently selected from hydrogen, bromine or chlorine, with the proviso that two of $R^{15}$, $R^{16}$ and $R^{17}$ are either bromine or chlorine, and the other is hydrogen, with a compound of Formula (III):

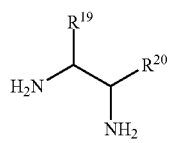

Formula (III)

wherein $R^{19}$ and $R^{20}$: are joined to form an optionally substituted monocyclic aromatic ring; or are joined to form an optionally substituted polycyclic aromatic group.

In a fourth aspect, provided herein is a compound produced by a method according to the third aspect.

In a fifth aspect, provided herein is use of a compound according to the first aspect or the fourth aspect as a dye.

The advantages of the disclosed series of perylenes dyes may include, but are not limited to:

1. The generation of a series of red shifted dyes derived from the 1,6 or 1,7 dibromo perylenes where previously such dyes were limited substituents at the 3,4 9,10 carboxy positions, such as esters or imides, having higher frequency absorbance and luminescence than the aryl imidazole perylenes in the current disclosure. This allows a greater range of potential perylenes products from the dibromo dianhydride starting material.

2. Some dyes of the current disclosure can replace non-perylene and perylenes dyes that are more costly and/or difficult to manufacture for some frequencies ranges. For example a bis phenoxy di benzimidazole perylenes in the current disclosure has a similar absorbance and luminescence spectrum compared to a tetraphenoxy 3,4 mono imide 9, 10 mono benzimidazole perylenes, the latter being much more difficult to manufacture having different substituents on the carboxy positions.

3. The higher reactivity of the dibromo perylenes of the current disclosure, towards substitution by nucleophiles as well as the lower stearic hindrance around the bay positions by having 2 instead of 4 substituents at the bay positions, compared to tetra chloride perylenes, allows for the generation of larger multi-chromophore complexes having a red shifted core. For example two phenol bearing perylenes having a high frequency absorption can be appended to a dibromo diaryl imidazole core to form a trimeric light harvesting array, having a perylene of the current disclosure acting as the lowest absorbing acceptor molecule. Previously reported bay appended arrays formed using a dibromo perylenes core have been limited to the imide or ester bearing core perylenes.

DESCRIPTION OF EMBODIMENTS

Definitions

Figure 1:
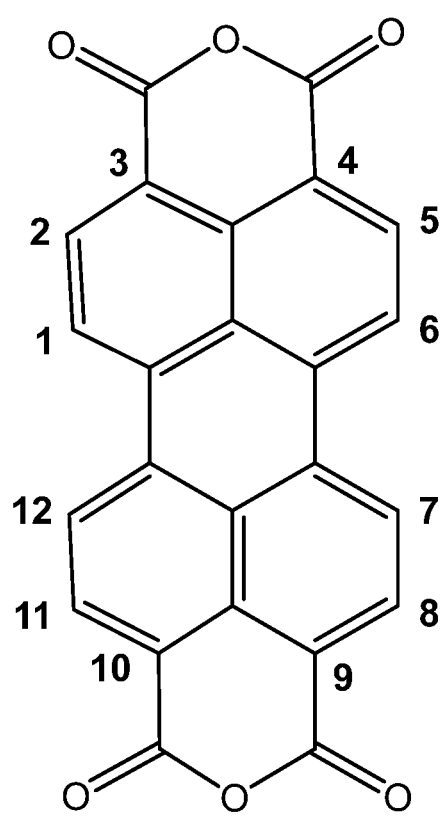
FIG. 1—Perylene 3, 4 9,10 tetracarboxylic dianhydride.
Figure 2:
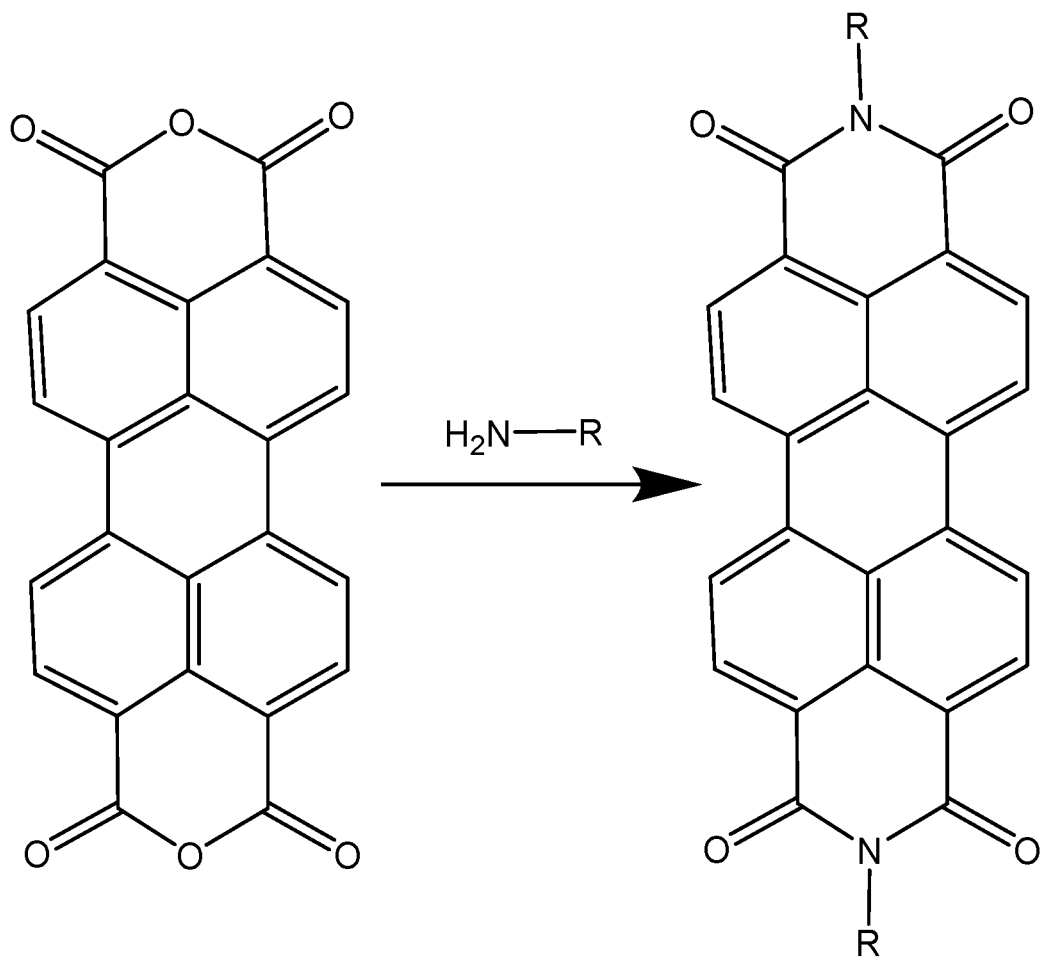
FIG. 2—Synthesis of perylene 3,4,9,10 tetracarboxy diimide.
Figure 3:
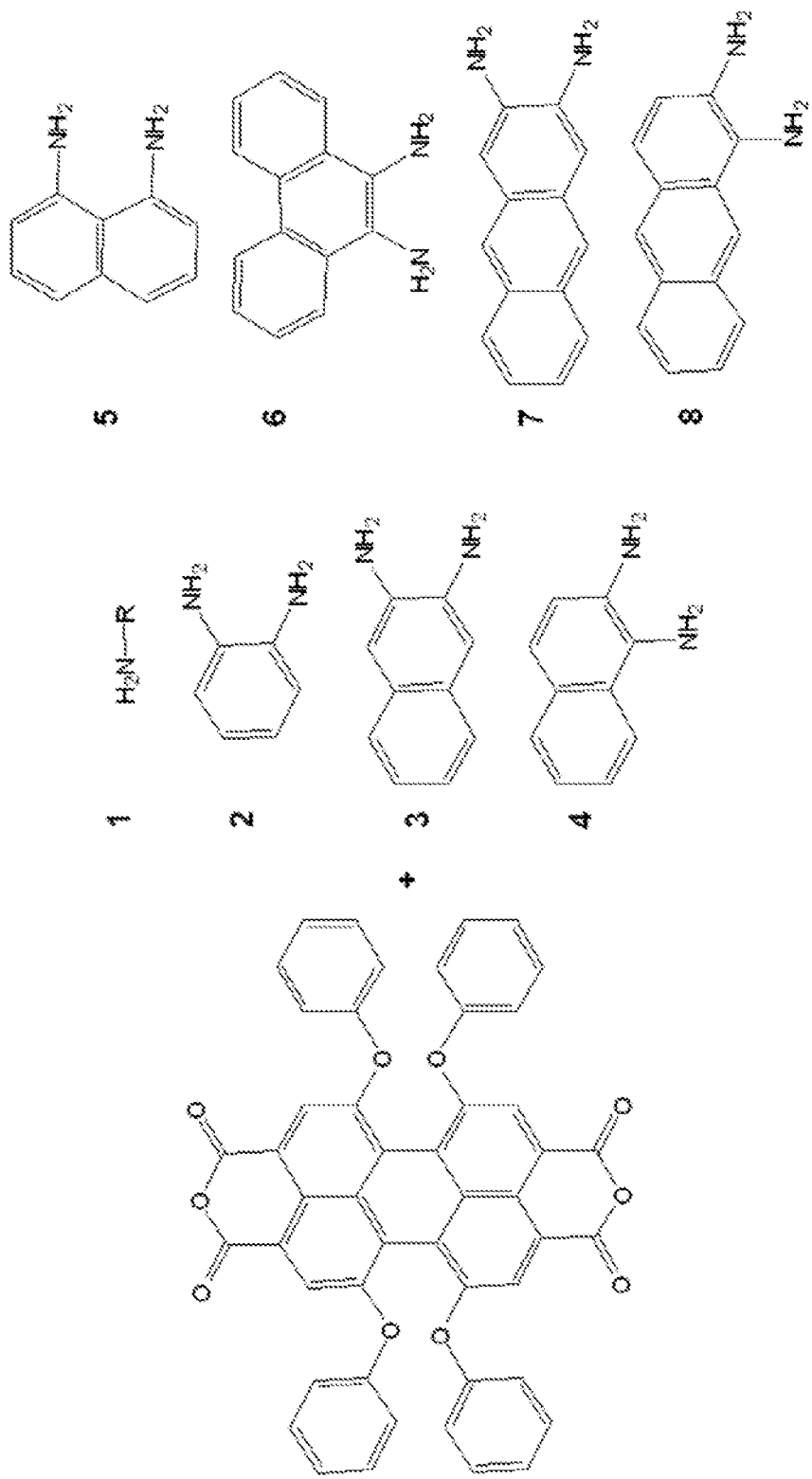
FIG. 3—The possible production of tetraphenoxy compounds based on the reaction of 1,6,7,12-tetraphenoxy-3,4: 9,10-perylenetetracarboxydianhydride with a selection of possible diamines FIG. 4—UV/vis absorbance spectrum for Compound 2.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting essentially of" is intended to exclude elements which would materially affect the properties of the claimed composition.

Throughout the present specification, various aspects and components of the disclosure can be presented in a range format. The range format is included for convenience and should not be interpreted as an inflexible limitation on the scope of the disclosure. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 5, 5.5 and 6, unless where integers are required or implicit from context. This applies regardless of the breadth of the disclosed range. Where specific values are required, these will be indicated in the specification.

Herein the term "about" encompasses a 10% tolerance in any value(s) connected to the term.

In the present specification, the structural formula of a compound may represent a certain isomer for convenience in some cases, but the present disclosure, unless otherwise indicated, includes all isomers, such as geometrical isomers, for example syn- and anti-isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral centre".

"Chiral isomer" means a compound with at least one chiral centre. Compounds with more than one chiral centre may exist either as an individual diastereomer or as a mixture of diastereomers, termed "diastereomeric mixture". When one chiral centre is present, a stereoisomer may be characterized by the absolute configuration (R or S) of that chiral centre. Absolute configuration refers to the arrangement in space of the substituents attached to the chiral centre.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond.

Herein the compounds of Formula (I) may exist in either the "syn" or the "anti" form. For example:

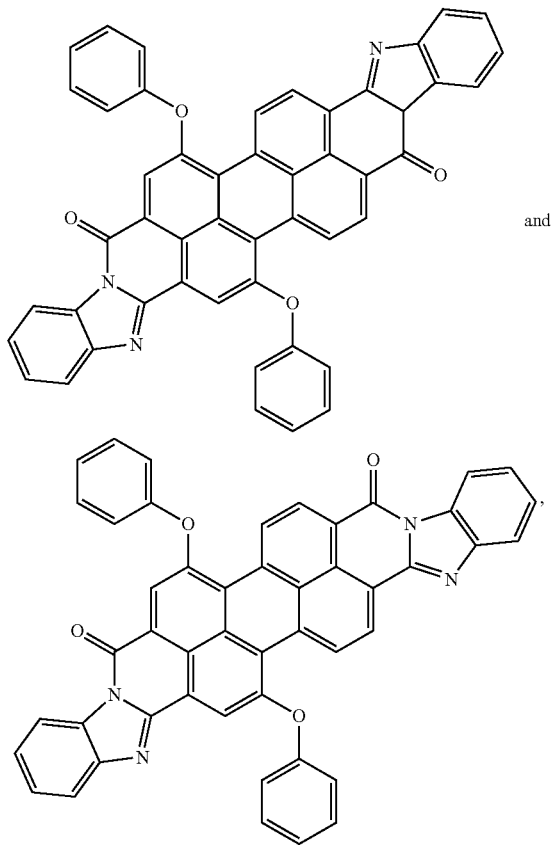

are anti and syn isomers of the same compound, respectively.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerisation is possible, a chemical equilibrium of the tautomers will be reached. The exact ratio of the tautomers depends on several factors, including temperature, solvent and pH. The concept of tautomers that are inter-convertible by tautomerisations is called tautomerism.

"Alkyl" means a straight chain or branched, noncyclic or cyclic, saturated aliphatic hydrocarbon. The alkyl group may contain from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. The alkenyl group may contain from 2 to 24 carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-I-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. The alkynyl group may contain from 2 to 24 carbon atoms. Representative straight chain and branched alkynyls include acetylenyl, propynyl, 1-butynyl, 2-butynyl, 1-pentynyl, 2-pentynyl, 3-methyl-1-butynyl, and the like.

The term "aryl" disclosed herein refers to a mono- or polycyclic aromatic hydrocarbon systems. The aryl systems may have having 3 to 22 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the Formula (1) can be affected via any possible ring member of the aryl radical. Examples of suitable aryl radicals are phenyl, biphenyl, naphthyl, 1-naphthyl, 2-naphthyl and anthracenyl, but likewise indanyl, indenyl or 1,2,3,4-tetrahydronaphthyl.

The term "unsubstituted" means that the corresponding radical, group or moiety has no substituents.

The terms "optionally substituted", "comprises one or more substituents" or "substituted" means that a corresponding radical, atom, group or moiety on a compound may have one or more substituents present. Where a plurality of substituents, or a selection of various substituents is specified, the substituents are selected independently of one another and do not need to be identical. In some case, at least one hydrogen atom on the radical, group or moiety is replaced with a substituent. In the case of an oxo substituent (=O) two hydrogen atoms may be replaced. In this regard, substituents may include: alkyl, alkene, alkyne, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido) alkyl, mercaptoalkyl, (heterocyclo)alkyl, (cycloalkylamino) alkyl, ($C_1$-$C_4$ haloalkoxy)alkyl, (heteroaryl)alkyl, or perylene, oxo, heterocycle, —OR$^x$, —NR$^x$R$^y$, —NR$^x$C (=O)R$^y$ —NR$^x$SO$_2$R$^y$, —C(=O)R$^x$, —C(=O)OR$^x$, —C(=O)NR$^x$R$^y$, —SO$_q$R$^x$ and —SO$_q$NR$^x$R$^y$, wherein q is 0, 1 or 2, R$^x$ and R$^y$ are the same or different and independently selected from hydrogen, alkyl or heterocycle, and each of said alkyl and heterocycle substituents may be further substituted with one or more of oxo, halogen, —OH, —CN, alkyl, —OR$^x$, heterocycle, —NR$^x$R$^y$, —NR$^x$C(=O) R$^y$—NR$^x$SO$_2$R$^y$, —C(=O)R$^x$, —C(=O)OR$^x$, —C(=O) NR$^x$R$^y$, —SOR$^x$ and —SONR$^x$R$^y$.

"Halogen" or "halo" means fluorine, chlorine, bromine and/or iodine groups.

Herein, unless otherwise indicated, in the disclosed compounds ----- represents the presence of a single or double bond, as valency permits.

As used herein and unless otherwise indicated, the term "salt" includes, but is not limited to, a salt of an acidic or basic group that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, methanesulfonate (mesylate), methylsulfate, muscate, napsylate, nitrate, pantothenate, phosphate/diphosphate, polygalacturonate, salicylate, stearate, succinate, sulfate, tannate, tartrate, teoclate, triethiodide, and pamoate. Under certain basic conditions, the compound can form base salts with various acceptable cations. Non-limiting examples of such salts include alkali metal or alkaline earth metal salts and, particularly, calcium, magnesium, sodium, lithium, zinc, potassium and iron salts.

Formula (I)

Disclosed herein are compounds of Formula (I):

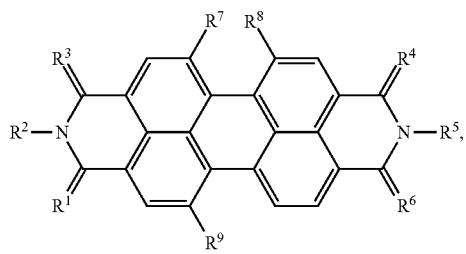

(I)

or an isomer or salt thereof, wherein:
for $R^1$, $R^2$ and $R^3$ either:
(i) $R^1$ is O, $R^3$ is N, and $R^2$ and $R^3$ are joined by a

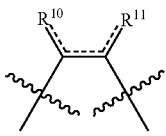

group; or
(ii) $R^3$ is O, $R^1$ is N, and $R^1$ and $R^2$ are joined by a

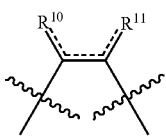

group;
for $R^4$, $R^5$ and $R^6$ either:
(i) $R^4$ is O, $R^6$ is N, and $R^5$ and $R^6$ are joined by a

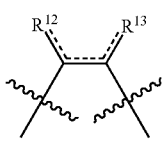

group; or
(ii) $R^6$ is O, $R^4$ is N, and $R^4$ and $R^5$ are joined by a

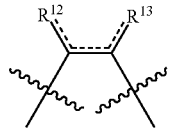

group;
$R^{10}$ and $R^{11}$ are joined to form: an optionally substituted monocyclic aromatic ring; or an optionally substituted polycyclic aromatic group;
$R^{12}$ and $R^{13}$ are joined to form: an optionally substituted monocyclic aromatic ring; or an optionally substituted polycyclic aromatic group;
each of $R^7$, $R^8$ and $R^9$ is either:
independently selected from hydrogen or

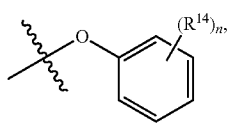

with the proviso that two of $R^7$, $R^8$ and $R^9$ are

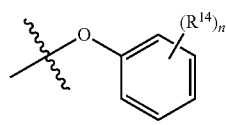

and the other is hydrogen; or
independently selected from hydrogen, bromine or chlorine, with the proviso that two of $R^7$, $R^8$ and $R^9$ are either bromine or chlorine, and the other is hydrogen;
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;
===== represents the presence of a single or double bond; and
n is an integer selected from 0, 1, 2, 3, 4 or 5.

The compound of Formula (I) can exist as two geometric isomer a syn isomer and an anti isomer.

In one embodiment the compound of Formula (I) is a salt.

Also disclosed herein are compounds of Formula (I-A):

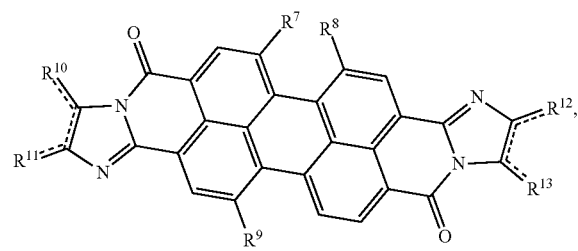

(I-A)

or an isomer or salt thereof, wherein:
- $R^{10}$ and $R^{11}$ are joined to form: an optionally substituted monocyclic aromatic ring; or an optionally substituted polycyclic aromatic group;
- $R^{12}$ and $R^{13}$ are joined to form: an optionally substituted monocyclic aromatic ring; or an optionally substituted polycyclic aromatic group;
- each of $R^7$, $R^8$ and $R^9$ is either:
  independently selected from hydrogen or

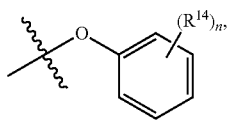

with the proviso that two of $R^7$, $R^8$ and $R^9$ are

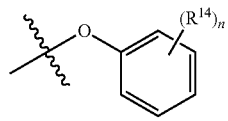

and the other is hydrogen; or
independently selected from hydrogen, bromine or chlorine, with the proviso that two of $R^7$, $R^8$ and $R^9$ are either bromine or chlorine, and the other is hydrogen;
- each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;
- ===== represents the presence of a single or double bond; and
- n is an integer selected from 0, 1, 2, 3, 4 or 5.

Also disclosed herein are compounds of Formula (I-A1):

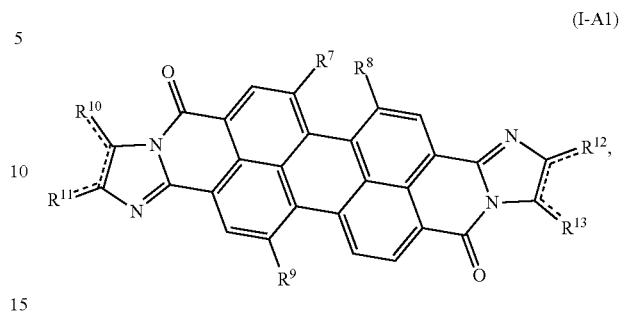

(I-A1)

or an isomer or salt thereof, wherein:
- $R^{10}$ and $R^{11}$ are joined to form: an optionally substituted monocyclic aromatic ring; or an optionally substituted polycyclic aromatic group;
- $R^{12}$ and $R^{13}$ are joined to form: an optionally substituted monocyclic aromatic ring; or an optionally substituted polycyclic aromatic group;
- each of $R^7$, $R^8$ and $R^9$ is independently selected from hydrogen or

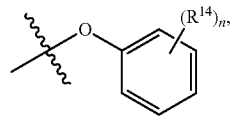

with the proviso that two of $R^7$, $R^8$ and $R^9$ are

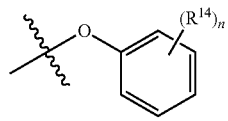

and the other is hydrogen;
- each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;
- ===== represents the presence of a single or double bond; and
- n is an integer selected from 0, 1, 2, 3, 4 or 5.

Also disclosed herein are compounds of Formula (I-A2):

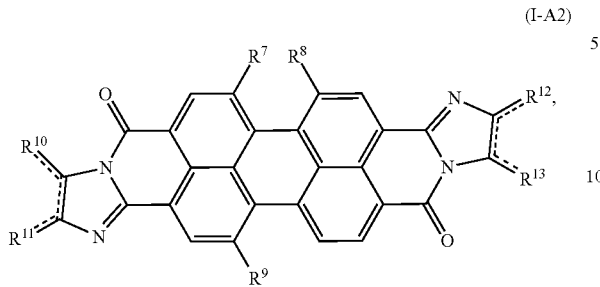

(I-A2)

or an isomer or salt thereof, wherein:
$R^{10}$ and $R^{11}$ are joined to form: an optionally substituted monocyclic aromatic ring; or an optionally substituted polycyclic aromatic group;
$R^{12}$ and $R^{13}$ are joined to form: an optionally substituted monocyclic aromatic ring; or an optionally substituted polycyclic aromatic group;
each of $R^7$, $R^8$ and $R^9$ is independently selected from hydrogen, bromine or chlorine, with the proviso that two of $R^7$, $R^8$ and $R^9$ are either bromine or chlorine, and the other is hydrogen;
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;
===== represents the presence of a single or double bond; and
n is an integer selected from 0, 1, 2, 3, 4 or 5.

Also disclosed herein are compounds of Formula (I-B):

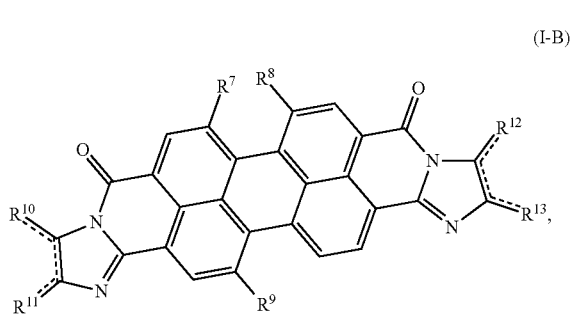

(I-B)

or an isomer or salt thereof, wherein:
$R^{10}$ and $R^{11}$ are joined to form: an optionally substituted monocyclic aromatic ring; or an optionally substituted polycyclic aromatic group;

$R^{12}$ and $R^{13}$ are joined to form: an optionally substituted monocyclic aromatic ring; or an optionally substituted polycyclic aromatic group;
each of $R^7$, $R^8$ and $R^9$ is either:
independently selected from hydrogen or

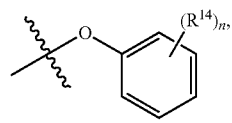

with the proviso that two of $R^7$, $R^8$ and $R^9$ are

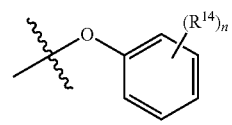

and the other is hydrogen; or
independently selected from hydrogen, bromine or chlorine, with the proviso that two of $R^7$, $R^8$ and $R^9$ are either bromine or chlorine, and the other is hydrogen;
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;
===== represents the presence of a single or double bond; and
n is an integer selected from 0, 1, 2, 3, 4 or 5.

Also disclosed herein are compounds of Formula (I-B1):

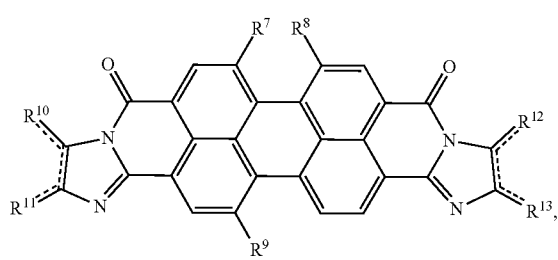

(I-B1)

or an isomer or salt thereof, wherein:
$R^{10}$ and $R^{11}$ are joined to form: an optionally substituted monocyclic aromatic ring; or an optionally substituted polycyclic aromatic group;
$R^{12}$ and $R^{13}$ are joined to form: an optionally substituted monocyclic aromatic ring; or an optionally substituted polycyclic aromatic group;

each of $R^7$, $R^8$ and $R^9$ is independently selected from hydrogen or

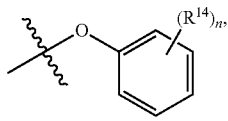

with the proviso that two of $R^7$, $R^8$ and $R^9$ are

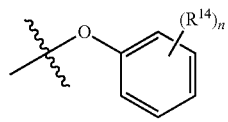

and the other is hydrogen;

each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;

===== represents the presence of a single or double bond; and n is an integer selected from 0, 1, 2, 3, 4 or 5.

Also disclosed herein are compounds of Formula (I-B2):

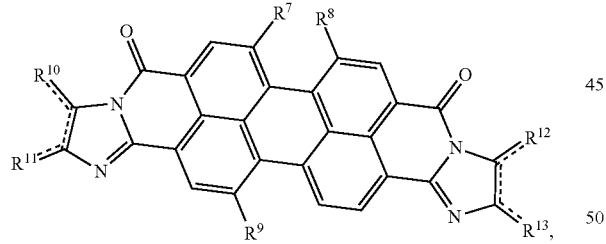

(I-B2)

or an isomer or salt thereof, wherein:
$R^{10}$ and $R^{11}$ are joined to form: an optionally substituted monocyclic aromatic ring; or an optionally substituted polycyclic aromatic group;
$R^{12}$ and $R^{13}$ are joined to form: an optionally substituted monocyclic aromatic ring; or an optionally substituted polycyclic aromatic group;
each of $R^7$, $R^8$ and $R^9$ independently selected from hydrogen, bromine or chlorine, with the proviso that two of $R^7$, $R^8$ and $R^9$ are either bromine or chlorine, and the other is hydrogen;
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;

===== represents the presence of a single or double bond; and n is an integer selected from 0, 1, 2, 3, 4 or 5.

Also disclosed herein are compounds of Formula (I-C):

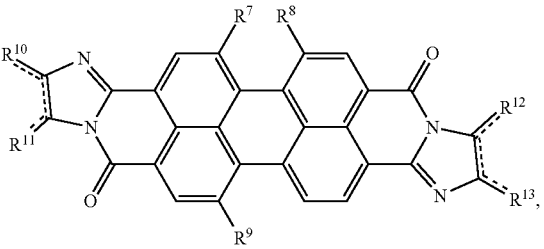

(I-C)

or an isomer or salt thereof, wherein:
$R^{10}$ and $R^{11}$ are joined to form: an optionally substituted monocyclic aromatic ring; or an optionally substituted polycyclic aromatic group;
$R^{12}$ and $R^{13}$ are joined to form: an optionally substituted monocyclic aromatic ring; or an optionally substituted polycyclic aromatic group;
each of $R^7$, $R^8$ and $R^9$ is either:
independently selected from hydrogen or

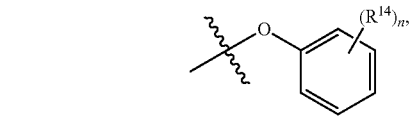

with the proviso that two of $R^7$, $R^8$ and $R^9$ are

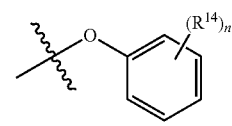

and the other is hydrogen; or
independently selected from hydrogen, bromine or chlorine, with the proviso that two of $R^7$, $R^8$ and $R^9$ are either bromine or chlorine, and the other is hydrogen;
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;

===== represents the presence of a single or double bond; and n is an integer selected from 0, 1, 2, 3, 4 or 5.

Also disclosed herein are compounds of Formula (I-C1):

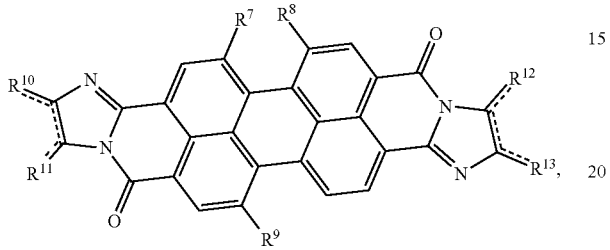

(I-C1)

or an isomer or salt thereof, wherein:
R$^{10}$ and R$^{11}$ are joined to form: an optionally substituted monocyclic aromatic ring; or an optionally substituted polycyclic aromatic group;
R$^{12}$ and R$^{13}$ are joined to form: an optionally substituted monocyclic aromatic ring; or an optionally substituted polycyclic aromatic group;
each of R$^7$, R$^8$ and R$^9$ is independently selected from hydrogen or

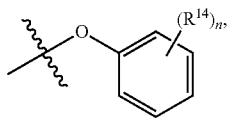

with the proviso that two of R$^7$, R$^8$ and R$^9$ are

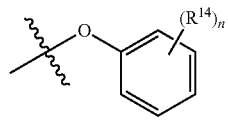

and the other is hydrogen;
each R$^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;

===== represents the presence of a single or double bond; and n is an integer selected from 0, 1, 2, 3, 4 or 5.

Also disclosed herein are compounds of Formula (I-C2):

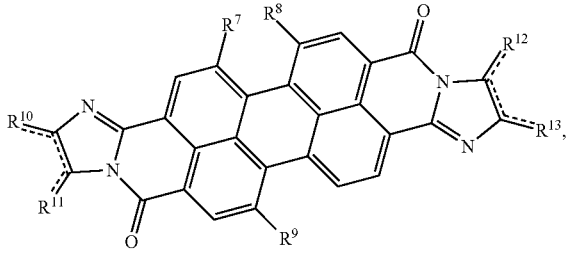

(I-C2)

or an isomer or salt thereof, wherein:
R$^{10}$ and R$^{11}$ are joined to form: an optionally substituted monocyclic aromatic ring; or an optionally substituted polycyclic aromatic group;
R$^{12}$ and R$^{13}$ are joined to form: an optionally substituted monocyclic aromatic ring; or an optionally substituted polycyclic aromatic group;
each of R$^7$, R$^8$ and R$^9$ independently selected from hydrogen, bromine or chlorine, with the proviso that two of R$^7$, R$^8$ and R$^9$ are either bromine or chlorine, and the other is hydrogen;
each R$^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;

===== represents the presence of a single or double bond; and n is an integer selected from 0, 1, 2, 3, 4 or 5.

Also disclosed herein are compounds of Formula (I-D):

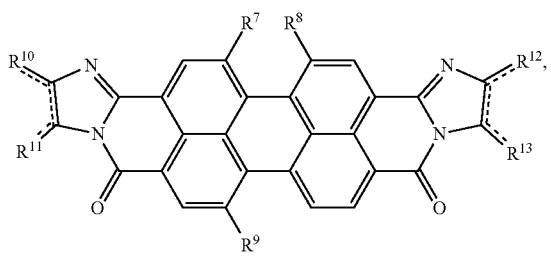

(I-D)

or an isomer or salt thereof, wherein:
R$^{10}$ and R$^{11}$ are joined to form: an optionally substituted monocyclic aromatic ring; or an optionally substituted polycyclic aromatic group;
R$^{12}$ and R$^{13}$ are joined to form: an optionally substituted monocyclic aromatic ring; or an optionally substituted polycyclic aromatic group;

each of $R^7$, $R^8$ and $R^9$ is either:
   independently selected from hydrogen or

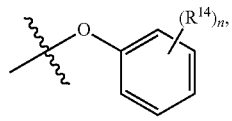

with the proviso that two of $R^7$, $R^8$ and $R^9$ are

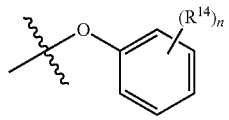

and the other is hydrogen; or
   independently selected from hydrogen, bromine or chlorine, with the proviso that two of $R^7$, $R^8$ and $R^9$ are either bromine or chlorine, and the other is hydrogen;
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;
===== represents the presence of a single or double bond; and
and
n is an integer selected from 0, 1, 2, 3, 4 or 5.
Also disclosed herein are compounds of Formula (I-D1):

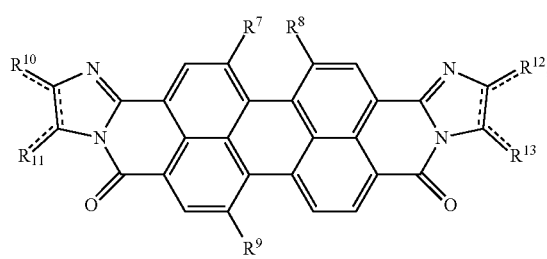

(I-D1)

or an isomer or salt thereof, wherein:
   $R^{10}$ and $R^{11}$ are joined to form: an optionally substituted monocyclic aromatic ring; or an optionally substituted polycyclic aromatic group;
   $R^{12}$ and $R^{13}$ are joined to form: an optionally substituted monocyclic aromatic ring; or an optionally substituted polycyclic aromatic group;

each of $R^7$, $R^8$ and $R^9$ is independently selected from hydrogen or

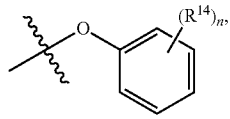

with the proviso that two of $R^7$, $R^8$ and $R^9$ are

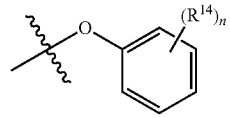

and the other is hydrogen;
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;
===== represents the presence of a single or double bond; and
n is an integer selected from 0, 1, 2, 3, 4 or 5.
Also disclosed herein are compounds of Formula (I-D2):

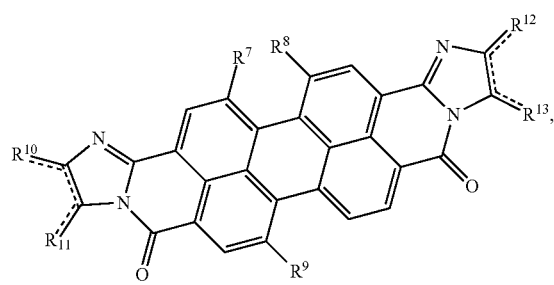

(I-D2)

or an isomer or salt thereof, wherein:
   $R^{10}$ and $R^{11}$ are joined to form: an optionally substituted monocyclic aromatic ring; or an optionally substituted polycyclic aromatic group;
   $R^{12}$ and $R^{13}$ are joined to form: an optionally substituted monocyclic aromatic ring; or an optionally substituted polycyclic aromatic group;
   each of $R^7$, $R^8$ and $R^9$ independently selected from hydrogen, bromine or chlorine, with the proviso that two of $R^7$, $R^8$ and $R^9$ are either bromine or chlorine, and the other is hydrogen;
   each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents;

===== represents the presence of a single or double bond; and n is an integer selected from 0, 1, 2, 3, 4 or 5.

In one embodiment the compound of Formula (I) is a compound of Formula (I-A). In another embodiment the compound of Formula (I) is a compound of Formula (I-A1). In yet another embodiment the compound of Formula (I) is a compound of Formula (I-A2).

In one embodiment the compound of Formula (I) is a compound of Formula (I-B). In another embodiment the compound of Formula (I) is a compound of Formula (I-B1). In yet another embodiment the compound of Formula (I) is a compound of Formula (I-B2).

In one embodiment the compound of Formula (I) is a compound of Formula (I-C). In another embodiment the compound of Formula (I) is a compound of Formula (I-C1). In yet another embodiment the compound of Formula (I) is a compound of Formula (I-C2).

In one embodiment the compound of Formula (I) is a compound of Formula (I-D). In another embodiment the compound of Formula (I) is a compound of Formula (I-D1). In yet another embodiment the compound of Formula (I) is a compound of Formula (I-D2).

Herein "joined to form an optionally substituted monocyclic aromatic ring" or "are joined to form an optionally substituted polycyclic aromatic ring" means that two identified groups (for example $R^{10}$ and $R^{11}$ and/or $R^{12}$ and $R^{13}$) are taken with intervening atoms to form an optionally substituted monocyclic aromatic ring, such as an optionally substituted

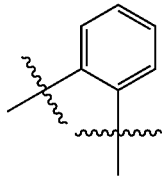 [SMILES: *c1ccccc1*]

group, or an optionally substituted polycyclic aromatic group, such as an optionally substituted

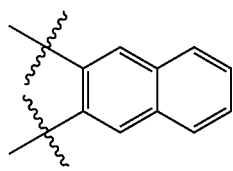 [SMILES: *c1cc2ccccc2cc1*]

group, respectively.

In one embodiment $R^{10}$ and $R^{11}$ are joined to form an optionally substituted monocyclic aromatic ring, and/or $R^{12}$ and $R^{13}$ are joined to form an optionally substituted monocyclic aromatic ring. In another embodiment $R^{10}$ and $R^{11}$ are joined to form an optionally substituted monocyclic aromatic ring, and $R^{12}$ and $R^{13}$ are joined to form an optionally substituted monocyclic aromatic ring.

In one embodiment $R^{10}$ and $R^{11}$ are joined to form an optionally substituted polycyclic aromatic ring, and/or $R^{12}$ and $R^{13}$ are joined to form an optionally substituted polycyclic aromatic ring. In another embodiment $R^{10}$ and $R^{11}$ are joined to form an optionally substituted polycyclic aromatic ring, and $R^{12}$ and $R^{13}$ are joined to form an optionally substituted polycyclic aromatic ring.

In one embodiment $R^{10}$ and $R^{11}$, and $R^{12}$ and $R^{13}$ both independently form a monocyclic aromatic ring which is unsubstituted. In another embodiment $R^{10}$ and $R^{11}$, and $R^{12}$ and $R^{13}$ both independently form a polycyclic aromatic group which is unsubstituted. In another embodiment $R^{10}$ and $R^{11}$, and $R^{12}$ and $R^{13}$ both independently form a monocyclic aromatic ring which is substituted. In yet another embodiment $R^{10}$ and $R^{11}$, and $R^{12}$ and $R^{13}$ both independently form a polycyclic aromatic group which is substituted.

The polycyclic aromatic group may comprise 2, 3, 4, 5 or 6 fused ring systems, wherein each ring is optionally substituted. The polycyclic aromatic group comprises a plurality of ring structures, wherein at least one of these rings is aromatic. In one embodiment all the rings are aromatic.

The optionally substituted monocyclic aromatic ring may be a heterocycle. The optionally substituted polycyclic aromatic group may comprise one or more heterocycles. Exemplary heterocycles include, but are not limited to optionally substituted: acridine; adenine; azepine; azole; 2H-azole; 3H-azole; benzimidazole; benzisoxazole; 2,1-benzisoxazole; benzofuran; 2H-1-benzopyran; 2H-1-benzopyran-2-one; 4H-1-benzopyran-4-one; 1H-2-benzopyran-1-one; 3H-2-benzopyran-3-one; benzothiazole; benzo[b]thiophene; benzo[c]thiophene; 1H-2,3-benzoxazine; 2H-1,3-benzoxazine; 2H-1,4-benzoxazine; 4H-1,4-benzoxazine; 4H-3,1-benzoxazine; 2H-1,2,4-benzoxadiazine; benzoxazole; cinnoline; coumaran; coumarin; cyclopenta[b]pyridine; 7-deazapurine; 7-deaza-8-azapurine; 9-deazapurine; 4H-1,2-diazepine; 1,2-diazole; 1,3-diazole; 1,4-dioxane; 3H-1,2,3-dioxazole; 1,2,4-dioxazole; 1,3,2-dioxazole; 2H-1,3,4-dioxazole; 1,2-dioxin; 1,3-dioxin; 1,3-dioxolane; 1,3-dithiane; 1,4-dithiane; 2H-1,3-dithiole; 3H-1,2-dithiole; furan; furazan; carbazole; carbolines; α-carboline; ⊖-carboline; γ-carboline; δ-carboline; 2H-chromene; chromen-4-one; guanine; hipoxanthine; imidazolidine; 1H-imidazole; 2H-lmidazole; 2-imidazoline; imidazoline-2-thione; imidazo[1,5-a]pyrimidine; 1H-indazole; indole; 3H-indole; indoline; indoxazine; isobenzofuran; isochromen-3-one; isocoumarin; 1H-isoindole; isoquinoline; isothiazole; isoxazole; 1,2,3,5-oxatriazole; 5-oxazolone; 5H-1,2,5-oxathiazole; 1,3-oxathiole; 2H-1,2-oxazine; 2H-1,3-oxazine; 2H-1,4-oxazine; 4H-1,2-oxazine; 4H-1,4-oxazine; 6H-1,2-oxazine; 6H-1,3-oxazine; 1,2,5-oxathiazine; 1,2,6-oxathiazine; 1,2,4-oxadiazine; 1,3,5-oxadiazine; oxepin; morpholine; 1,5-naphthyridine; 1,6-naphthyridine; 1,7-naphthyridine; 1,8-naphthyridine; 3H-1,2-oxathiole; oxazole; 1,2-oxazole; 1,3-oxazole; 1,2,3-oxadiazole; 1,2,4-oxadiazole; 1,2,5-oxadiazole; 1,3,4-oxadiazole; 1,2,3,4-oxatriazole; phenazine; phenothiazine; phthalazine; piperazine; piperidine; pteridine; purine; 2H-pyran; 2H-pyran-2-one; 4H-pyran-4-one; pyrano[3,4-b]pyrrole; pyrazine; pyrazole; pyrazolidine; 2-pyrazoline; pyrazolo[1,5-a]pyrimidine; 1H-pyrazolo[3,4-d]pyrimidine; pyridazine; pyridine; pyrimidine; 1,3,5-trithiane; 2-pyrone; thiepin; 4-pyrone; thymine; pyrrole; 2H-pyrrole; 3H-pyrrole; uracil;

pyrrolidine; 2-pyrroline; 3-pyrroline; xanthene; 5H-pyrrolo[3,2-d]pyrimidine; xanthine; 7H-pyrrolor[2,3-a]pyrimidine; quinazoline; quinoline; 4H-quinolizine; quinoxaline; quinuclidine; tetrahydrofuran; tetrahydrothiophene; thiophene; 1,2,3-triazole; 1,2,4-triazole; 2-thiazoline; thiazole; 1,3-thiazole; 1,2-thiazole; 1,3,4-thiadiazole; 1,3,5-triazine; s-triazine; 1,2,4-triazine; as-triazine; 1,2,3-triazine; v-triazine; and thiomorpholine groups; and combinations thereof.

In one embodiment the optionally substituted monocyclic aromatic ring or optionally substituted polycyclic aromatic group formed by $R^{10}$ and $R^{11}$ is the same as the optionally substituted monocyclic aromatic ring or the optionally substituted polycyclic aromatic group formed by $R^{12}$ and $R^{13}$.

Examples of monocyclic aromatic rings and polycyclic aromatic rings which may optionally be substituted includes, but is not limited to: phenyl, naphthalene, anthracene, phenanthrene, tetracene, chrysene, triphenylene, pyrene, pentacene, benzo[a]pyrene, and dibenz[a,h]anthracene rings, or mixtures thereof.

Other examples of monocyclic aromatic rings and polycyclic aromatic rings which may optionally be substituted includes, but is not limited to any one of:

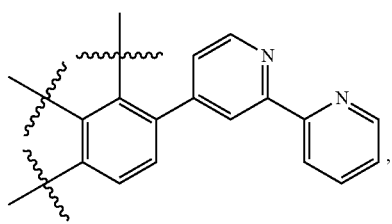

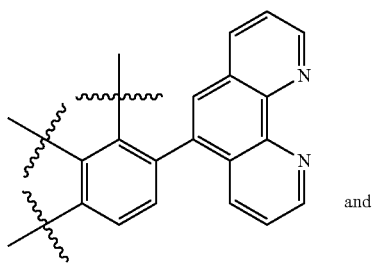

and

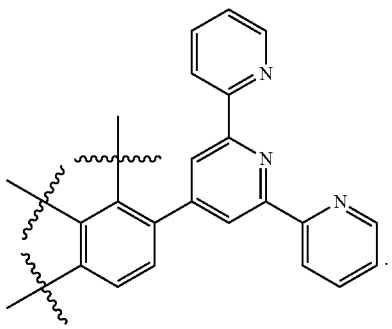

In these compounds

indicates possible positions of attachment.

In one embodiment, the monocyclic aromatic ring or polycyclic aromatic group may be selected from, but not limited to, optionally substituted:

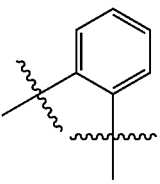 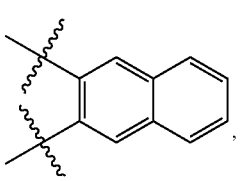

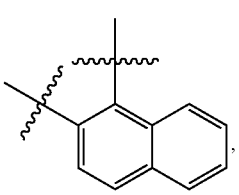 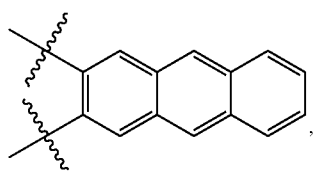

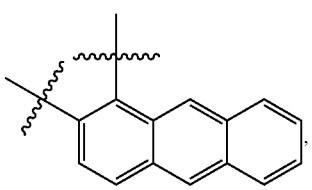

-continued
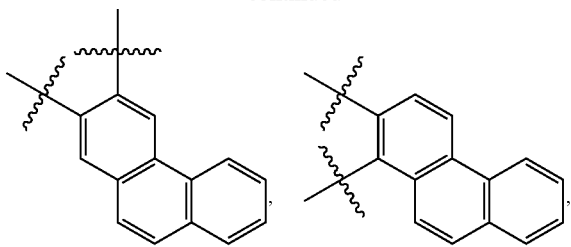
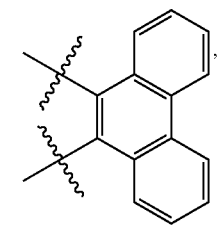
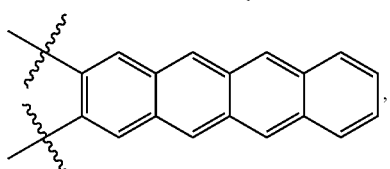
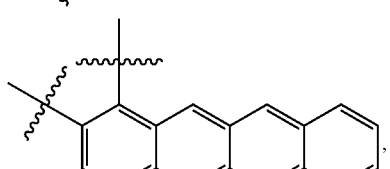
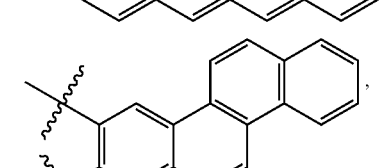
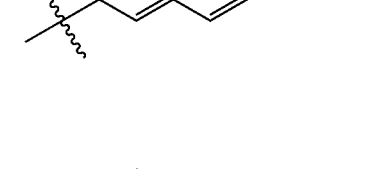
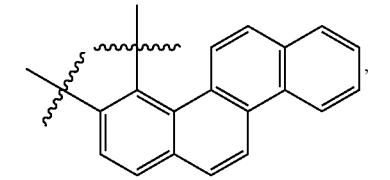
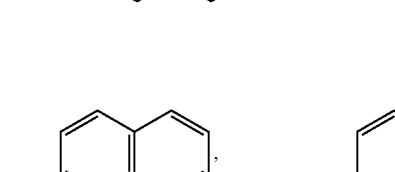
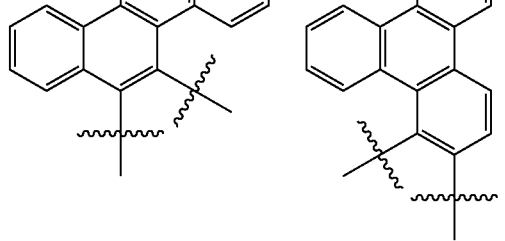
-continued
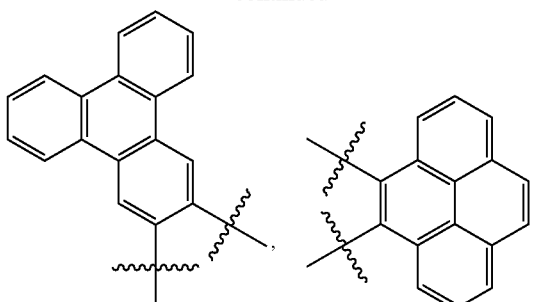
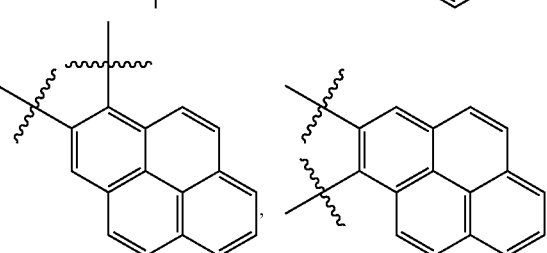
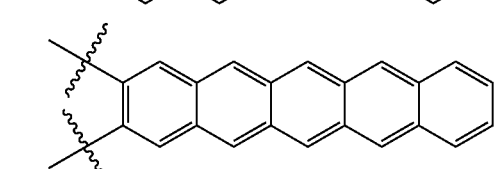
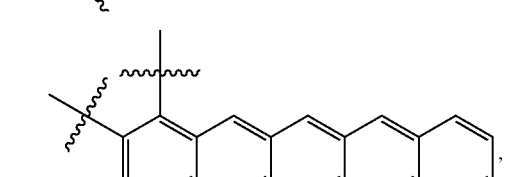
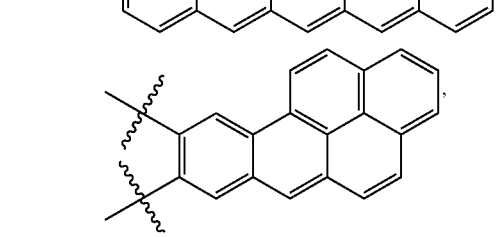
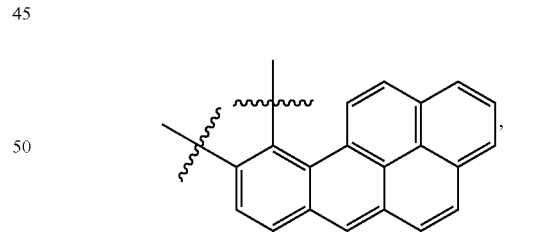
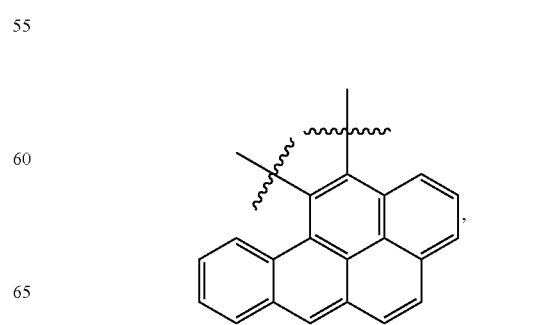

-continued
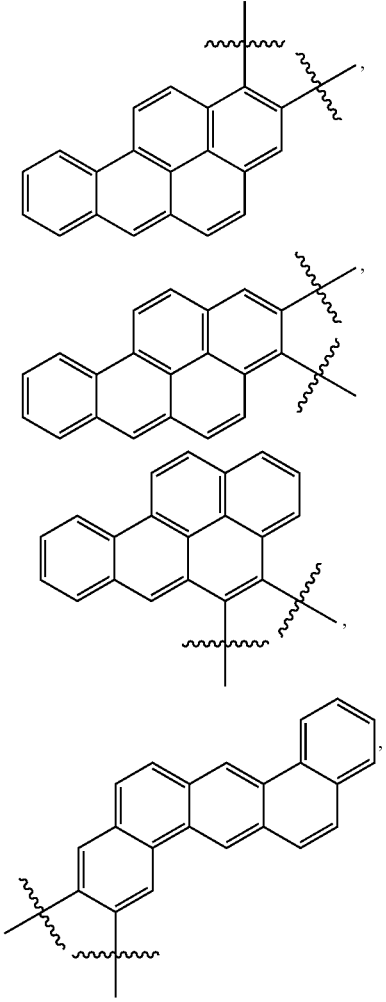
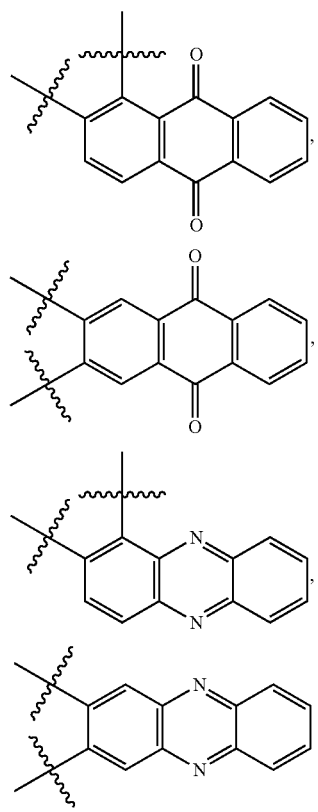
or mixtures thereof.
In another embodiment, the monocyclic aromatic ring or polycyclic aromatic group may be selected from, but not limited to, optionally substituted:
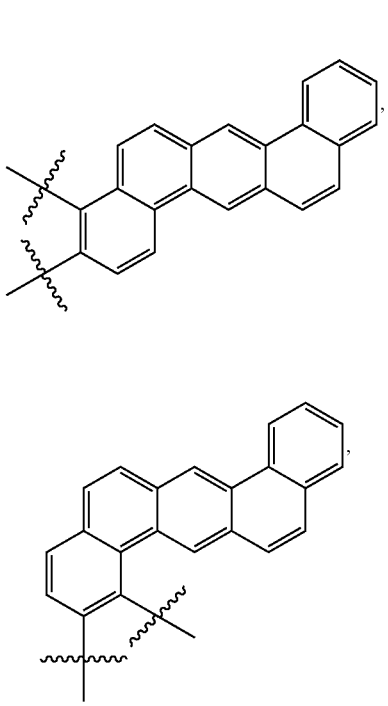
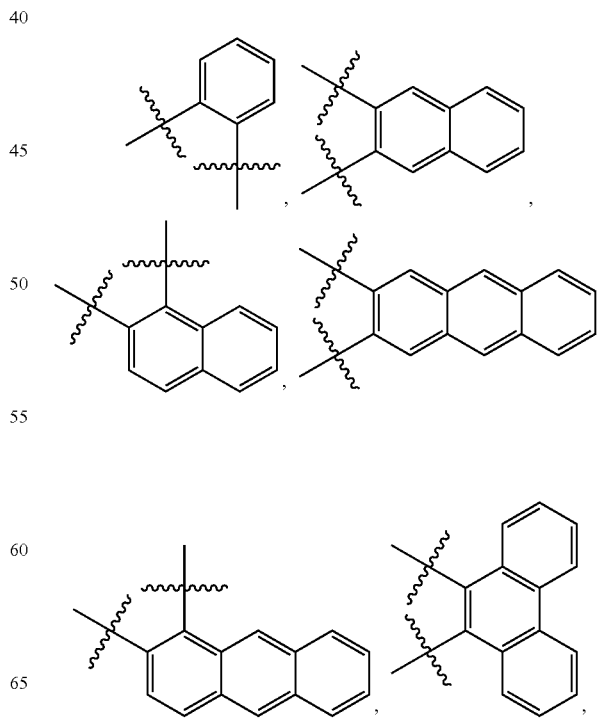

-continued

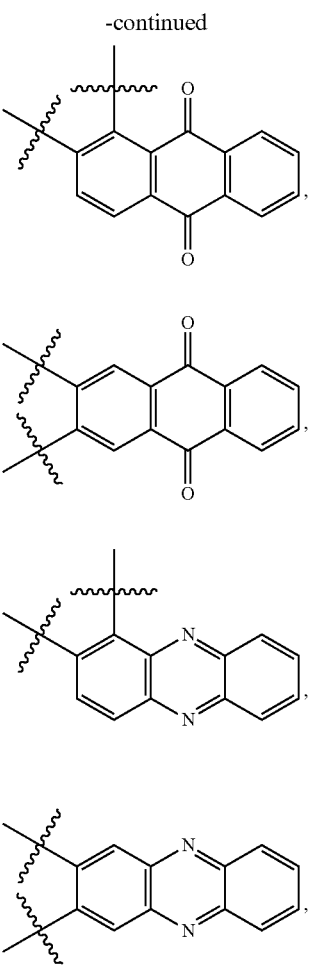

or mixtures thereof.

In yet another embodiment, the monocyclic aromatic ring or polycyclic aromatic group may be selected from, but not limited to, optionally substituted:

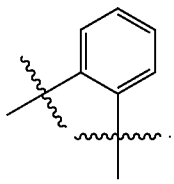 [SMILES: *c1ccccc1*]

In yet another embodiment, the monocyclic aromatic ring or polycyclic aromatic group may be selected from, but not limited to, optionally substituted:

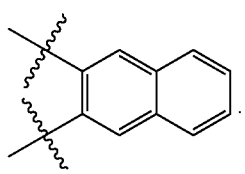 [SMILES: *c1cc2ccccc2cc1*]

In yet another embodiment, the monocyclic aromatic ring or polycyclic aromatic group may be selected from, but not limited to, optionally substituted:

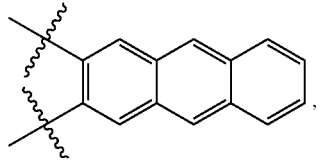 [SMILES: *c1cc2cc3ccccc3cc2cc1*]

for example

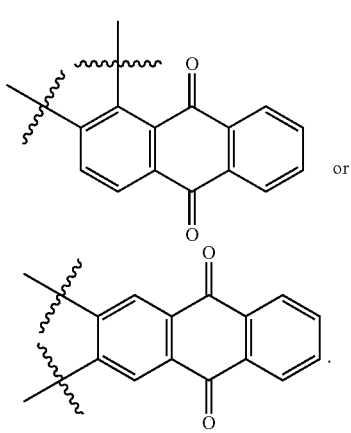

In yet another embodiment, the monocyclic aromatic ring or polycyclic aromatic group may be selected from, but not limited to, optionally substituted:

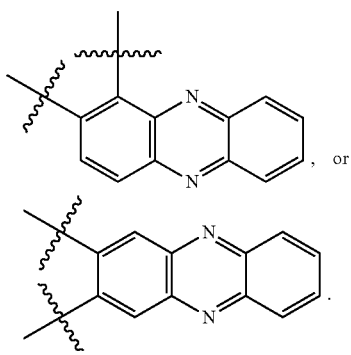

For compounds of Formula (I), (I-A), (I-B), (I-C) or (I-D), two of $R^7$, $R^8$ and $R^9$ may be

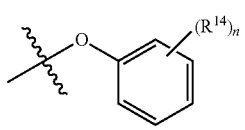

whilst the remaining group is hydrogen.

Herein, $R^1$ may be O or N. In one embodiment $R^1$ is O. In another embodiment $R^1$ is N.

Herein, $R^3$ may be O or N. In one embodiment $R^3$ is O. In another embodiment $R^3$ is N.

Herein, $R^4$ may be O or N. In one embodiment $R^4$ is O. In another embodiment $R^4$ is N.

Herein, $R^6$ may be O or N. In one embodiment $R^6$ is O. In another embodiment $R^6$ is N.

In one embodiment $R^1$ is O and $R^3$ is N, and $R^2$ and $R^3$ are joined by a

[structure with $R^{10}$ and $R^{11}$]

group. In another embodiment $R^3$ is O and $R^1$ is N, and $R^2$ and $R^1$ are joined by a

[structure with $R^{10}$ and $R^{11}$]

group.

In one embodiment $R^4$ is O and $R^6$ is N, and $R^5$ and $R^6$ are joined by a

[structure with $R^{12}$ and $R^{13}$]

group. In another embodiment $R^6$ is O and $R^4$ is N, and $R^5$ and $R^4$ are joined by a

[structure with $R^{12}$ and $R^{13}$]

group.

$R^7$ and $R^9$ may both be

[structure with $O$ and $(R^{14})_n$]

whilst $R^8$ is hydrogen. Alternatively, $R^8$ and $R^9$ may both be

[structure with $O$ and $(R^{14})_n$]

whilst $R^7$ is hydrogen.

In one embodiment, in compounds of Formula (I), (I-A), (I-B), (I-C) or (I-D), two of $R^7$, $R^8$ and $R^9$ may be bromine and the remaining group is hydrogen.

$R^7$ and $R^9$ may both be bromine, whilst $R^8$ is hydrogen. Alternatively, $R^8$ and $R^9$ may both be bromine, whilst $R^7$ is hydrogen.

In one embodiment, in compounds of Formula (I), (I-A), (I-B), (I-C) or (I-D), two of $R^7$, $R^8$ and $R^9$ may be chlorine and the remaining group is hydrogen.

$R^7$ and $R^9$ may both be chlorine, whilst $R^8$ is hydrogen. Alternatively, $R^8$ and $R^9$ may both be chlorine, whilst $R^7$ is hydrogen.

Each $R^{14}$ group may be an optionally substituted: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof. For example, $R^{14}$ may be an optionally substituted $C_1$-$C_{12}$ branched or straight chain alkyl group. $R^{14}$ may be an optionally substituted tert-butyl group or a $C_{12}$ straight chain alkyl group.

In addition, each $R^{14}$ may be selected from, but not limited to an optionally substituted appended: aryl, heteroaryl, pyridine, bipyridine, terpyridine or phenanthroline group. Each $R^{14}$ may be selected from:

[chemical structures]

-continued

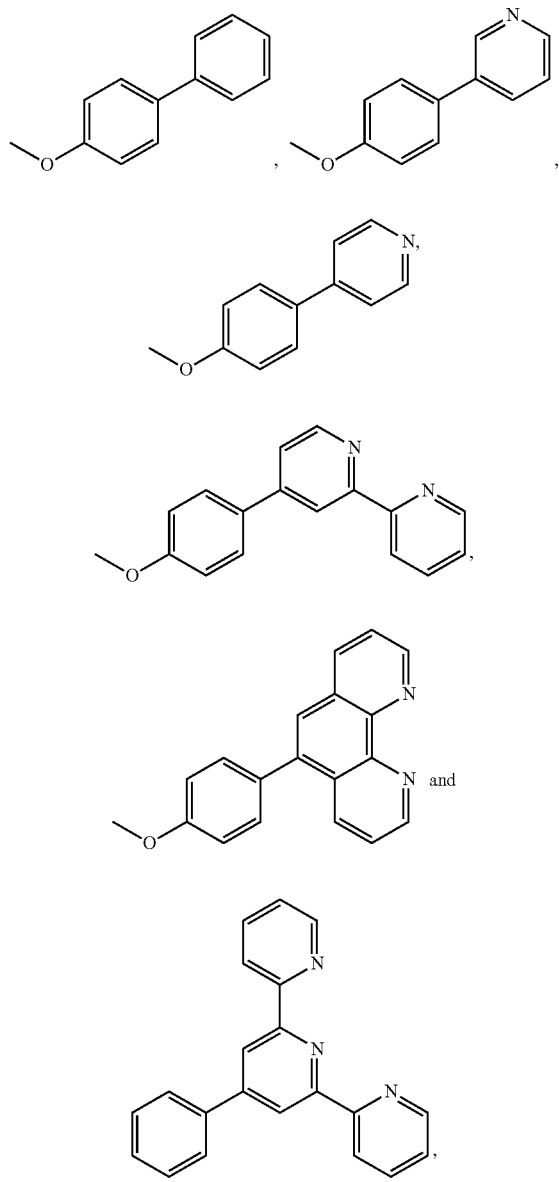

wherein R[14] may be attached at any carbon on an aryl ring in the aforementioned structures.

In one embodiment R[14] is an optionally substituted alkyl group. In another embodiment R[14] is an optionally substituted perylene. Examples of optionally substituted perylenes include those disclosed in: WO 2015/024064 A1, *ChemPhysChem*, 2011, 12, 595-608; *J. AM. CHEM. SOC.*, 2004, 126, 8284-8294; *Eur. J. Org. Chem.*, 2008, 4559-4562; *J. Mater. Chem.*, 2010, 20, 3814-3826; *Angew Chem Int Ed*, 2002, 41(11), 1900; and *Chem. Eur. J.*, 2004, 10, 1398-1414, the content of each is incorporated by reference.

Integer "n" may be selected from 0, 1, 2, 3, 4 or 5. In one embodiment n is 0. In another embodiment n is 1. In yet another embodiment, n is 2. In yet another embodiment, n is 3. In yet another embodiment, n is 4. In yet another embodiment, n is 5. When n is 2 or greater, each R[14] group may be the same or different.

Examples of compounds of Formula (I), (I-A), (I-B), (I-C) or (I-D) include, but are not limited, to optionally substituted:

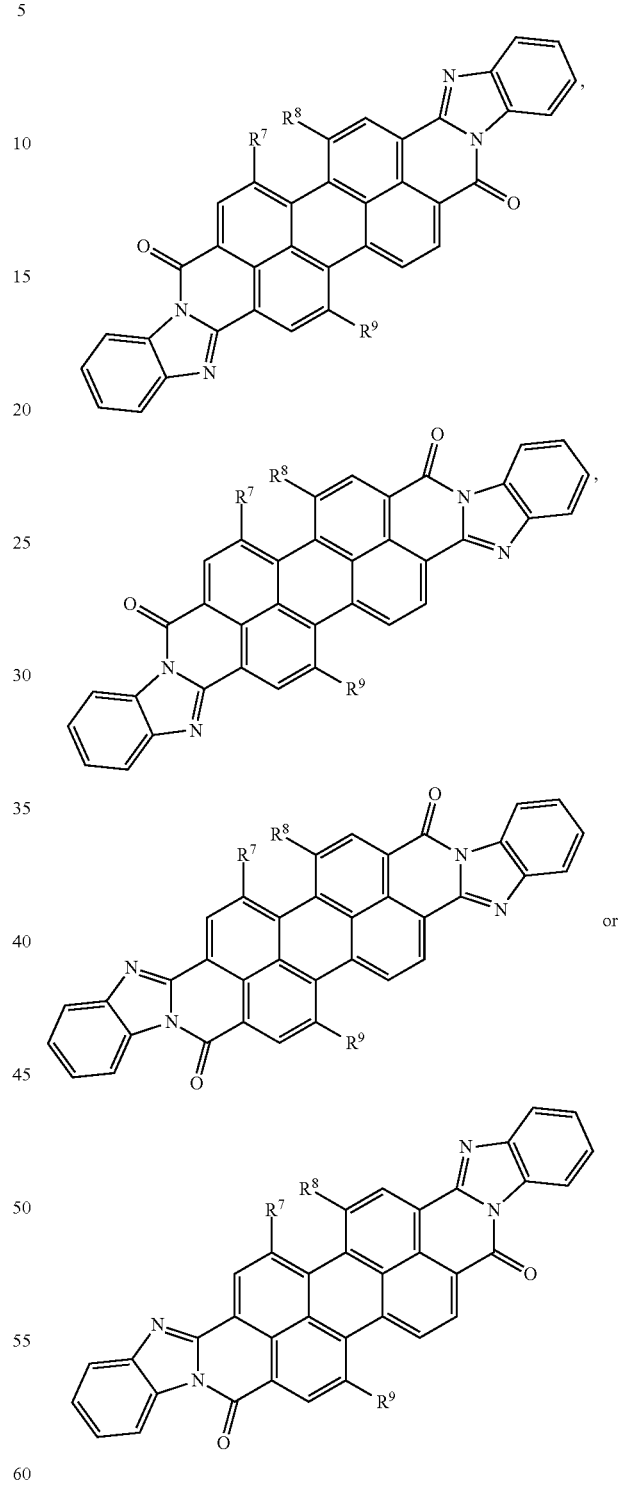

or an isomer or salt thereof, wherein R[7], R[8] or R[9] are as defined herein.

Examples of compounds of Formula (I), (I-A), (I-B), (I-C) or (I-D) include compounds where R[7], R[8], R[9], and the combinations of: $R^{10}$ and $R^{11}$; and $R^{12}$ and $R^{13}$, are limited to the following optionally substituted substituents in Table 1:

TABLE 1

Exemplified substituents

| $R^{10}$ and $R^{11}$ | $R^{12}$ and $R^{13}$ | $R^7$ |
|---|---|---|
| benzene (1,2-disubstituted) | benzene (1,2-disubstituted) | phenoxy |
| benzene (1,2-disubstituted) | benzene (1,2-disubstituted) | H |
| naphthalene (2,3-disubstituted) | naphthalene (2,3-disubstituted) | H |
| naphthalene (2,3-disubstituted) | naphthalene (2,3-disubstituted) | H |
| naphthalene (1,2-disubstituted) | naphthalene (1,2-disubstituted) | phenoxy |
| naphthalene (1,2-disubstituted) | naphthalene (1,2-disubstituted) | H |

TABLE 1-continued

Exemplified substituents

TABLE 1-continued
Exemplified substituents
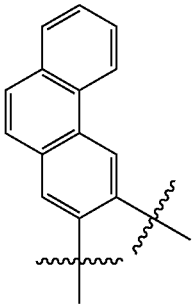 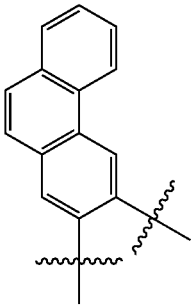 [SMILES: *c1cc2ccc3ccccc3c2cc1*] H
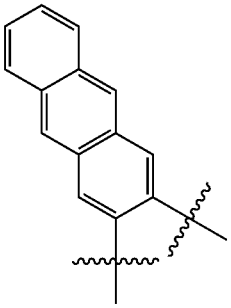 [SMILES: *c1cc2cc3ccccc3cc2cc1*] 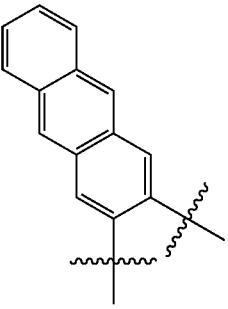 [SMILES: *c1cc2cc3ccccc3cc2cc1*] 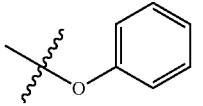 [SMILES: *Oc1ccccc1]
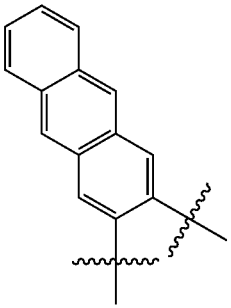 [SMILES: *c1cc2cc3ccccc3cc2cc1*] 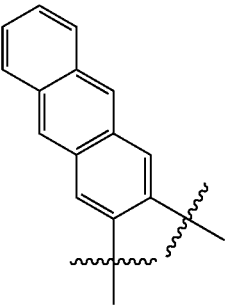 [SMILES: *c1cc2cc3ccccc3cc2cc1*] H
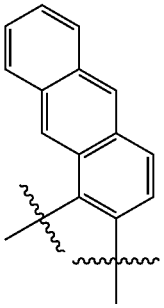 [SMILES: *c1ccc2cc3ccccc3cc2c1*] 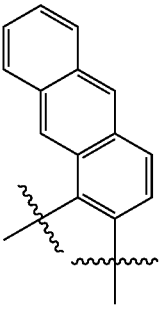 [SMILES: *c1ccc2cc3ccccc3cc2c1*] 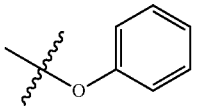 [SMILES: *Oc1ccccc1]
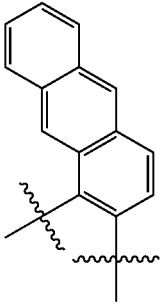 [SMILES: *c1ccc2cc3ccccc3cc2c1*] 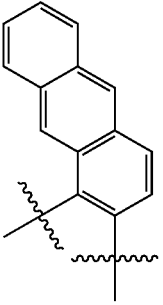 [SMILES: *c1ccc2cc3ccccc3cc2c1*] H TABLE 1-continued
Exemplified substituents
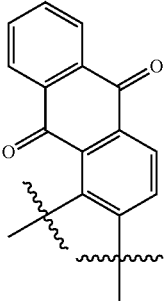 [SMILES: *c1ccc2c(c1*)C(=O)c1ccccc1C2=O] 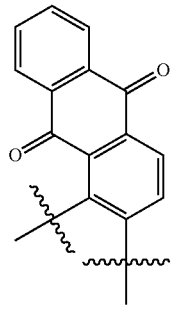 [SMILES: *c1ccc2c(c1*)C(=O)c1ccccc1C2=O] 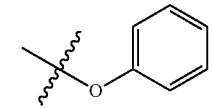 [SMILES: *Oc1ccccc1]
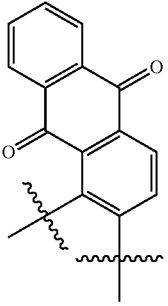 [SMILES: *c1ccc2c(c1*)C(=O)c1ccccc1C2=O] 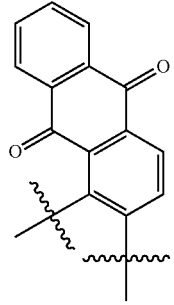 [SMILES: *c1ccc2c(c1*)C(=O)c1ccccc1C2=O] H
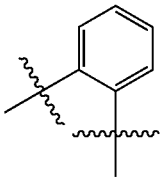 [SMILES: *c1ccccc1*] 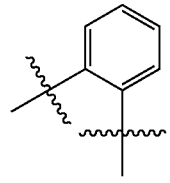 [SMILES: *c1ccccc1*] 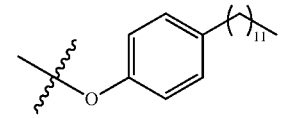
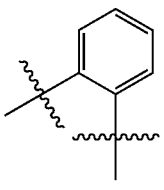 [SMILES: *c1ccccc1*] 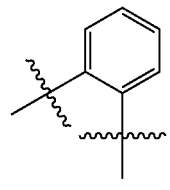 [SMILES: *c1ccccc1*] H
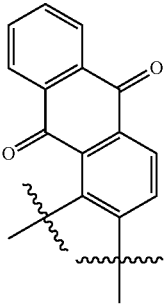 [SMILES: *c1ccc2c(c1*)C(=O)c1ccccc1C2=O] 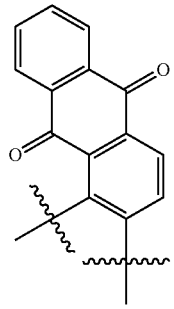 [SMILES: *c1ccc2c(c1*)C(=O)c1ccccc1C2=O] 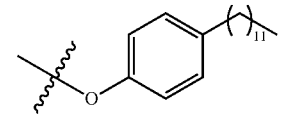

TABLE 1-continued

| Exemplified substituents | | |
|---|---|---|
| (anthraquinone-1,2-diyl) | (anthraquinone-1,2-diyl) | H |
| (benzene-1,2-diyl) | (benzene-1,2-diyl) | 4-tert-butylphenoxy |
| (benzene-1,2-diyl) | (benzene-1,2-diyl) | H |
| (phenazine-2,3-diyl) | (phenazine-2,3-diyl) | phenoxy |
| (phenazine-2,3-diyl) | (phenazine-2,3-diyl) | H |

TABLE 1-continued
Exemplified substituents
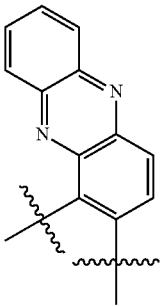 [SMILES: *c1ccc2nc3ccccc3nc2c1*] 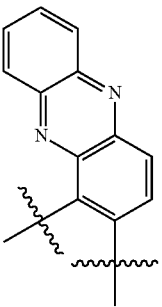 [SMILES: *c1ccc2nc3ccccc3nc2c1*] 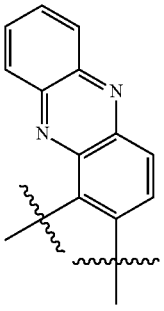 [SMILES: *c1ccc2nc3ccccc3nc2c1*]
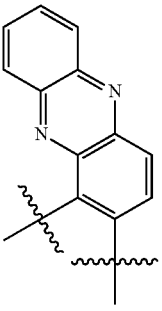 [SMILES: *c1ccc2nc3ccccc3nc2c1*] 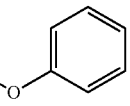 H
| $R^8$ | $R^9$ |
|---|---|
| H | 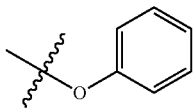 [SMILES: *Oc1ccccc1] |
| 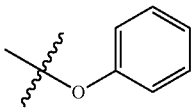 [SMILES: *Oc1ccccc1] | 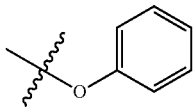 [SMILES: *Oc1ccccc1] |
| H | 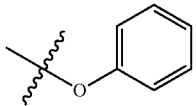 |
| 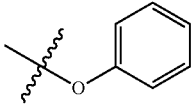 [SMILES: *Oc1ccccc1] | 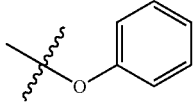 [SMILES: *Oc1ccccc1] |
| H | 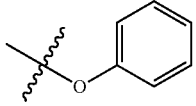 [SMILES: *Oc1ccccc1] |
| 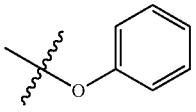 [SMILES: *Oc1ccccc1] | 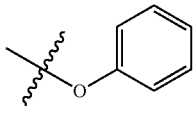 [SMILES: *Oc1ccccc1] |
| H | 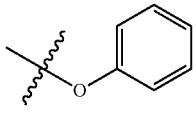 [SMILES: *Oc1ccccc1] |

TABLE 1-continued
Exemplified substituents
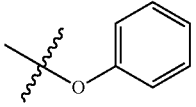 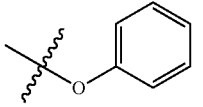 [SMILES: *Oc1ccccc1]
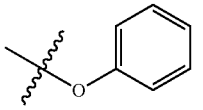 [SMILES: *Oc1ccccc1]
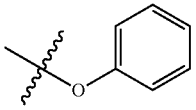 [SMILES: *Oc1ccccc1] 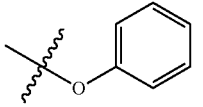 [SMILES: *Oc1ccccc1]
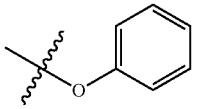 [SMILES: *Oc1ccccc1]
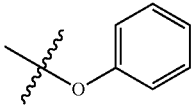 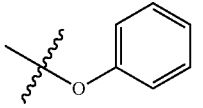 [SMILES: *Oc1ccccc1]
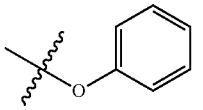 [SMILES: *Oc1ccccc1]
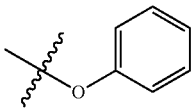 [SMILES: *Oc1ccccc1] 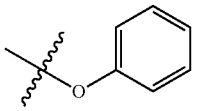 [SMILES: *Oc1ccccc1]
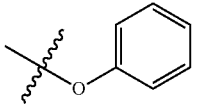 [SMILES: *Oc1ccccc1]
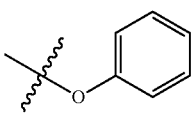 [SMILES: *Oc1ccccc1] 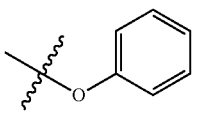 [SMILES: *Oc1ccccc1]
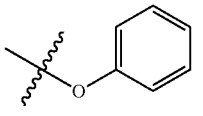 [SMILES: *Oc1ccccc1] 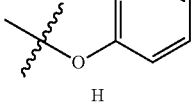
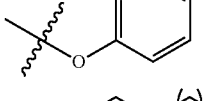 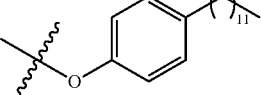
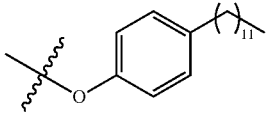 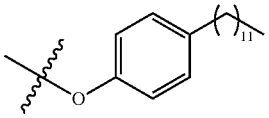

TABLE 1-continued
Exemplified substituents
H 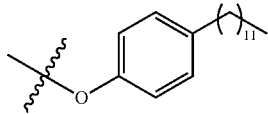
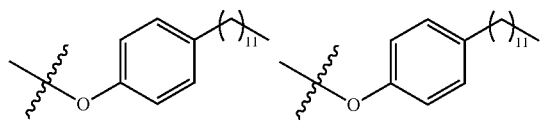
H 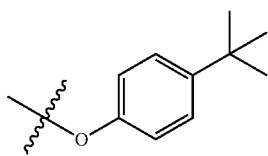 [SMILES: *Oc1ccc(C(C)(C)C)cc1]
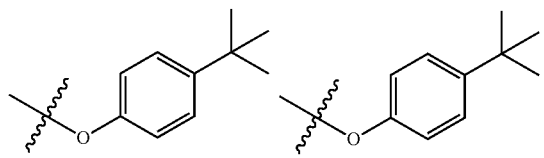
H 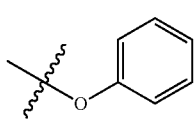 [SMILES: *Oc1ccccc1]
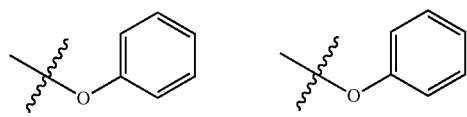
H 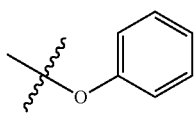 [SMILES: *Oc1ccccc1]
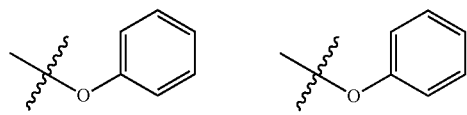

Examples of compounds of Formula (I), (I-A), (I-B), (I-C) or (I-D) include compounds where $R^7$, $R^8$, $R^9$, and the combinations of: $R^{10}$ and $R^{11}$; and $R^{12}$ and $R^{13}$, are limited to the following optionally substituted substituents in Table 2:

TABLE 2

| Exemplified substituents | | | | |
|---|---|---|---|---|
| $R^{10}$ and $R^{11}$ | $R^{12}$ and $R^{13}$ | $R^7$ | $R^8$ | $R^9$ |
| [structure] | [structure] | Br | H | Br |
| [structure] | [structure] | H | Br | Br |
| [structure] | [structure] | Br | H | Br |
| [structure] | [structure] | H | Br | Br |
| [structure] | [structure] | Br | H | Br |
| [structure] | [structure] | H | Br | Br |

TABLE 2-continued

| Exemplified substituents | | | | |
|---|---|---|---|---|
| $R^{10}$ and $R^{11}$ | $R^{12}$ and $R^{13}$ | $R^7$ | $R^8$ | $R^9$ |
| [structure] | [structure] | Br | H | Br |
| [structure] | [structure] | H | Br | Br |
| [structure] | [structure] | Br | H | Br |
| [structure] | [structure] | H | Br | Br |
| [structure] | [structure] | Br | H | Br |

TABLE 2-continued

Exemplified substituents

| R¹⁰ and R¹¹ | R¹² and R¹³ | R⁷ | R⁸ | R⁹ |
|---|---|---|---|---|
| (naphthacene-linked) | (naphthacene-linked) | H | Br | Br |
| (anthracene-linked) | (anthracene-linked) | Br | H | Br |
| (anthracene-linked) | (anthracene-linked) | H | Br | Br |
| (phenanthrene-linked) | (phenanthrene-linked) | Br | H | Br |
| (anthracene-linked, alt) | (anthracene-linked, alt) | H | Br | Br |
| (anthraquinone-linked) | (anthraquinone-linked) | Br | H | Br |
| (anthraquinone-linked) | (anthraquinone-linked) | H | Br | Br |
| (phenazine-linked) | (phenazine-linked) | Br | H | Br |
| (phenazine-linked) | (phenazine-linked) | H | Br | Br |

TABLE 2-continued

Exemplified substituents

| $R^{10}$ and $R^{11}$ | $R^{12}$ and $R^{13}$ | $R^7$ | $R^8$ | $R^9$ |
|---|---|---|---|---|
| (phenazine structure) | (phenazine structure) | Br | H | Br |
| (phenazine structure) | (phenazine structure) | H | Br | Br |

Alternative compounds in Table 2 are where the Br substituents are replaced with Cl substituents.

A compound of Formula (I), (I-A), (I-B), (I-C) or (I-D) may have a purity in a range of about 85 to about 95%. Alternatively a compound of Formula (I), (I-A), (I-B), (I-C) or (I-D) may have a purity of: at least 95%, at least 96%, at least 97%, at least 98% or a purity of greater than 98%.

Absorbance and Fluorescence

Compounds of Formula (I) or Formula (II) may be used as dyes, for example fluorescent dyes. They may also serve as charge transfer dyes or light harvesting dyes for organic solar cells or organic light emitting diodes (OLEDs). They may also serve as vat dyes for textiles. They may also be useful as dyes for dispersion in polymeric resins.

Examples of polymeric resins include polymers which comprise: an acrylic, a urethane; an ester; a methacrylate; a thiophene; a co-polymer of any bond conjugated polymer; a light transparent polymer; a low ultra violet absorbent polymer; a heat conducting polymer; or an electrically conducting polymer. In another embodiment, the polymer may be: aniline based; pyrrole based; acetylene based; or furan based.

In another embodiment, the polymer may comprise polyurethane, polyester, polyamide, polyurea, polycarbonate and polymethyl methacrylate. The constituent monomers in the polymers of the present disclosure may be methacrylate-based, carbonate-based, acrylamide-based, methacrylamide-based, or styrene-based monomers.

Constituent monomers of the vinyl polymers that may be used include acrylic esters, specifically, e.g., methyl acrylate, ethyl acrylate, n-propyl acrylate, isopropyl acrylate, n-butyl acrylate, isobutyl acrylate, sec-butyl acrylate, tert-butyl acrylate, amyl acrylate, hexyl acrylate, 2-ethylhexyl acrylate, octyl acrylate, tert-octyl acrylate, 2-chloroethyl acrylate, 2-bromoethyl acrylate, 4-chlorobutyl acrylate, cyanoethyl acrylate, 2-acetoxyethyl acrylate, dimethylaminoethyl acrylate, benzyl acrylate, methoxybenzyl acrylate, 2-chlorocyclohexyl acrylate, cyclohexyl acrylate, furfuryl acrylate, tetrahydrofurfuryl acrylate, phenyl acrylate, 5-hydroxypentyl acrylate, 2-methoxyethyl acrylate, 3-methoxybutyl acrylate, 2-ethoxybutyl acrylate, 2-ethoxyethyl acrylate, 2-isopropoxy acrylate, 2-butoxyethyl acrylate, 2-(2-methoxyethoxy)ethyl acrylate, 2-(2-methoxyethoxy)ethyl acrylate, 2-(2-butoxyethoxy) ethyl acrylate, ω-methoxypolyethylene glycol acrylate (addition mol number: 9), 1-bromo-2-methoxyethyl acrylate, 1,1-dichloro-2-ethoxyethyl acrylate, or a mixture thereof.

In addition, the following monomers can be used. Methacrylic esters, specifically, e.g., methyl methacrylate, ethyl methacrylate, n-propyl methacrylate, isopropyl methacrylate, n-butyl methacrylate, isobutyl methacrylate, sec-butylmethacrylate, tert-butylmethacrylate, amylmethacrylate, hexylmethacrylate, cyclohexylmethacrylate, benzyl methacrylate, chlorobenzyl methacrylate, octyl methacrylate, stearylmethacrylate, sulfopropylmethacrylate, N-ethyl-N-phenylaminoethyl methacrylate, 2-(3-phenylpropyloxy) ethyl methacrylate, dimethylaminophenoxyethyl methacrylate, furfuryl methacrylate, tetrahydrofurfuryl methacrylate, phenyl methacrylate, cresyl methacrylate, naphthyl methacrylate, 2-hydroxyethyl methacrylate, 4-hydroxybutyl methacrylate, triethylene glycol monomethacrylate, dipropylene glycol monomethacrylate, 2-methoxyethyl methacrylate, 3-methoxybutyl methacrylate, 2-acetoxyethyl methacrylate, 2-acetoacetoxyethyl methacrylate, 2-ethoxyethyl methacrylate, 2-isopropoxyethyl methacrylate, 2-butoxyethyl methacrylate, 2-(2-methoxyethoxy)ethyl methacrylate, 2-(2-ethoxyethoxy)ethyl methacrylate, 2-(2-butoxyethoxy)ethyl methacrylate, ω-methoxypolyethylene glycol methacrylate (addition mol number: 6), acryl methacrylate, and methacrylic acid dimethylaminoethylmethyl chloride salt can be exemplified.

Vinylesters, specifically, e.g., vinylacetate, vinyl propionate, vinyl butyrate, vinyl isobutyrate, vinyl caproate, vinyl chloroacetate, vinylmethoxy acetate, vinylphenyl acetate, vinyl benzoate and vinyl salicylate can be exemplified.

Acrylamides, e.g., acrylamide, methylacrylamide, ethylacrylamide, propylacrylamide, isopropylacrylamide, n-butylacrylamide, sec-butylacrylamide, tert-butylacrylamide, cyclohexylacrylamide, benzylacrylamide, hydroxymethylacrylamide, methoxyethylacrylamide, dimethylaminoethylacrylamide, phenylacrylamide, dimethylacrylamide, diethylacrylamide, β-cyanoethylacrylamide, N-(2-acetoacetoxyethyl)acrylamide, and diacetoneacrylamide can be exemplified.

Methacrylamides, e.g., methacrylamide, methylmethacrylamide, ethylmethacrylamide, propylmethacrylamide, isopropylmethacrylamide, n-butylmethacrylamide, sec-butylmethacrylamide, tert-butylmethacrylamide, cyclohexylmethacrylamide, benzylmethacrylamide, hydroxymethacrylamide, chlorobenzylmethacrylamide, octylmethacrylamide, stearylmethacrylamide, sulfopropylmethacrylamide, N-ethyl-N-phenylaminoethylmethacrylamide, 2-(3-phenylpropyloxy)ethylmethacrylamide, dimethylaminophenoxyethylmethacrylamide, furfurylmethacrylamide, tetrahydrofurfurylmethacrylamide, phenylmethacrylamide, cresylmethacrylamide, naphthylmethacrylamide, 2-hydroxyethylmethacrylamide, 4-hydroxybutylmethacrylamide, triethylene glycol monomethacrylamide, dipropylene glycol monomethacrylamide, 2-methoxyethylmethacrylamide, 3-methoxybutylmethacrylamide, 2-acetoxyethylmethacrylamide, 2-acetoacetoxyethylmethacrylamide, 2-ethoxyethylmethacrylamide, 2-isopropoxyethylmethacrylamide, 2-butoxyethylmethacrylamide, 2-(2-methoxyethoxy) ethylmethacrylamide, 2-(2-ethoxyethoxy) ethylmethacrylamide, 2-(2-butoxyethoxy) ethylmethacrylamide, ω-methoxypolyethylene glycol methacrylamide (addition mol number: 6), acrylmethacrylamide, dimethylaminomethacrylamide, diethylaminomethacrylamide, B-cyanoethylmethacrylamide, and N-(2-acetoacetoxyethyl)methacrylamide can be exemplified.

Olefins, e.g., dicyclopentadiene, ethylene, propylene, 1-butene, 1-pentene, vinyl chloride, vinylidene chloride, isoprene, chloroprene, butadiene, and 2,3-dimethylbutadiene can be exemplified.

Styrenes, e.g., styrene, methylstyrene, dimethylstyrene, trimethylstyrene, ethylstyrene, isopropylstyrene, chloromethylstyrene, methoxystyrene, acetoxystyrene, chlorostyrene, dichlorostyrene, bromostyrene, and vinylbenzoic acid methyl ester can be exemplified.

Vinyl ethers, e.g., methylvinyl ether, butylvinyl ether, hexylvinyl ether, methoxyethylvinyl ether and dimethylaminoethylvinyl ether can be exemplified.

As other examples, e.g., butyl crotonate, hexyl crotonate, dibutyl itaconate, dimethyl maleate, dibutyl maleate, dimethyl fumarate, dibutyl fumarate, methyl vinyl ketone, phenyl vinyl ketone, methoxyethyl vinyl ketone, glycidyl acrylate, glycidyl methacrylate, N-vinyloxazolidone, N-vinylpyrrolidone, acrylonitrile, methacrylonitrile, methylene moronnitrile, and vinylidene can be exemplified.

Two or more monomers may be used as co-monomers with each other according to purposes (e.g., improvement of hardness, flexibility, tensile strength and light fastness), thereby producing co-polymers.

Herein a compound of Formula (I), (I-A), (I-B), (I-C) or (I-D) may have an absorbance in a range of about 600 nm to about 800 nm in a UV/visible (UV/vis) spectrum. For example an absorbance in a range of: about 620 nm to about 800 nm; about 640 nm to about 800 nm; about 660 nm to about 800 nm; about 680 nm to about 800 nm; about 700 nm to about 800 nm; about 720 nm to about 800 nm; about 740 nm to about 800 nm; about 760 nm to about 800 nm; about 780 nm to about 800 nm; about 600 nm to about 780 nm; about 600 nm to about 760 nm; about 600 nm to about 740 nm; about 600 nm to about 720 nm; about 600 nm to about 700 nm; about 600 nm to about 680 nm; about 600 nm to about 660 nm; about 600 nm to about 640 nm; about or 600 nm to about 620 nm.

The UV/vis spectrum may be measured using appropriate equipment as known in the art, for example an ultraviolet-visible spectrophotometer.

Herein a compound of Formula (I), (I-A) and (I-B) may have a fluorescence maxima in a range of about 625 nm to about 900 nm. For example: about 650 nm to about 900 nm; 675 nm to about 900 nm; 700 nm to about 900 nm; 725 nm to about 900 nm; 750 nm to about 900 nm; 775 nm to about 900 nm; 800 nm to about 900 nm; 825 nm to about 900 nm; 850 nm to about 900 nm; 875 nm to about 900 nm; 625 nm to about 875 nm; 625 nm to about 850 nm; 625 nm to about 825 nm; 625 nm to about 800 nm; 625 nm to about 775 nm; 625 nm to about 750 nm; 625 nm to about 725 nm; 625 nm to about 700 nm; 625 nm to about 675 nm; or 625 nm to about 650 nm.

The fluorescence maxima may be measured using appropriate equipment as known in the art, for example a fluorescence spectrophotometer.

Solvents that could be used to dissolve the compounds for a spectroscopic analysis can include: methylene chloride, chloroform, toluene, halogenated toluenes, xylene, chlorinated benzenes, nitro benzene, dimethyl sulphoxide, diethyl formamide, dimethyl formamide and ethers.

Compositions

Disclosed herein are compositions which comprise a compound of Formula (I), (I-A), (I-B), (I-C), and/or (I-D).

Also disclosed herein are compositions which consist essentially of Formula (I), (I-A), (I-B), (I-C), and/or (I-D).

In one embodiment the composition comprises a compound of Formula (I).

In one embodiment the composition comprises a compound of Formula (I-A). In another embodiment the composition comprises a compound of Formula (I-A1). In yet another embodiment the composition comprises a compound of Formula (I-A2).

In one embodiment the composition comprises a compound of Formula (I-B). In another embodiment the composition comprises a compound of Formula (I-B1). In yet another embodiment the composition comprises a compound of Formula (I-B2).

In one embodiment the composition comprises a compound of Formula (I-C). In another embodiment the composition comprises a compound of Formula (I-C1). In yet another embodiment the composition comprises a compound of Formula (I-C2).

In one embodiment the composition comprises a compound of Formula (I-D). In another embodiment the composition comprises a compound of Formula (I-D1). In yet another embodiment the composition comprises a compound of Formula (I-D2).

The composition may be a dye composition. For example the starting dibromo dianhydride may be reacted with 2 different o-aryl diamines or an alkyl amine mixed with an o-aryl amine to form a statistical mixtures of variously functionalised 3,4 and 9,10 carboxy groups. This mixtures can then be further reacted with one or more different types of phenols to further differentiate the products to form a varied mixture of dyes. This mixture may be used directly as a dye composition.

In one embodiment, a compound of Formula (I), (I-A), (I-B), (I-C) or (I-D) comprises the core of a multi-chromophore array wherein 2 other dyes bearing phenolic groups are reacted with the dibromo diaryl imidazole starting material to form a trimer where the other dyes groups are appended to the 2 bay positions of the core perylene. Alternatively the phenol bearing chromophore is reacted with only one bay position of the patent dye and the second bromo group is then reacted with a different phenol. The second phenolic group may or may not be chromophoric.

In another embodiment, a compound of Formula (I), (I-A), (I-B), (I-C) or (I-D) may be used in conjunction with at least one other compound, for example a compound comprising a perylene core, to form a multi-chromophore complex. Examples of the at least one other compound include, but are not limited to, the compounds disclosed in WO 2015/024064 A1; *ChemPhysChem*, 2011, 12, 595-608; *J. AM. CHEM. SOC.*, 2004, 126, 8284-8294; *Eur. J. Org. Chem.*, 2008, 4559-4562; *J. Mater. Chem.*, 2010, 20, 3814-3826; *Angew Chem Int Ed*, 2002, 41(11), 1900; and *Chem. Eur. J.*, 2004, 10, 1398-1414, the content of each is incorporated by reference.

Methods of Synthesis

Disclosed herein are methods of synthesising a compound of Formula (I), (I-A), (I-B), (I-C) and/or (I-D).

Herein, a compound of Formula (I), (I-A), (I-B), (I-C) or (I-D) may be synthesised by a method that comprises the step of contacting a compound of Formula (II)

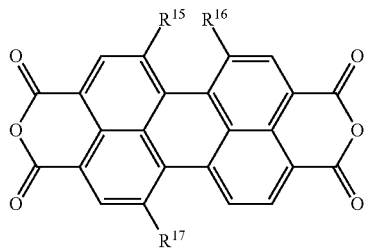

Formula (II)

wherein:
each of $R^{15}$, $R^{16}$ and $R^{17}$ is either:
independently selected from hydrogen or

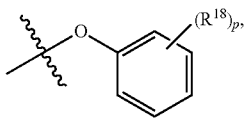

with the proviso that two of $R^{15}$, $R^{16}$ and $R^{17}$ are

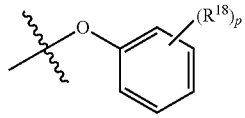

and the other is hydrogen; or
independently selected from hydrogen, bromine or chlorine, with the proviso that two of $R^{15}$, $R^{16}$ and $R^{17}$ are either bromine or chlorine, and the other is hydrogen;
each $R^{18}$ is selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene, or a mixture thereof, each of which optionally comprises one or more substituents; and
p is an integer selected from 0, 1, 2, 3, 4 or 5,
with a compound of Formula (III):

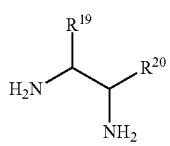

Formula (III)

wherein $R^{19}$ and $R^{20}$ are: joined to form an optionally substituted monocyclic aromatic ring; or joined to form optionally substituted polycyclic aromatic group.

For compounds of Formula (II), two of $R^{15}$, $R^{16}$ and $R^{17}$ may be

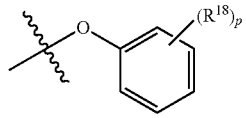

and the remaining group is hydrogen.

$R^{15}$ and $R^{17}$ may both be

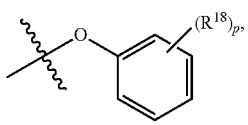

whilst $R^{16}$ is hydrogen. Alternatively, $R^{17}$ and $R^{18}$ may both be

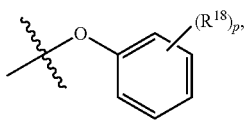

whilst $R^{15}$ is hydrogen.

Each $R^{18}$ group may be an optionally substituted: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido) alkyl, mercaptoalkyl, (heterocyclo)alkyl, (cycloalkylamino) alkyl, ($C_1$-$C_4$ haloalkoxy)alkyl, (heteroaryl)alkyl, or perylene, or a mixture thereof. For example, $R^{18}$ may be an optionally substituted $C_1$-$C_{12}$ branched or straight chain alkyl group. $R^{18}$ may be an optionally substituted tert-butyl group or a $C_{12}$ straight chain alkyl group.

In one embodiment, in compounds of Formula (II), two of $R^{15}$, $R^{16}$ and $R^{17}$ may be bromine and the remaining group is hydrogen.

$R^{15}$ and $R^{17}$ may both be bromine, whilst $R^{16}$ is hydrogen. Alternatively, $R^{16}$ and $R^{17}$ may both be bromine, whilst $R^{15}$ is hydrogen.

In one embodiment, in compounds of Formula (II), two of $R^{15}$, $R^{16}$ and $R^{17}$ may be chlorine and the remaining group is hydrogen.

$R^{15}$ and $R^{17}$ may both be chlorine, whilst $R^{16}$ is hydrogen. Alternatively, $R^{16}$ and $R^{17}$ may both be chlorine, whilst $R^{15}$ is hydrogen.

In one embodiment $R^{18}$ is an optionally substituted alkyl group.

In addition, each $R^{18}$ may be selected from, but not limited to an optionally substituted appended: aryl, heteroaryl, pyridine, bipyridine, terpyridine or phenanthroline group. Each $R^{18}$ may be selected from:

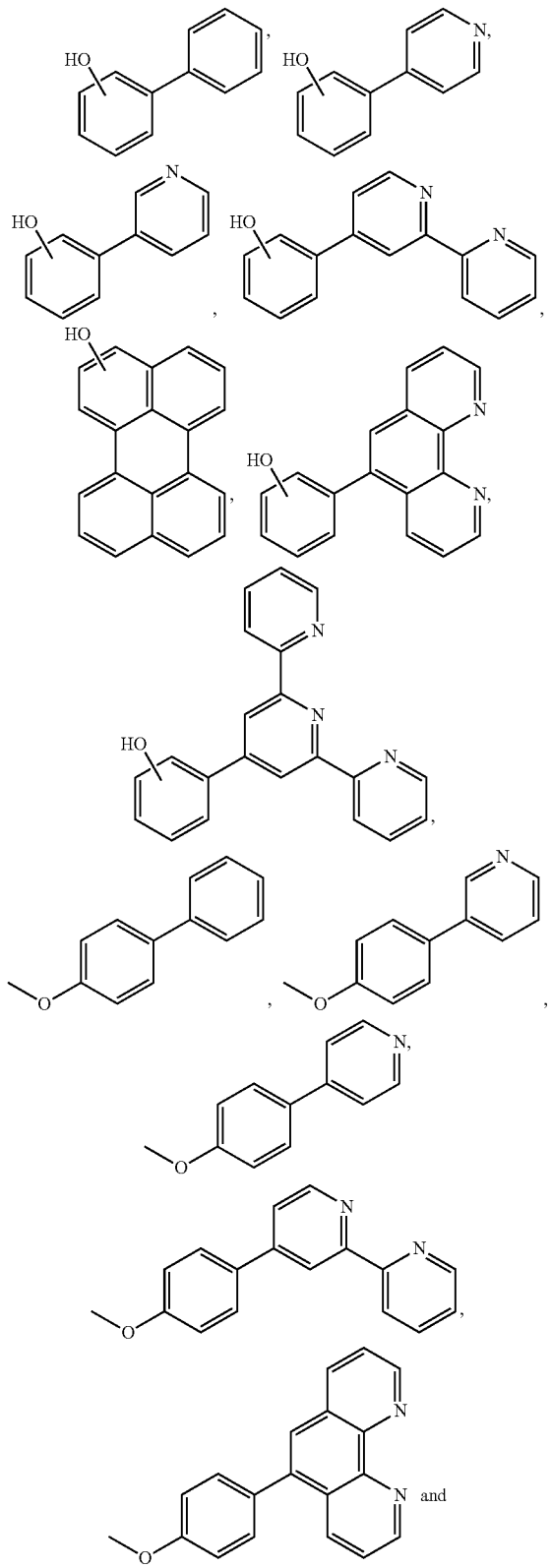

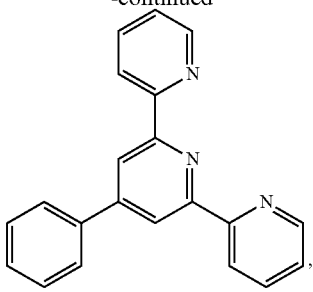

wherein $R^{18}$ may be attached at any carbon on an aryl ring in the aforementioned structures.

In one embodiment $R^{18}$ is an optionally substituted alkyl group.

In another embodiment $R^{18}$ is an optionally substituted perylene. Examples of optionally substituted perylenes include those disclosed in WO 2015/024064 A1; *ChemPhysChem*, 2011, 12, 595-608; *J. AM. CHEM. SOC.*, 2004, 126, 8284-8294; *Eur. J. Org. Chem.*, 2008, 4559-4562; *J. Mater. Chem.*, 2010, 20, 3814-3826; *Angew Chem Int Ed*, 2002, 41(11), 1900; and *Chem. Eur. J.*, 2004, 10, 1398-1414, the content of each is incorporated by reference.

Integer "p" may be selected from 0, 1, 2, 3, 4 or 5. In one embodiment p is 0. In another embodiment p is 1. In yet another embodiment p is 2.

When p is 2 or greater, each $R^{18}$ group may be the same of different.

In one embodiment $R^{19}$ and $R^{20}$ are joined to form an optionally substituted monocyclic aromatic ring. In another embodiment $R^{19}$ and $R^{20}$ are joined to form an optionally substituted polycyclic aromatic group. In another embodiment $R^{19}$ and $R^{20}$ form a monocyclic aromatic ring which is unsubstituted. In another embodiment $R^{19}$ and $R^{20}$ form a polycyclic aromatic group which is unsubstituted. In another embodiment $R^{19}$ and $R^{20}$ form a monocyclic aromatic ring which is substituted. In yet another embodiment $R^{19}$ and $R^{20}$ form a polycyclic aromatic group which is substituted.

In another embodiment the polycyclic aromatic group consists of 2, 3, 4, 5 or 6 fused ring systems, wherein each ring is optionally substituted.

Examples of monocyclic aromatic rings and polycyclic aromatic rings which may optionally be substituted includes, but is not limited to: phenyl, naphthalene, anthracene, phenanthrene, tetracene, chrysene, triphenylene, pyrene, pentacene, benzo[a]pyrene, and dibenz[a,h]anthracene rings, or mixtures thereof.

In one embodiment, a compound of Formula (III) is selected from the group consisting of optionally substituted:

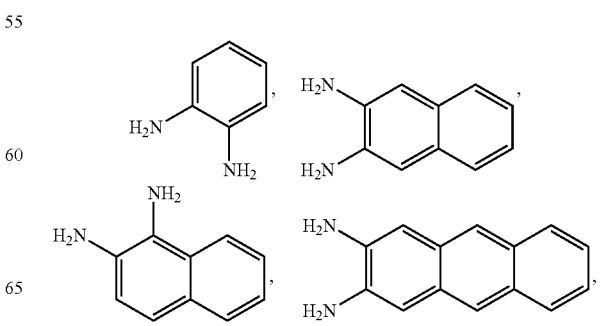

-continued
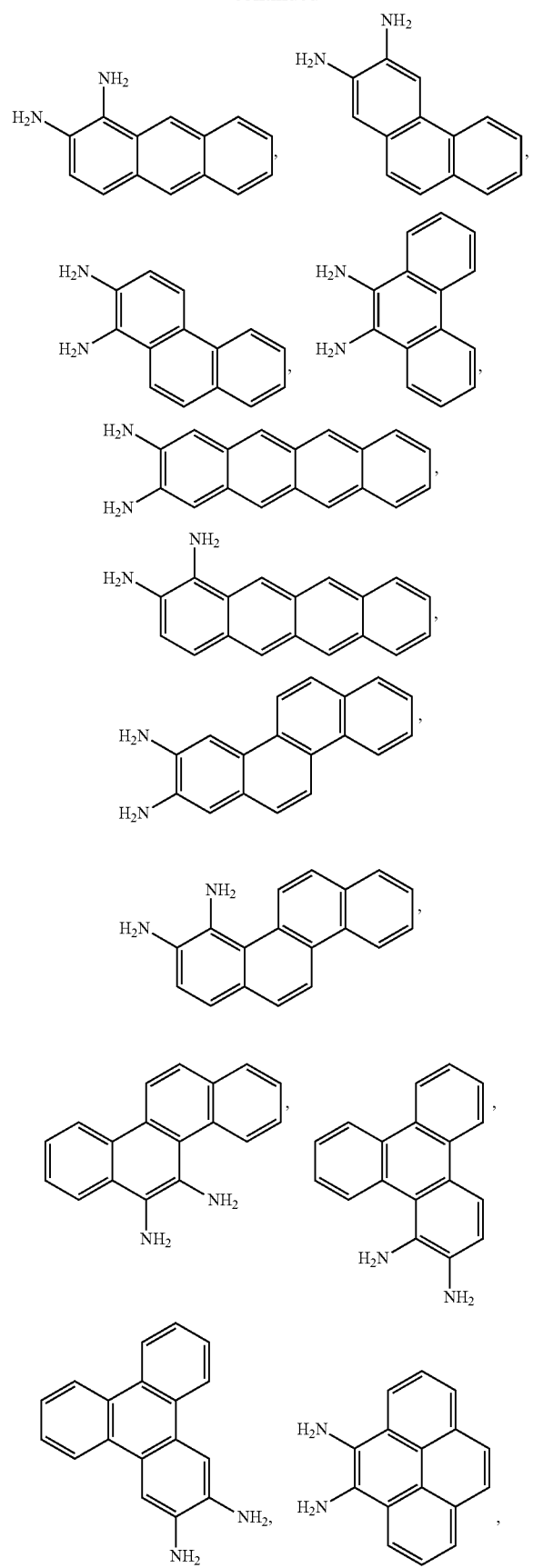
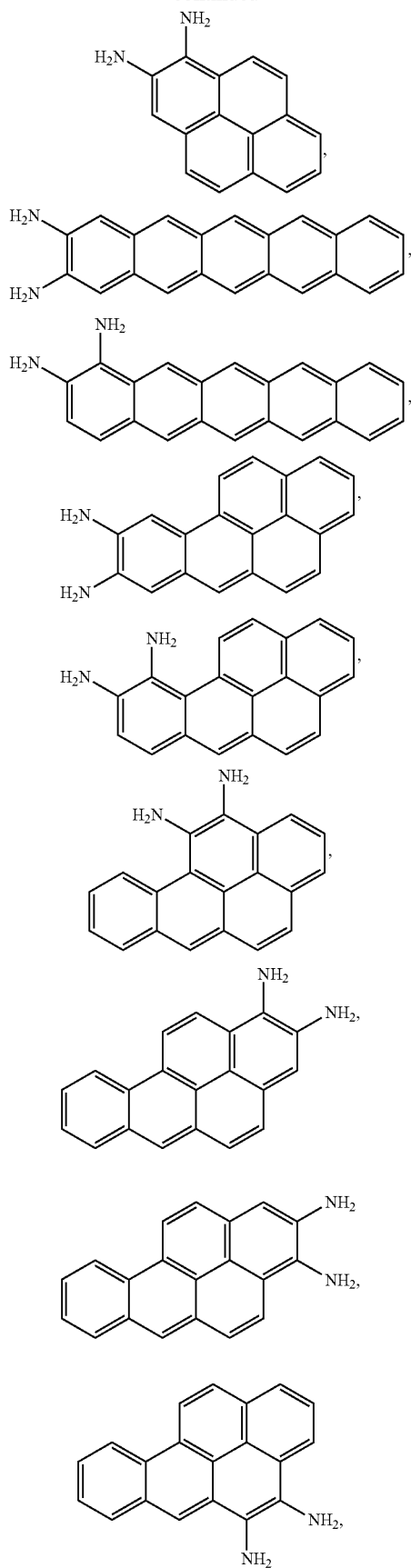

-continued
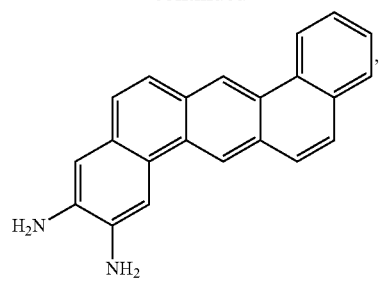
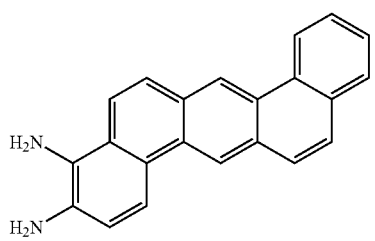
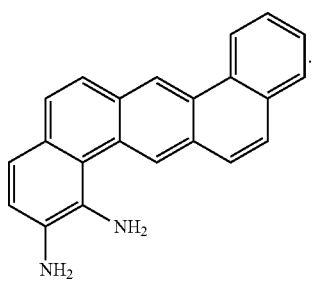
In one embodiment, a compound of Formula (III) is selected from the group consisting of optionally substituted:
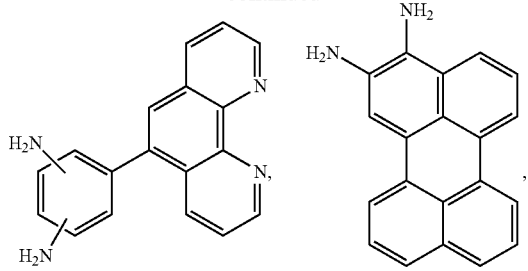
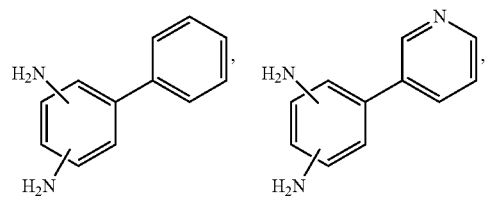
-continued
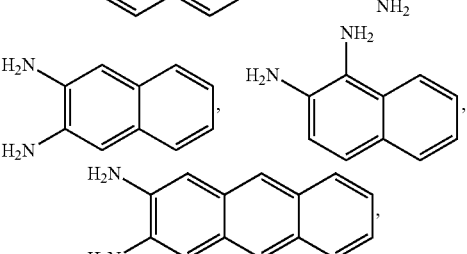
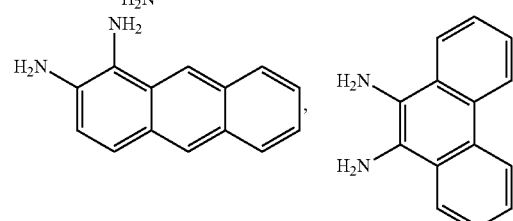
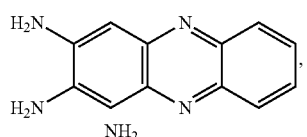
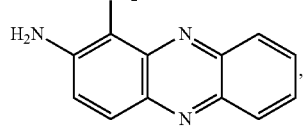
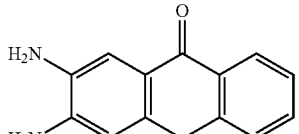
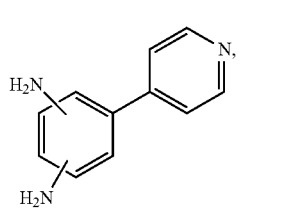
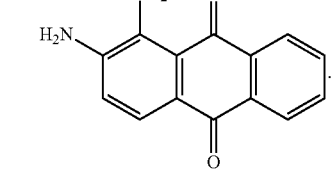
In one embodiment, the compound of Formula III is selected from: o-phenylene diamine, 2,3 diamino naphthalene, 1,2 diamino naphthalene, or 2,3 diamino anthroquinone.

In another embodiment, the resulting product of a compound of Formula (II) and a compound of Formula (III) may be reacted with appropriate alcohols to yield a compound of Formula (I).

Also disclosed herein is a compound produced by a method as described herein.

REFERENCES

1. Maki, T.; Hashimoto, H., *Kogyo Kagaku Zasshi* 1951, 54, 479.
2. Maki, T.; Hashimoto, H., *Kogyo Kagaku Zasshi* 1951, 54, 544.
3. Maki, T.; Hashimoto, H., *Bull Chem. Soc. Jpn* 1952, 25.
4. Maki, T.; Hashimoto, H., *Bull. Chem. Soc. Jpn* 1954, 27.
5. Tang, C. W., Two-layer organic photovoltaic cell. *Applied Physics Letters* 1986, 48 (2), 183-185.
6. Halls, J.; Friend, R., The photovoltaic effect in a poly (p-phenylenevinylene)/perylene heterojunction. *Synthetic Metals* 1997, 85 (1), 1307-1308.
7. Lane, P.; Rostalski, J.; Giebeler, C.; Martin, S.; Bradley, D.; Meissner, D., Electroabsorption studies of phthalocyanine/perylene solar cells. *Solar energy materials and solar cells* 2000, 63 (1), 3-13.
8. Tsuzuki, T.; Shirota, Y.; Rostalski, J.; Meissner, D., The effect of fullerene doping on photoelectric conversion using titanyl phthalocyanine and a perylene pigment. *Solar Energy Materials and Solar Cells* 2000, 61 (1), 1-8.
9. Breeze, A.; Salomon, A.; Ginley, D.; Gregg, B.; Tillmann, H.; Hörhold, H.-H., Polymer-perylene diimide heterojunction solar cells. *Applied physics letters* 2002, 81 (16), 3085-3087.
10. Quante, H.; Geerts, Y.; Müllen, K., Synthesis of soluble perylenebisamidine derivatives. Novel long-wavelength absorbing and fluorescent dyes. *Chemistry of materials* 1997, 9 (2), 495-500.
11. Seybold, G.; Wagenblast, G., New perylene and violanthrone dyestuffs for fluorescent collectors. *Dyes and Pigments* 1989, 11 (4), 303-317.
12. Sun, B.; Zhao, Y.; Qiu, X.; Han, C.; Yu, Y.; Shi, Z., Substitution Effect of 1,7-Asymmetrically Substituted 3,4:9,10-Perylenebis(dicarboximide) Dyes. *Supramol. Chem.* 2008, 20 (6), 537-544.

Examples

Materials

Perylene 3,4:9,10 tetracarboxylic bis anhydride (128-69-8), 4-tertbutyl phenol (CAS: 98-54-4), 4-dodecyl phenol (mixture of isomers; CAS: 27193-86-8), 1,2-diamino benzene (CAS: 95-54-5), 1,2 diamino anthroquinone (CAS: 1758-68-5) were purchased from Sigma Aldrich and used without further purification. Reagent grade dimethylformamide (DMF) was subjected to high vacuum while stirring at room temperature to extract free dimethyl amine and moisture directly before use.

1,7 & 1,6 Dibromoperylene-3,4:9,10-tetracarboxylic Acid Bisanhydride

A mixture of 1,7 & 1,6 dibromoperylene-3,4:9,10-tetracarboxylic acid bisanhydride (Scheme 1), was generated by bromination of perylene 3,4:9,10 tetracarboxylic bis anhydride according to a literature procedure (J. Org. Chem. 2004, 69, 7933-7939).

A mixture of 100 g of perylene-3,4:9,10-tetracarboxylic acid bisanhydride (Compound 1) and 1.5 kg of 100 wt % sulfuric acid was stirred for 12 hours at room temperature, and subsequently $I_2$ (2.5 g) was added. The reaction mixture was heated to 85° C., and 90 g of bromine was added dropwise over a time period of 8 hours down a large, water-cooled condenser. After bromine addition, the reaction mixture was heated for an additional 10 hours at 85° C. HBr gas formed during the reaction was vented from the top of the condenser by a gentle stream of $N_2$ gas into a 500 mL aqueous quenching solution of w/w 5% NaOH, 0.05% $Na_2S_2O_5$. The reaction was cooled to room temperature and excess bromine was removed by bubbling the reaction with $N_2$ gas into the quenching solution. 65 mL of water was added carefully to precipitate the product. The resulting precipitate was separated by filtration through a G4 funnel, washed with 3×300 g of 86% sulfuric acid followed by a large amount of water. The product was dried in a vacuum to give 135 g (96%) of an isomeric mixture of 1,7 & 1,6 dibromoperylene-3,4:9,10-tetracarboxylic acid bisanhydride as a red powder. The crude product could not be purified since it is insoluble in organic solvents and was used without further purification.

Scheme 1

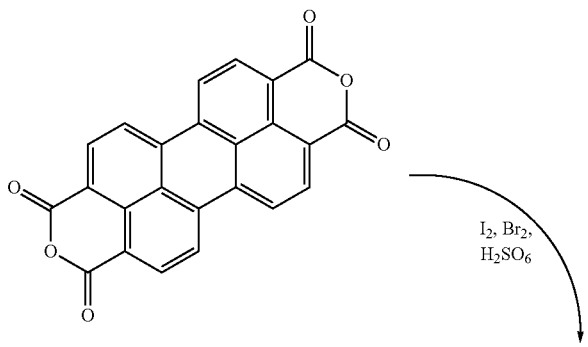

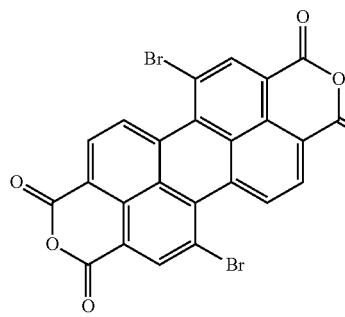
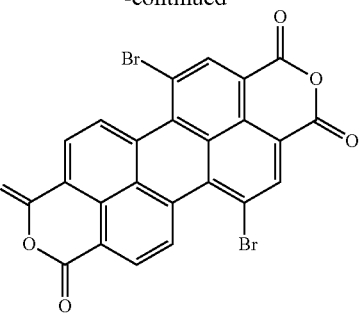
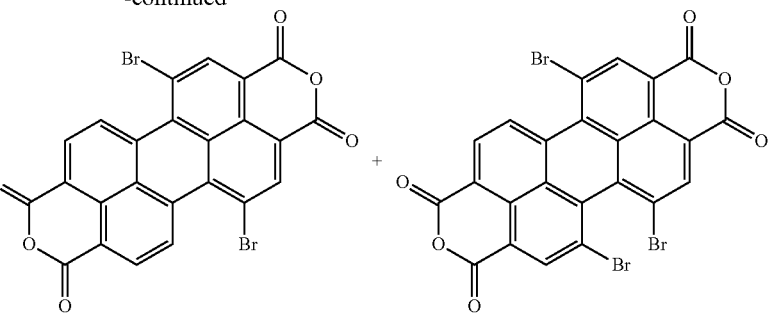

The literature has shown that the trans and cis isomers, typically in an 8:2 ratio, along with trace amounts of 1,6,7 tribromoperylene-3,4:9,10-tetracarboxylic acid bisanhydride (>2%) are formed in this procedure. These isomers generally persist in the same ratios in the dyes derived from them described herein.

3,4:9,10-Bis(1',2'-benzimidazole)-1,7 & 1,6 Dibromoperylene 3,4:9,10-bis(1',2'-benzimidazole)-1,7 & 1,6 dibromoperylene (Compound 2) was formed by taking 40 g of Compound 1 (36 mmol) and 16 grams of $Zn(OAc)_2 \cdot H_2O$ were dispersed in 350 mL of a stirring 1:1 v/v mixture of n-butanol and propionic acid. 10 g of o-phenylene diamine was added and the reaction was brought to reflux under $N_2$. The reaction continued for 6 hours and was then allowed to cool to room temperature. The resulting slurry was filtered directly, then washed with 300 mL of a 9:1 MeOH:water (v/v) mixture. The solid cake was then washed with multiple portions of hot water, followed by 1% 2M HCl in acetone washings (3×200 mL) that extracted light brown fractions of excess o-phenylene diamine. Finally, two more washings with MeOH:water mixture followed by drying under vacuum afforded 43 g of a dark purple powder, with a yield of 86%. MS (MALDI) calc. for $C_{36}Br_2H_{14}N_4O_2$ 694.33, found 694.27 UV/vis in $CHCl_3$, nm (log 10ε): 598 (5.68), 558 nm (5.61), 378 nm (5.13), Fluorescence max in $CHCl_3$: 646 nm.

Scheme 2 shows the trans isomer. Trans and cis dibromo species are formed along with the possible anti and syn isomers for the benzimidazole groups. In total there are four possible isomers, as well as trace amounts of the tribromo species.

Figure 4:
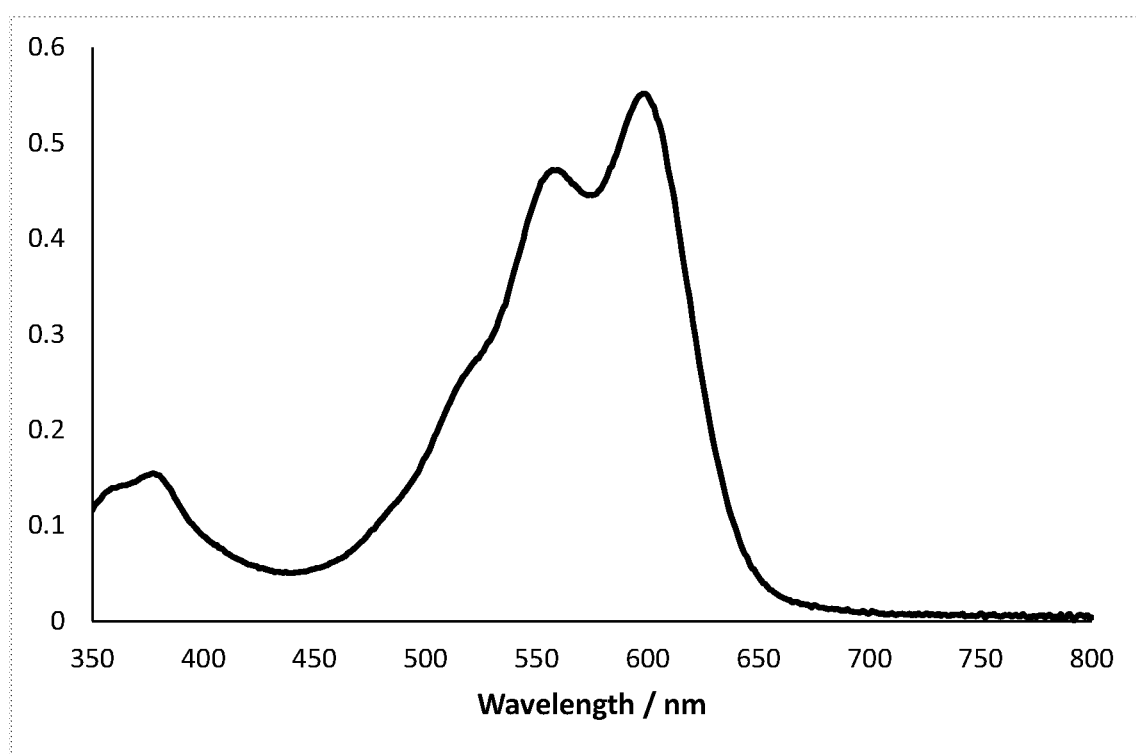
Figure 5:
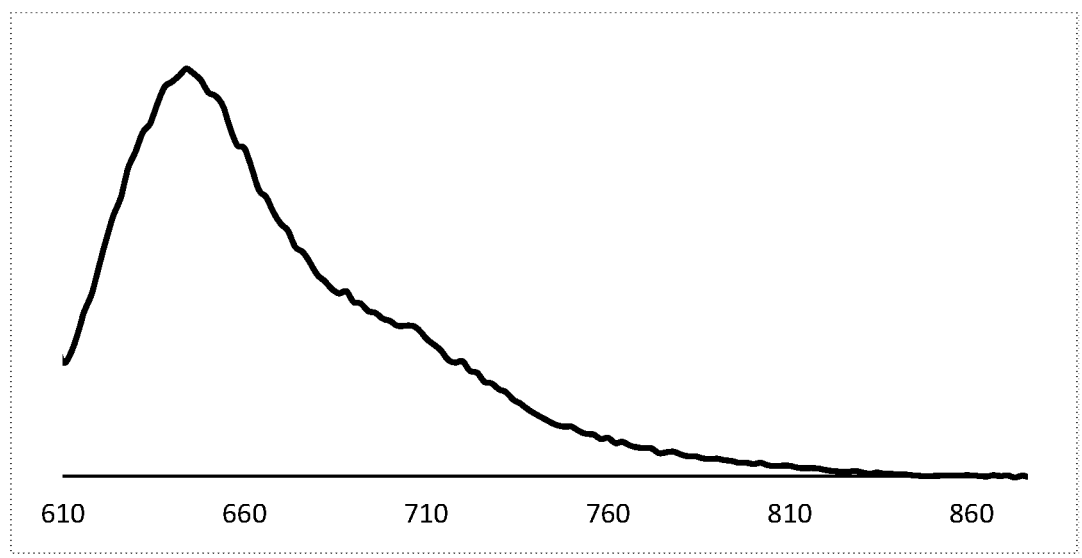
FIG. 5—UV/vis florescence spectra for Compound 2.

The UV/vis absorbance and florescence spectra for Compound 2 are shown in FIG. 4 and FIG. 5, respectively.

Scheme 2

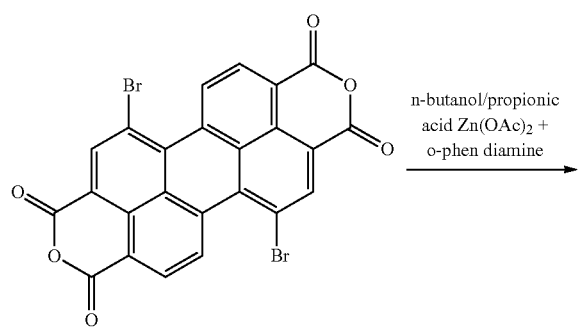

n-butanol/propionic acid $Zn(OAc)_2$ + o-phen diamine →

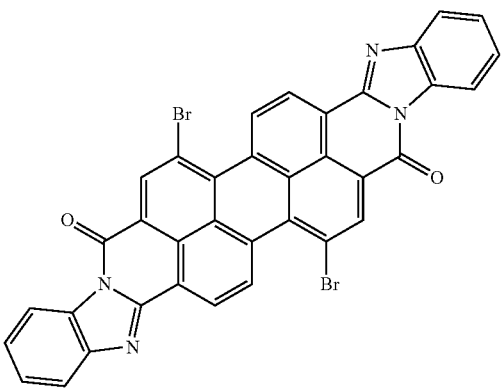

Figure 6:
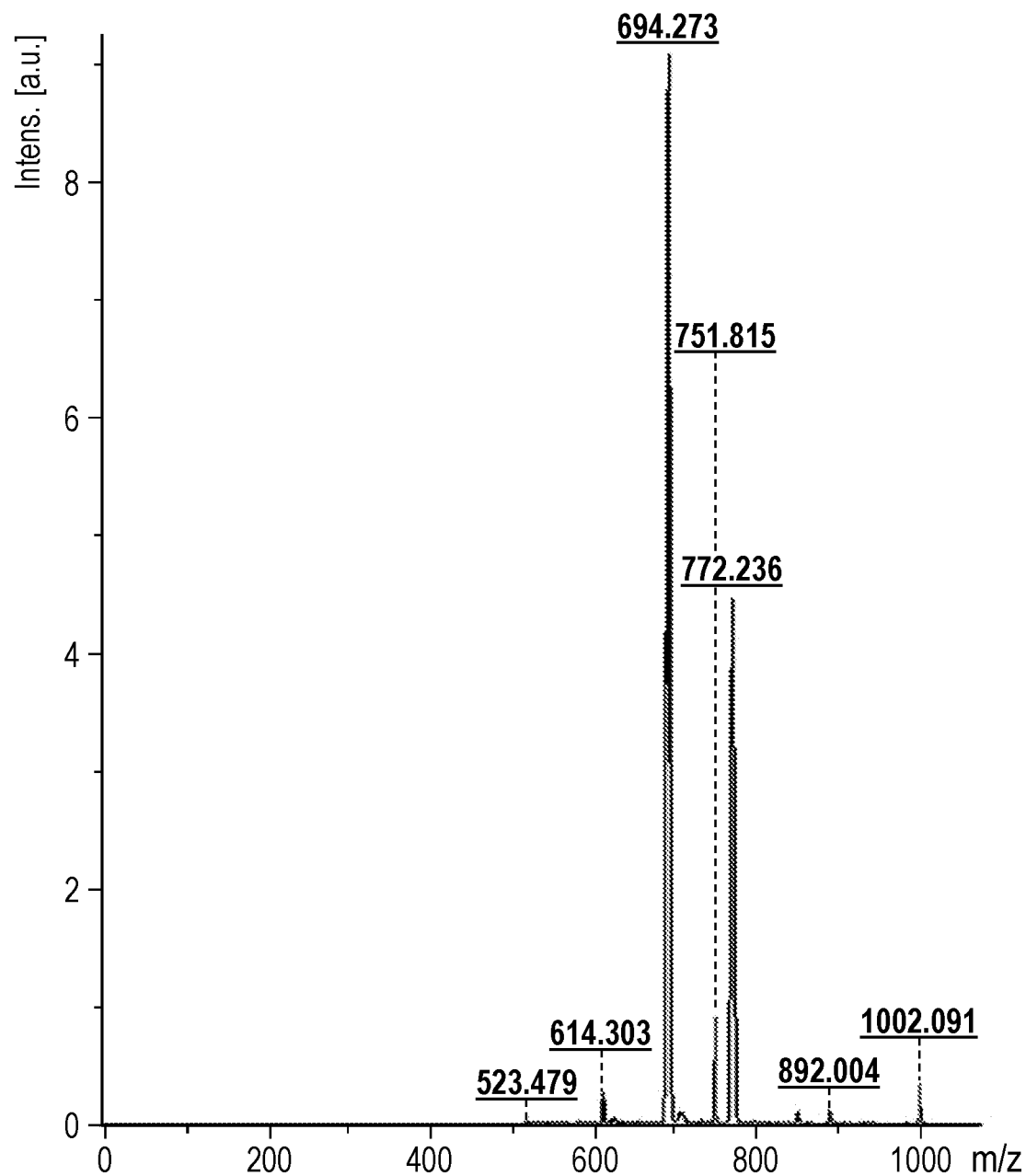
FIG. 6—A MALDI TOF MS spectrum of Compound 2.
Figure 7:
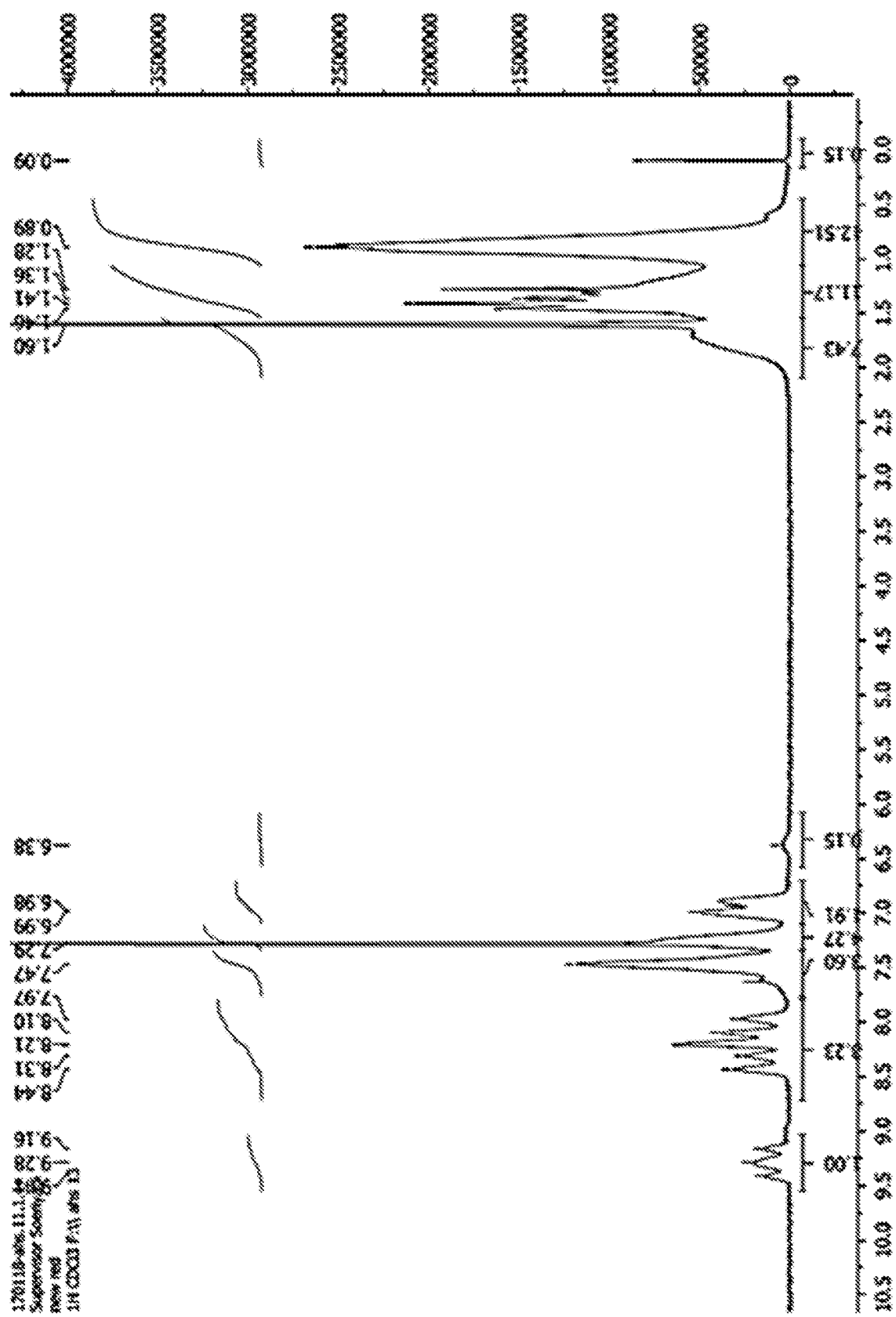
FIG. 7—$^1$H NMR characterisation of Compound 3.
Figure 8:
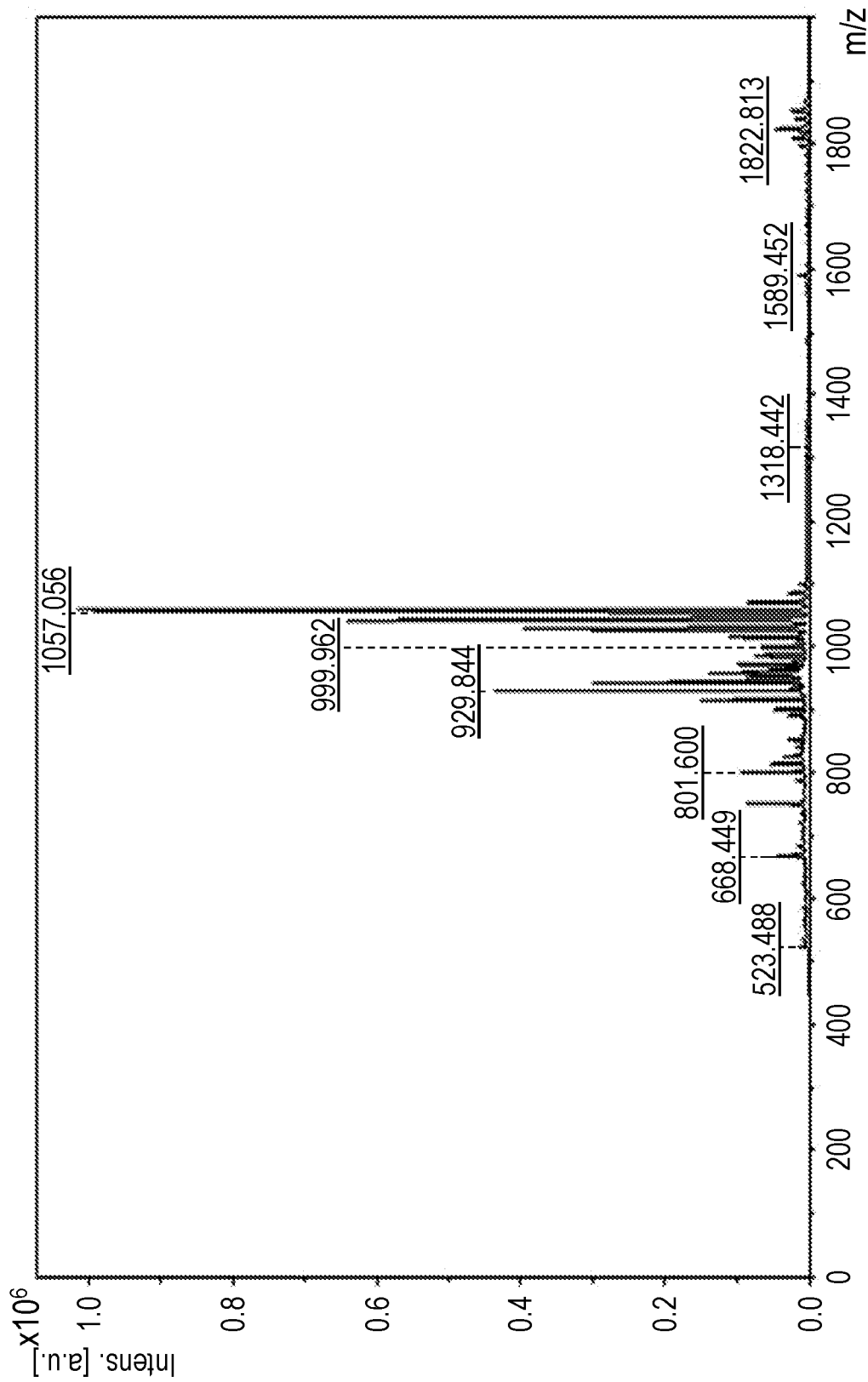
FIG. 8—MALDI TOF MS characterisation of Compound 3.
Figure 9:
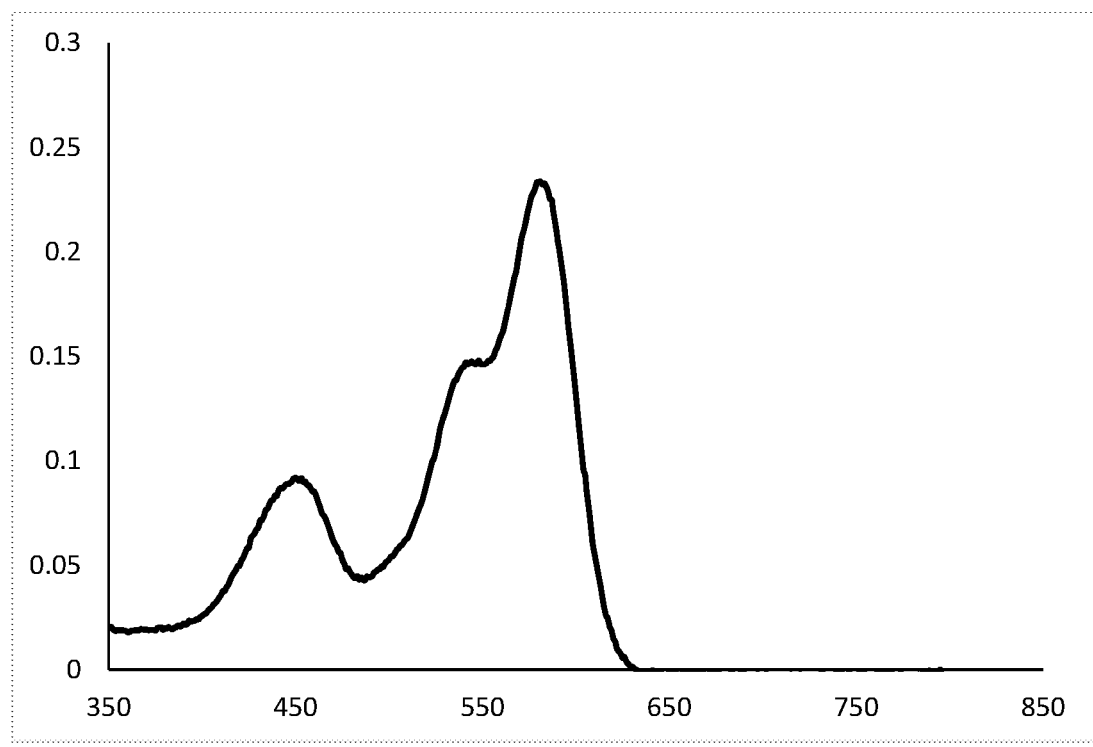
FIG. 9—UV/vis absorbance characterisation of Compound 3.
Figure 10:
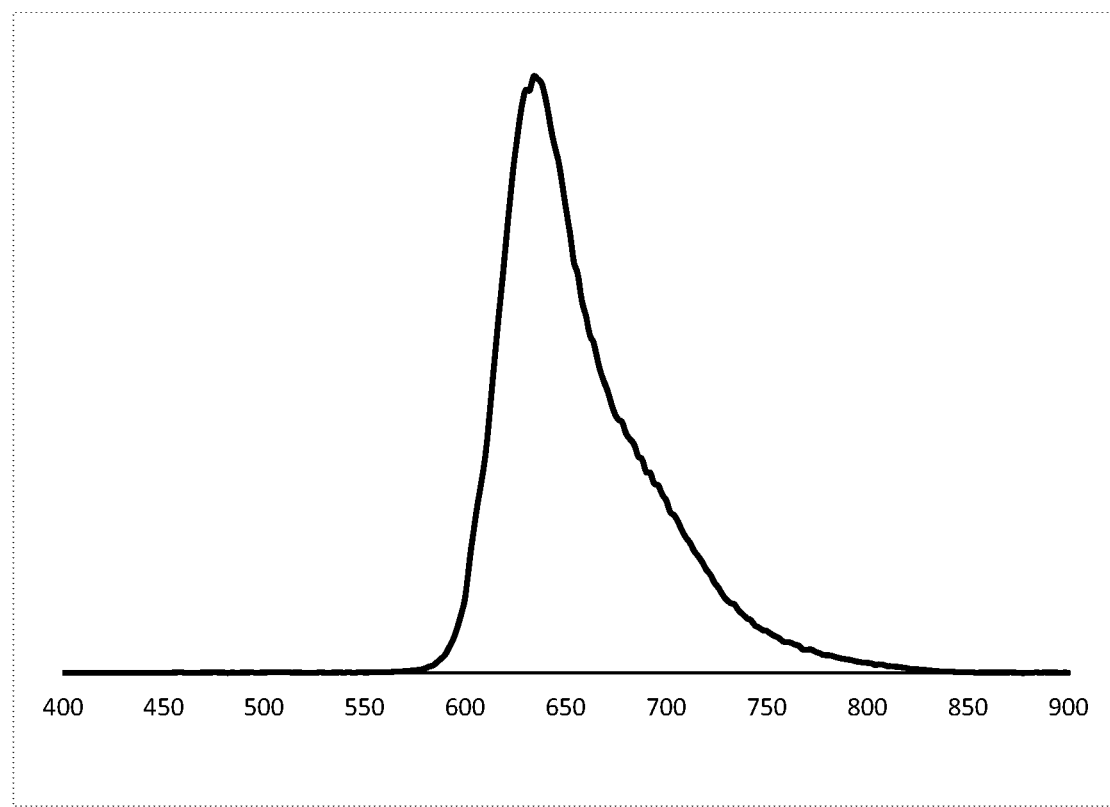
FIG. 10—UV/vis fluorescence characterisation of Compound 3.

FIG. 6 shows a MALDI spectrum of Compound 2. The peak at 772.236 shows the tribromo species that was not isolated.

3,4:9,10-Bis(1',2'-benzimidazole)-1,7 & 1,6 Bis (4"-dodecyl) phenoxy Perylenes 3,4:9,10-Bis(1',2'-benzimidazole)-1,7 & 1,6 Bis (4"-dodecyl) phenoxy perylenes (Compound 3) was formed by taking 56.6 g of 4-dodecyl phenol (mixture of isomers) was poured into a 1 L round bottomed vessel and diluted with 600 mL of DMF. 30 g of Compound 2 (43.2 mmol) was added by funnel along with 30 g of $K_2CO_3$. The mixture was heated to 110° C. under $N_2$ for 6 hours and allowed to cool to room temperature. 600 mL of methanol was added and the mixture was filtered in a 500 mL Buchner funnel. The dark filtrate, composed largely of side products, was discarded. This was followed by another 2×200 mL of fresh methanol washings. The solid cake was then extracted with 1.5 L of boiling, distilled water. Finally, 3×200 mL washings with acetone removed some side materials. The remaining solid was dried under vacuum to afford 39.90 g of product, 88% yield. $^1H$ 300 Mz NMR ($CDCl_3$) δ=9.16-9.41 br (2H perylene), 7.97-8.44 br (4H perylene, 2H benzimidazole), 7.47 br (4H benzimidazole), 7.29 br (4H phenoxy overlap with $CHCl_3$), 6.98-6.99 (4H phenoxy), 0.89-1.41 br (50H, dodecyl) MS (MALDI) calc. for $C_{72}H_{72}N_4O_4$ 1057.37, found 1057.06 UV/vis in $CHCl_3$, nm (log 10ε): 606 (4.77), 567 nm (4.64), 378 nm (4.04), Fluorescence max in $CHCl_3$: 634 nm.

Scheme 3 only shows the anti, trans isomer.

Scheme 4 only shows the anti, trans isomer.

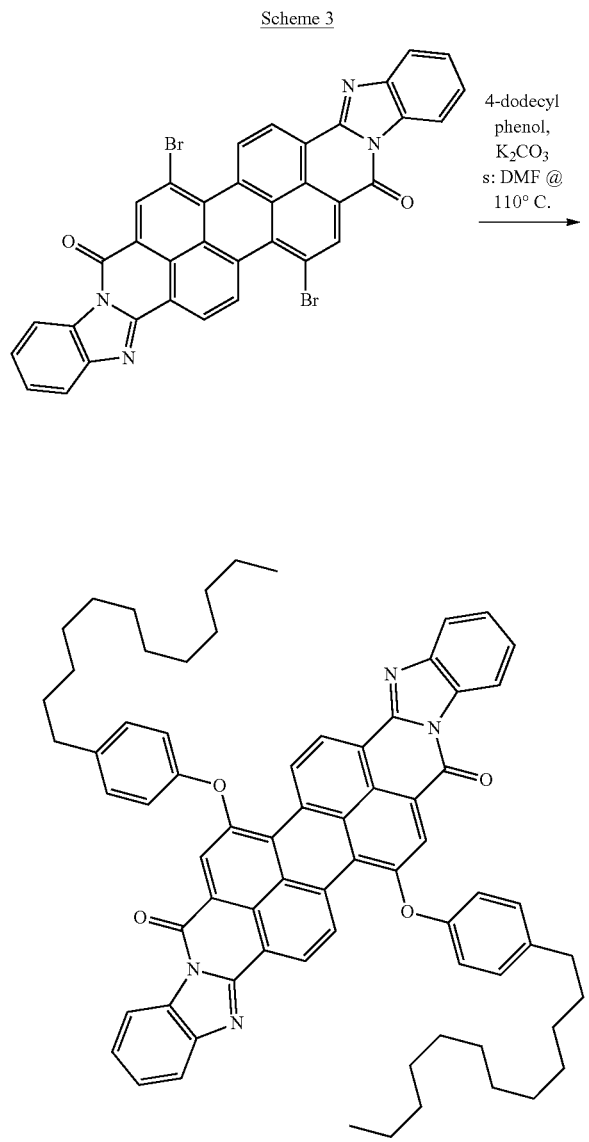

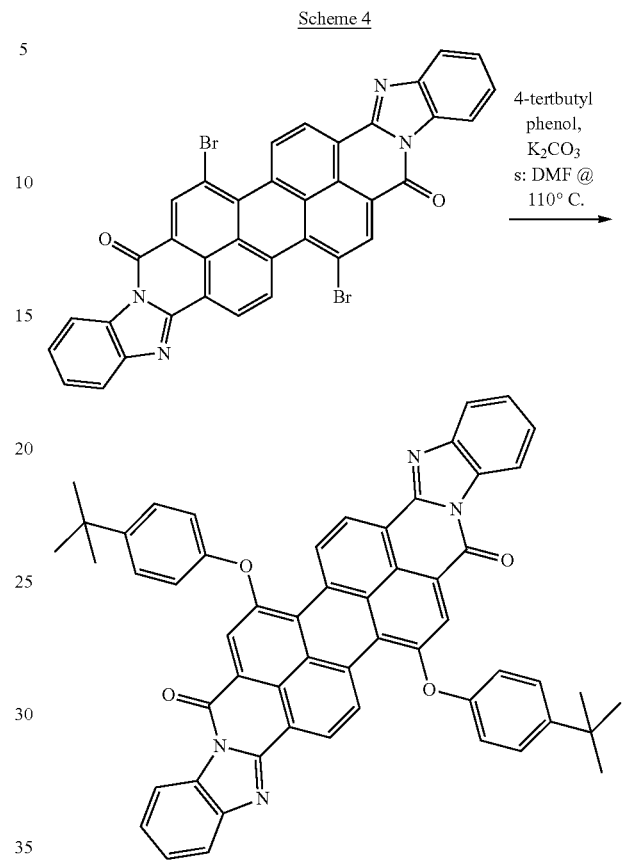

¹H NMR, MALDI, UV/vis absorbance and fluorescence characterisation of Compound 3 are shown in FIG. 7, FIG. 8, FIG. 9 and FIG. 10, respectively.

3,4:9,10-Bis(1',2'-benzimidazole)-1,7 & 1,6 Bis (4"-tertbutyl) phenoxy Perylenes 3,4:9,10-bis(1',2'-benzimidazole)-1,7 & 1,6 bis (4"-tert-butyl) phenoxy perylenes (Compound 4) were prepared in the same manner as compound III using 4-terbutyl phenol instead of 4-dodcecyl phenol. Owing to it reduced solubility, NMR spectra were not clear enough to provide reliable characterisation data. MS (MALDI) calc. for $C_{56}H_{40}N_4O_4$ 832.94, found 832. UV/vis in $CHCl_3$, nm (log 10ε): 606 (4.77), 567 nm (4.64), 378 nm (4.04), Fluorescence max in $CHCl_3$: 646 nm.

Figure 11:
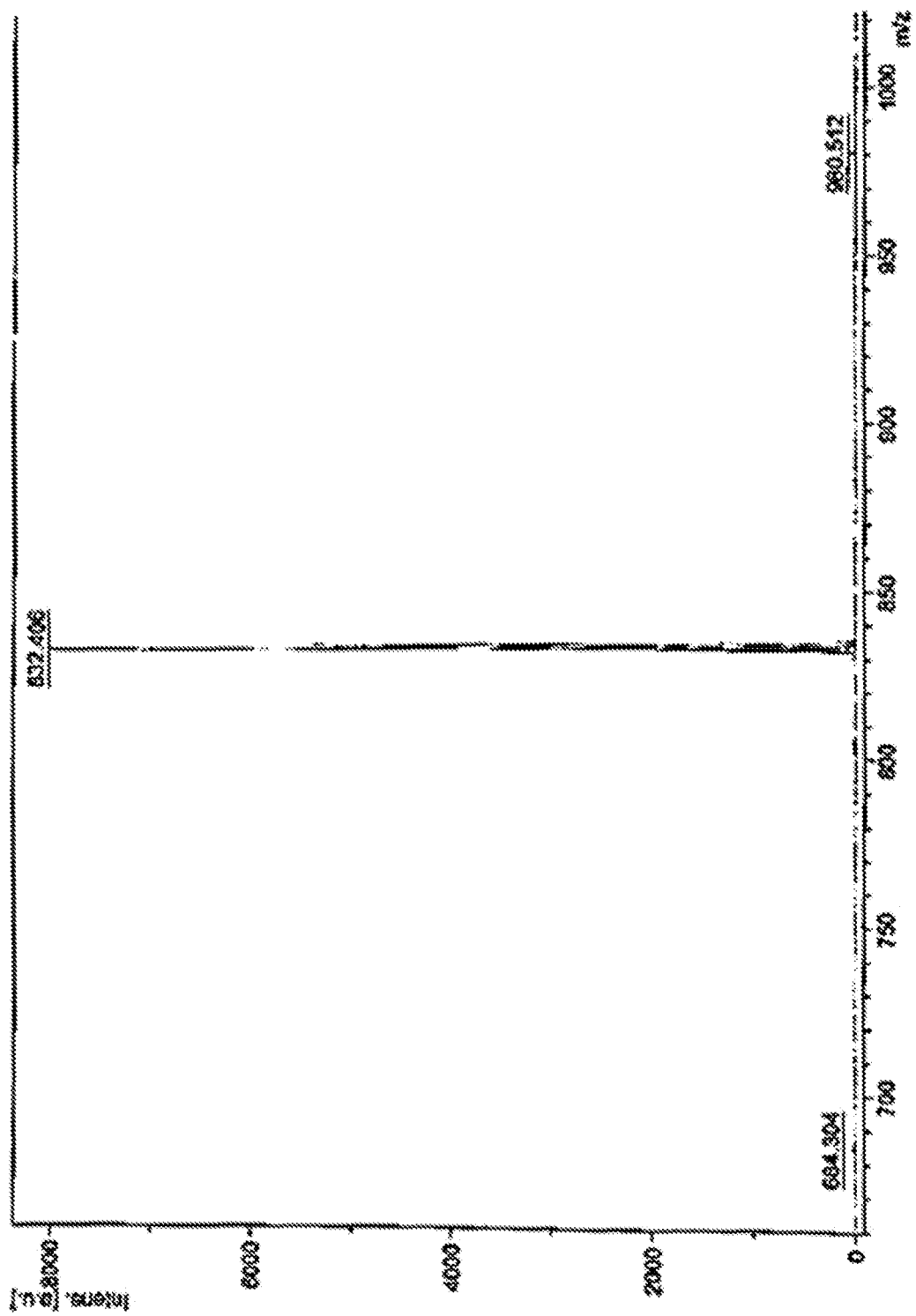
FIG. 11—MALDI TOF MS characterisation data for 3,4:9,10-bis(1',2'-benzimidazole)-1,7 & 1,6 bis (4"-tert-butyl) phenoxy peryle.
Figure 12:
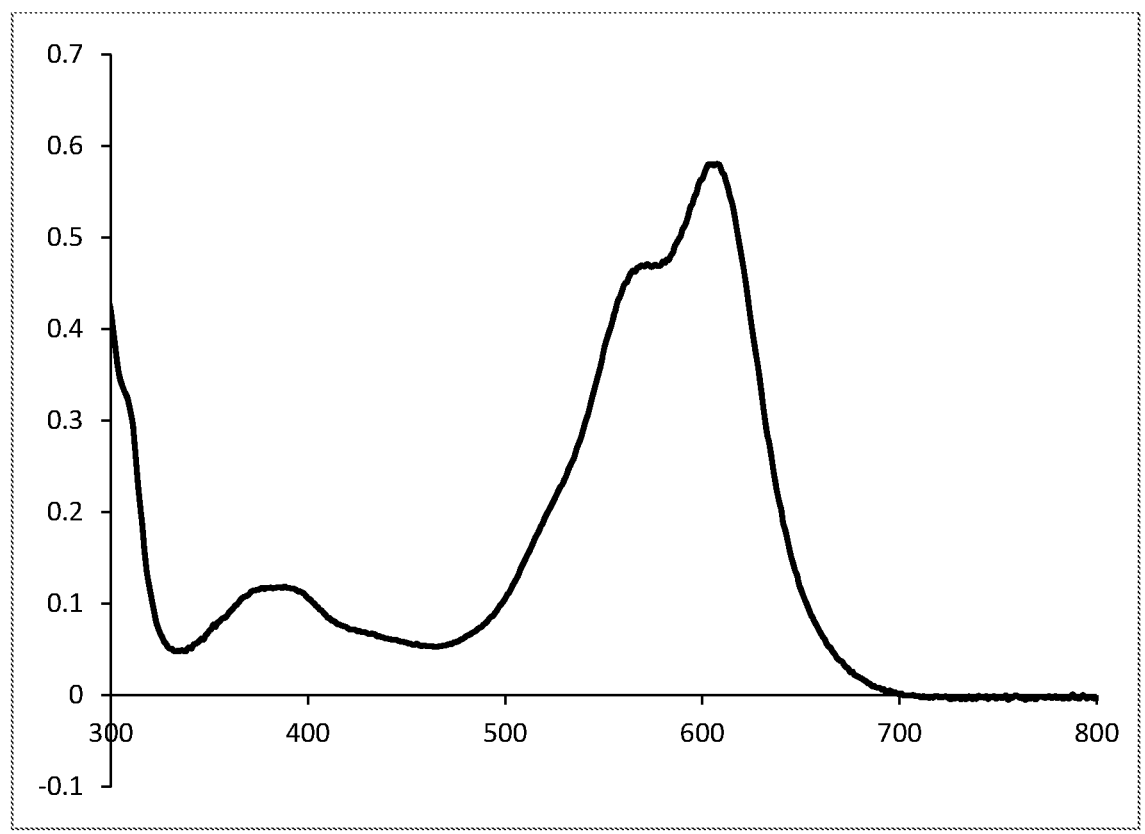
FIG. 12—UV/vis characterisation data for 3,4:9,10-bis(1', 2'-benzimidazole)-1,7 & 1,6 bis (4"-tertbutyl) phenoxy peryle.

MALDI and UV/vis characterisation data are shown in FIG. 11 and FIG. 12, respectively.

3,4:9,10-Bis(1',2'-anthroquinone imidazole)-1,7 & 1,6 Dibromoperylenes 3,4:9,10-Bis(1',2'-anthroquinone imidazole)-1,7 & 1,6 dibromoperylenes (Compound 5) were was prepared in the same manner as Compound 2 except 1,2 diamino anthroquinone was used in place of 1,2 diaminobenzene. 250 mg of Compound 1 (0.45 mmol) was reacted with 275 mg of diamino anthroquinone (and 100 mg of $Zn(OAc)_2 \cdot H_2O$ to afford 420 mg of Compound 5, 97% crude yield. The resulting compound was insoluble and used directly to form Compound 6.

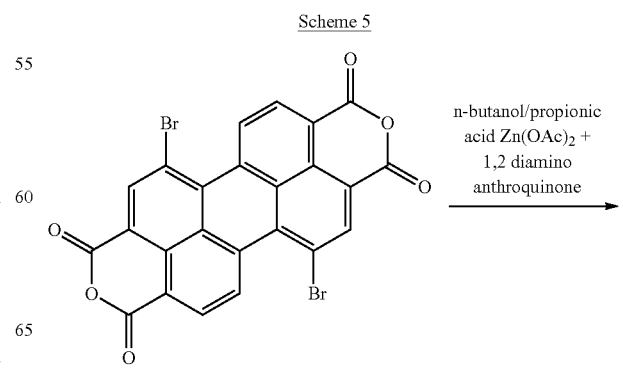

3,4:9,10-Bis(1',2'-anthroquinone imidazole)-1,7 & 1,6 bis (4"-dodecyl) phenoxy Perylenes

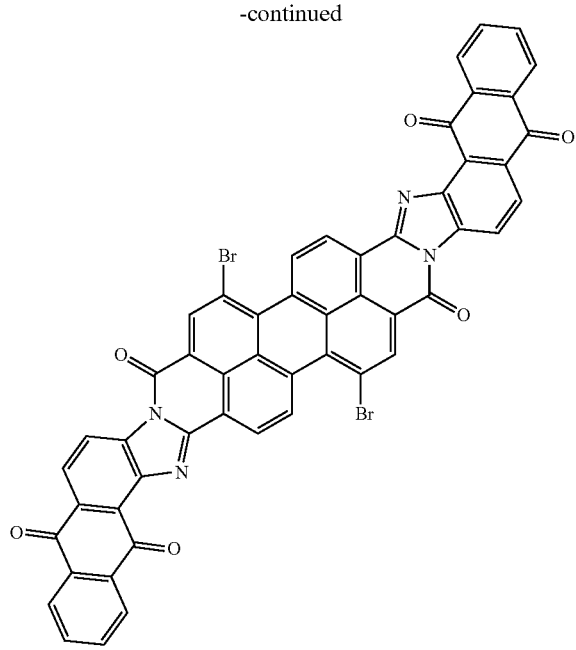

Scheme 5 only shows the anti, trans isomer.

3,4:9,10-Bis(1',2'-anthroquinone imidazole)-1,7 & 1,6 bis (4"-dodecyl) phenoxy perylenes (Compound 6) were synthesised, wherein 56.6 g of 4-dodecyl phenol (mixture of isomers) was poured into a 1 L round bottomed vessel and diluted with 600 mL of DMF. 30 g of Compound 2 (43.2 mmol) was added by funnel along with 30 g of $K_2CO_3$. The mixture was heated to 110° C. under $N_2$ for 6 hours and allowed to cool to room temperature. 600 mL of methanol was added and the mixture was filtered in a 500 mL Buchner funnel. The dark filtrate, composed largely of side products, was discarded. This was followed by another 2×200 mL of fresh methanol washings. The solid cake was then extracted with 1.5 L of boiling, distilled water. Finally, 3×200 mL washings with acetone removed some side materials. The remaining solid was dried under vacuum to afford 39.90 g of product, 88% yield. MS (MALDI) calc. for $H^+$—$C_{88}H_{76}N_4O_8$ 1318.57, found 1318.24 UV/vis in $CHCl_3$, nm (rel int): 621 nm (1.0), 578 nm (0.77), 460 nm (0.20), 336 nm (0.12) Fluorescence max in $CHCl_3$: 654 nm.

Scheme 6

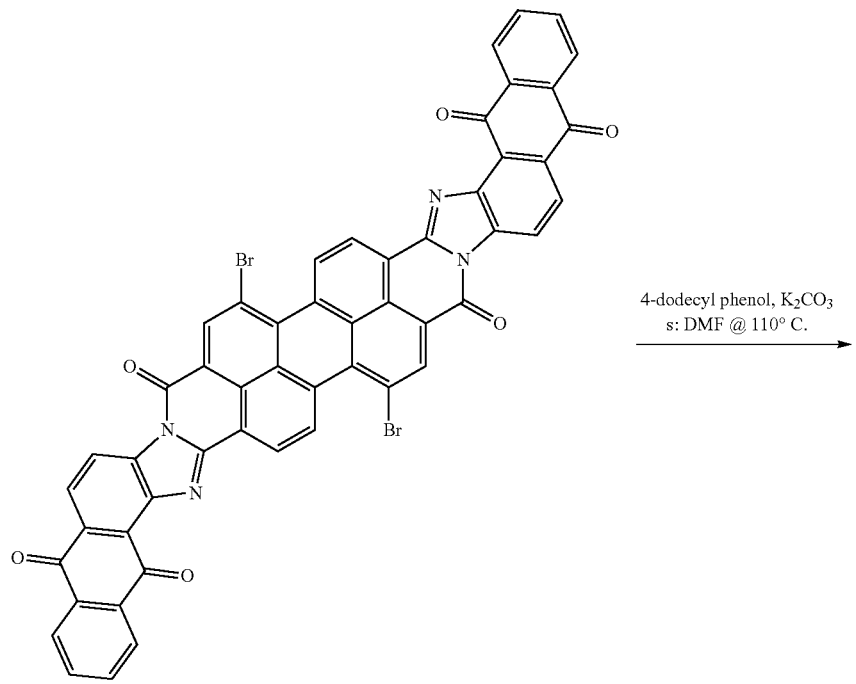

4-dodecyl phenol, $K_2CO_3$
s: DMF @ 110° C.

-continued

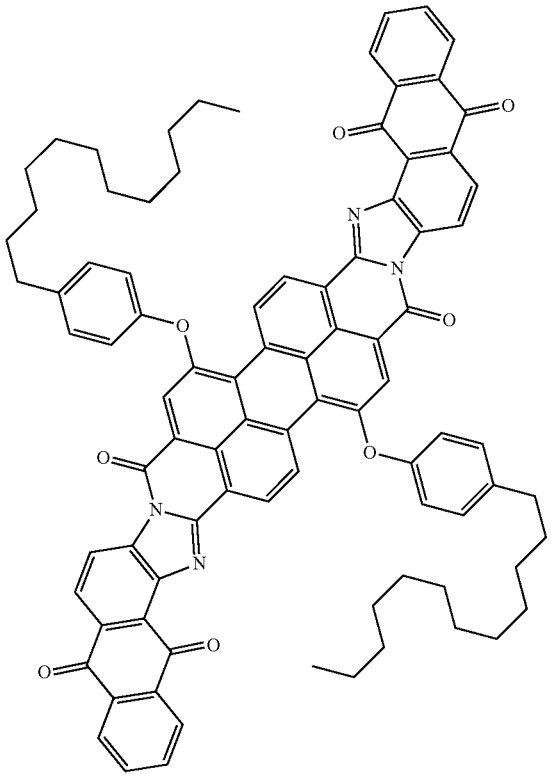

Scheme 6 only shows the anti, trans isomer.

Figure 13:
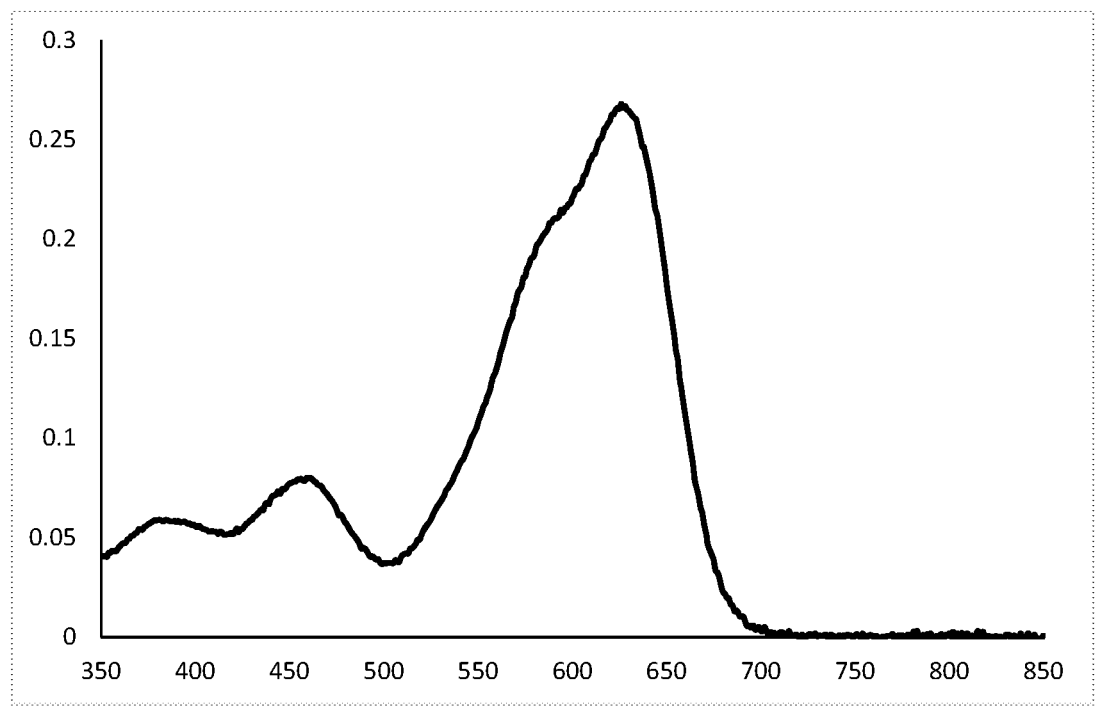
FIG. 13—UV/vis absorbance characterisation data for 3,4:9,10-bis(1',2'-anthroquinone imidazole)-1,7 & 1,6 bis (4"-dodecyl) phenoxy perylenes.
Figure 14:
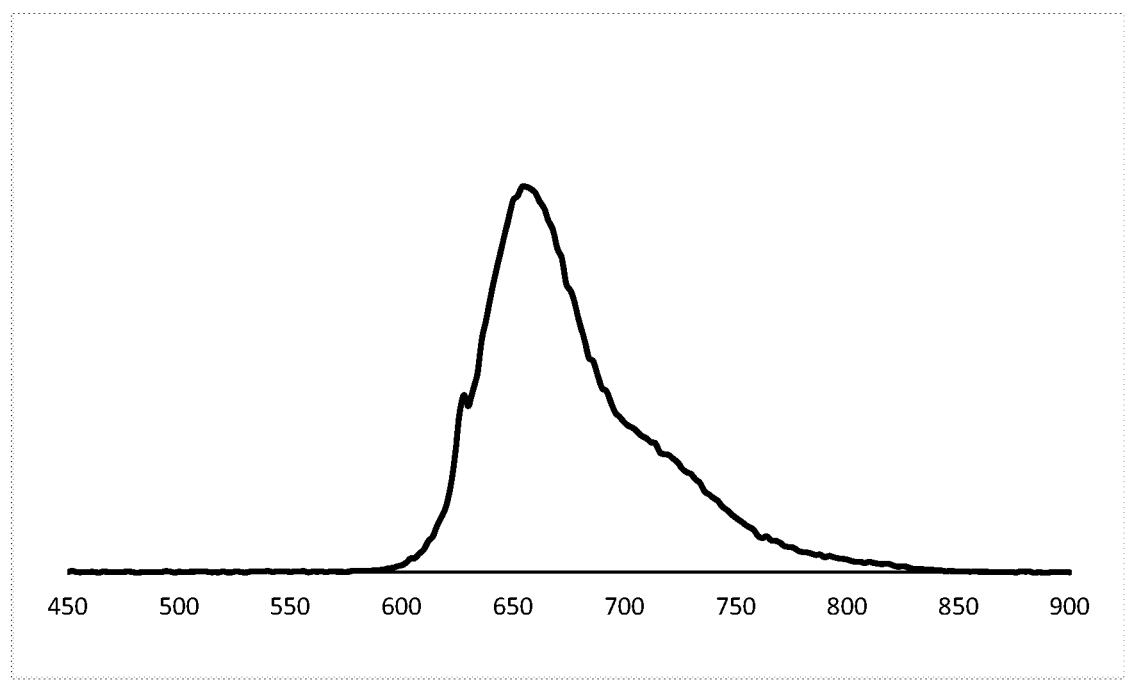
FIG. 14—UV/vis fluorescence characterisation data for 3,4:9,10-bis(1',2'-anthroquinone imidazole)-1,7 & 1,6 bis (4"-dodecyl) phenoxy perylenes.
Figure 15:
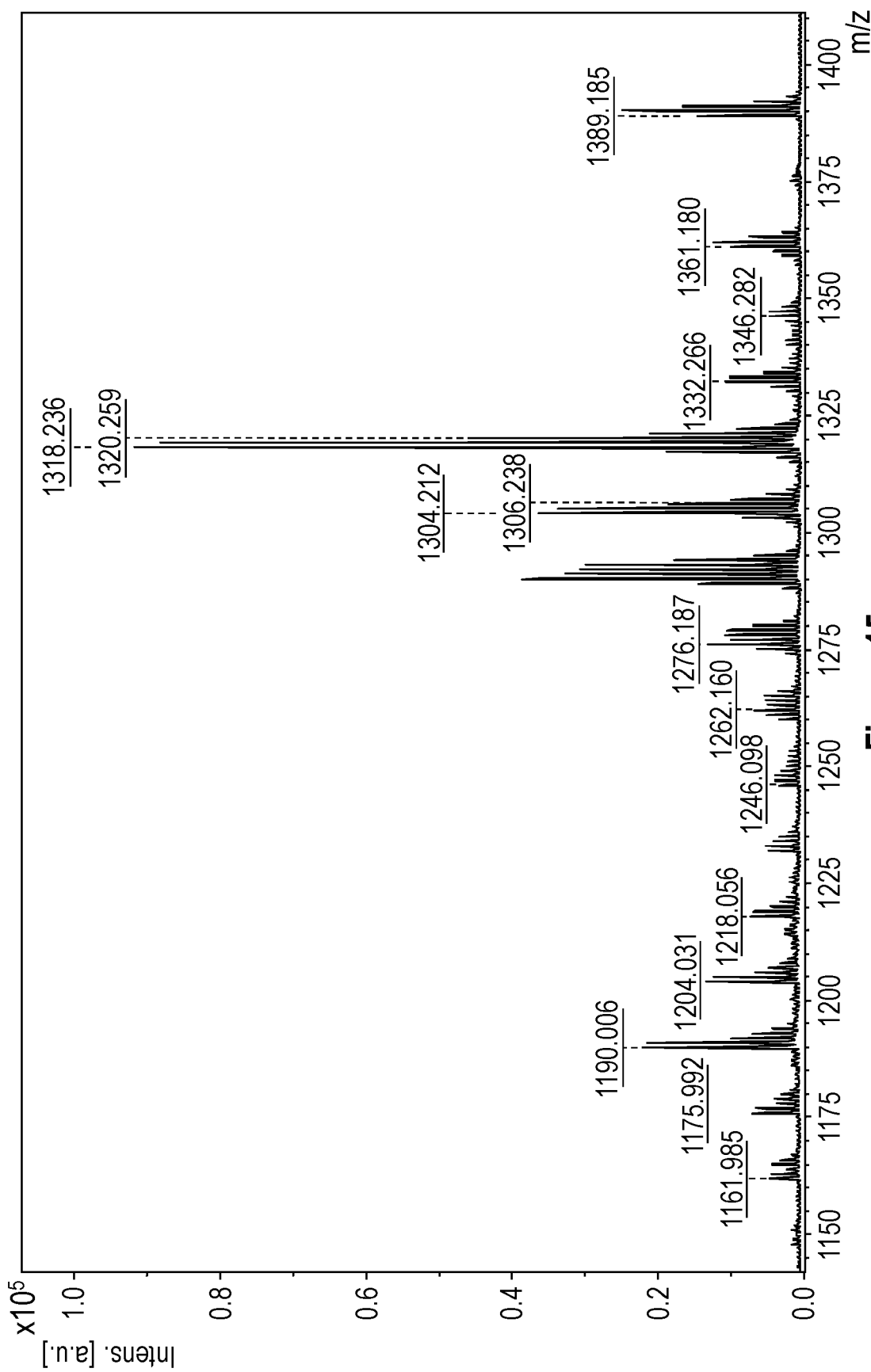
FIG. 15—MALDI TOF MS characterisation data for 3,4:9,10-bis(1',2'-anthroquinone imidazole)-1,7 & 1,6 bis (4"-dodecyl) phenoxy perylenes.

UV/vis absorbance, fluorescence and MALDI characterisation data are shown in FIG. 13, FIG. 14 and Figure, respectively. In FIG. 15 the artefact peak near 630 nm arises from excitation light source in the fluorometer It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A compound of Formula (I):

(I)

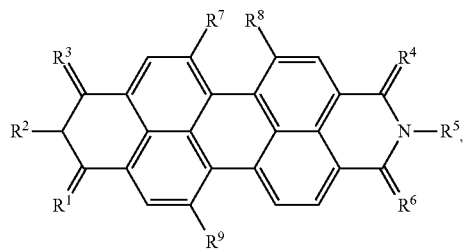

or a salt thereof, wherein:

for $R^1$, $R^2$ and $R^3$ either:

(i) $R^1$ is O, $R^3$ is N, and $R^2$ and $R^3$ are joined by a

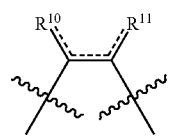

group; or (ii) $R^3$ is O, $R^1$ is N, and $R^1$ and $R^2$ are joined by a

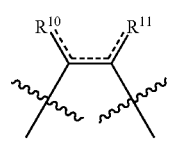

group;
for $R^4$, $R^5$ and $R^6$ either:
(i) $R^4$ is O, $R^6$ is N, and $R^5$ and $R^6$ are joined by a

[structure with $R^{12}$, $R^{13}$]

group; or
(ii) $R^6$ is O, $R^4$ is N, and $R^4$ and $R^5$ are joined by a

[structure with $R^{12}$, $R^{13}$]

group;
$R^{10}$ and $R^{11}$ are joined to form: an optionally substituted monocyclic aromatic ring; or an optionally substituted polycyclic aromatic group;
$R^{12}$ and $R^{13}$ are joined to form: an optionally substituted monocyclic aromatic ring; or an optionally substituted polycyclic aromatic group;
each of $R^7$, $R^8$ and $R^9$ is
independently selected from hydrogen or

[structure with O-phenyl-$(R^{14})_n$]

with the proviso that two of $R^7$, $R^8$ and $R^9$ are

[structure with O-phenyl-$(R^{14})_n$]

and the other is hydrogen
each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene groups, each of which optionally comprises one or more substituents;

===== represents the presence of a single or double bond; and
n is an integer selected from 0, 1, 2, 3, 4 or 5,
wherein when:
a) $R^1$ is O, $R^3$ is N, and $R^2$ and $R^3$ are joined by a

[structure with $R^{10}$, $R^{11}$]

group; and $R^4$ is O, $R^6$ is N, and $R^5$ and $R^6$ are joined by a

[structure with $R^{12}$, $R^{13}$]

group; or
b) $R^3$ is O, $R^1$ is N, and $R^1$ and $R^2$ are joined by a

[structure with $R^{10}$, $R^{11}$]

group; and $R^6$ is O, $R^4$ is N, and $R^4$ and $R^5$ are joined by a

[structure with $R^{12}$, $R^{13}$]

group,
then $R^8$ is H and $R^7$ and $R^9$ are

[structure with O-phenyl-$(R^{14})_n$]

2. The compound of claim 1 of Formula (I-A):

(I-A)

[perylene diimide structure with $R^7$, $R^8$, $R^9$, $R^{10}$, $R^{11}$, $R^{12}$, $R^{13}$]

or a salt thereof, wherein
R$^{10}$ and R$^{11}$ are joined to form: an optionally substituted monocyclic aromatic ring; or an optionally substituted polycyclic aromatic group;
R$^{12}$ and R$^{13}$ are joined to form: an optionally substituted monocyclic aromatic ring; or an optionally substituted polycyclic aromatic group;
R$^8$ is hydrogen;
R$^7$ and R$^9$ are

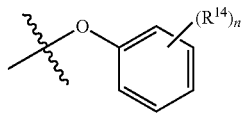

each R$^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, (C$_1$-C$_4$ haloalkoxy)alkyl, (heteroaryl)alkyl, or perylene groups, each of which optionally comprises one or more substituents;
===== represents the presence of a single or double bond; and
n is an integer selected from 0, 1, 2, 3, 4 or 5.

3. The compound of claim 1 of Formula (I-B):

(I-B)

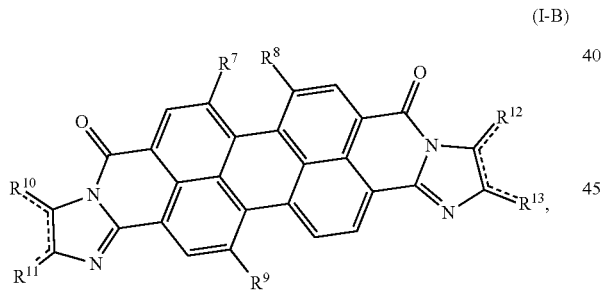

or a salt thereof, wherein
R$^{10}$ and R$^{11}$ are joined to form: an optionally substituted monocyclic aromatic ring; or an optionally substituted polycyclic aromatic group;
R$^{12}$ and R$^{13}$ are joined to form: an optionally substituted monocyclic aromatic ring; or an optionally substituted polycyclic aromatic group;
each of R$^7$, R$^8$ and R$^9$ is
independently selected from hydrogen or

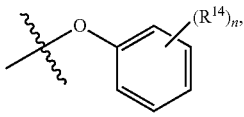

with the proviso that two of R$^7$, R$^8$ and R$^9$ are

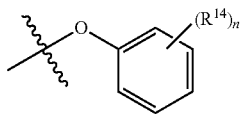

and the other is hydrogen;
each R$^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, (C$_1$-C$_4$ haloalkoxy)alkyl, (heteroaryl)alkyl, or perylene groups, each of which optionally comprises one or more substituents;
===== represents the presence of a single or double bond; and
n is an integer selected from 0, 1, 2, 3, 4 or 5.

4. The compound of claim 1 of Formula (I-C):

(I-C)

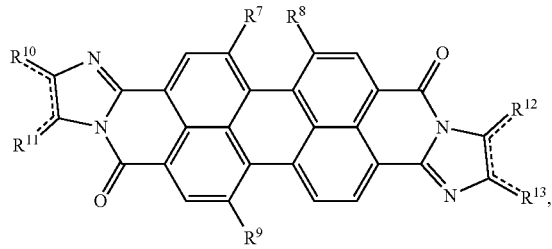

or a salt thereof, wherein:
R$^{10}$ and R$^{11}$ are joined to form: an optionally substituted monocyclic aromatic ring; or an optionally substituted polycyclic aromatic group;
R$^{12}$ and R$^{13}$ are joined to form: an optionally substituted monocyclic aromatic ring; or an optionally substituted polycyclic aromatic group;
R$^8$ is hydrogen;
R$^7$ and R$^9$ are

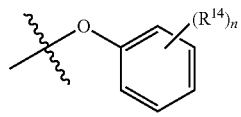

each R$^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene groups, each of which optionally comprises one or more substituents;

===== represents the presence of a single or double bond; and n is an integer selected from 0, 1, 2, 3, 4 or 5.

5. The compound of claim 1 of Formula (I-D):

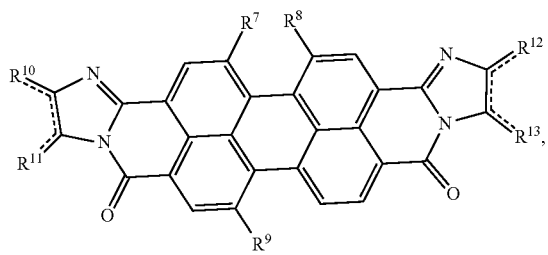

(I-D)

or a salt thereof, wherein:

$R^{10}$ and $R^{11}$ are joined to form: an optionally substituted monocyclic aromatic ring; or an optionally substituted polycyclic aromatic group;

$R^{12}$ and $R^{13}$ are joined to form: an optionally substituted monocyclic aromatic ring; or an optionally substituted polycyclic aromatic group;

each of $R^7$, $R^8$ and $R^9$ is independently selected from hydrogen or

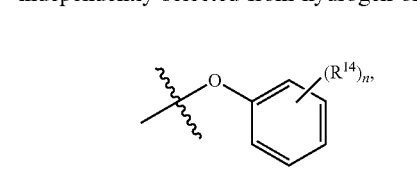

with the proviso that two of $R^7$, $R^8$ and $R^9$ are

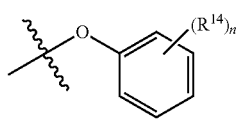

and the other is hydrogen;

each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene groups, each of which optionally comprises one or more substituents;

===== represents the presence of a single or double bond; and n is an integer selected from 0, 1, 2, 3, 4 or 5.

6. The compound according to claim 1, wherein $R^7$ and $R^8$ are

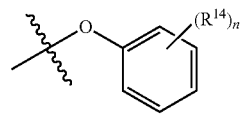

and $R^9$ is hydrogen.

7. The compound according to claim 1, wherein the optionally substituted monocyclic aromatic ring or optionally substituted polycyclic aromatic group is selected from the group consisting of optionally substituted:

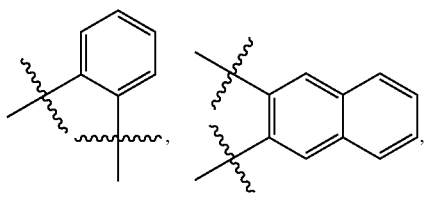

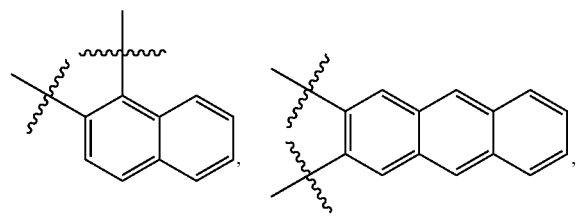

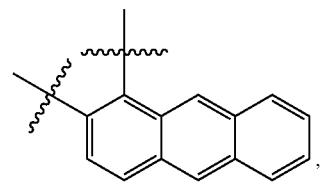

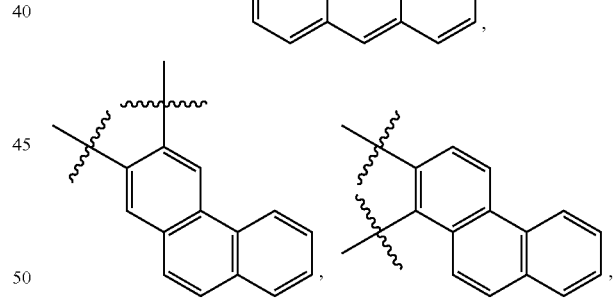

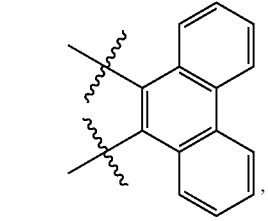

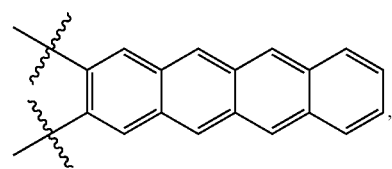

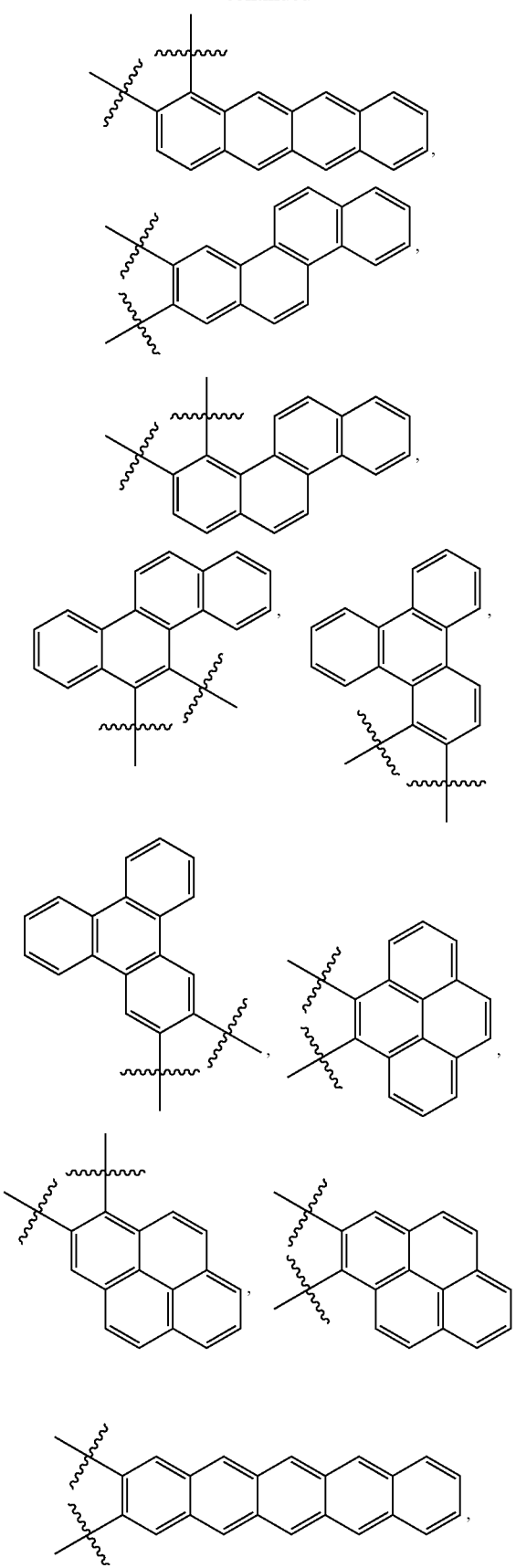
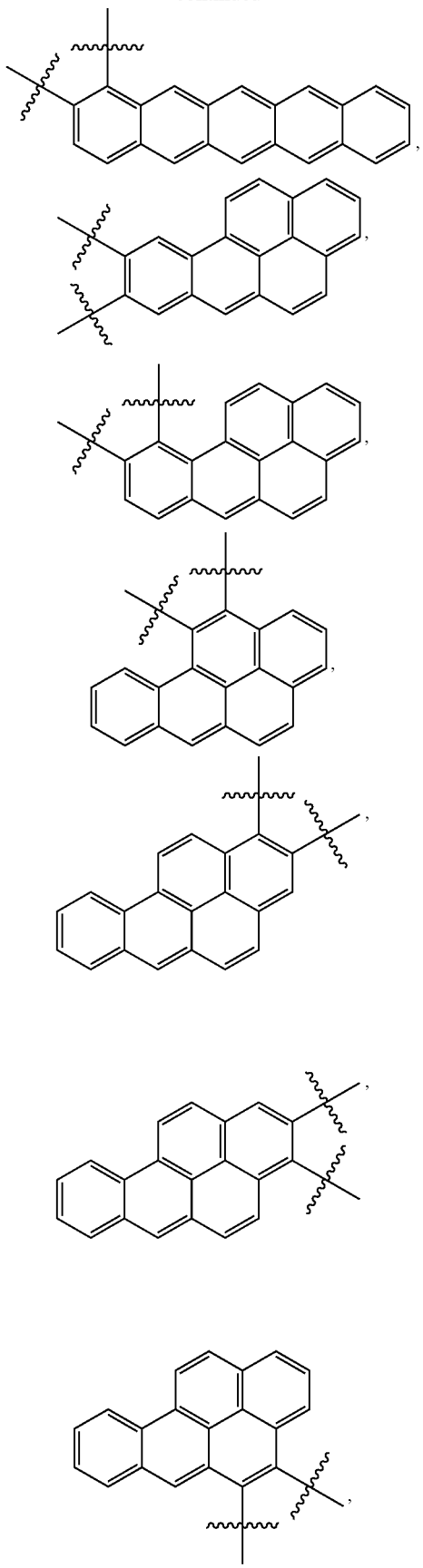

-continued

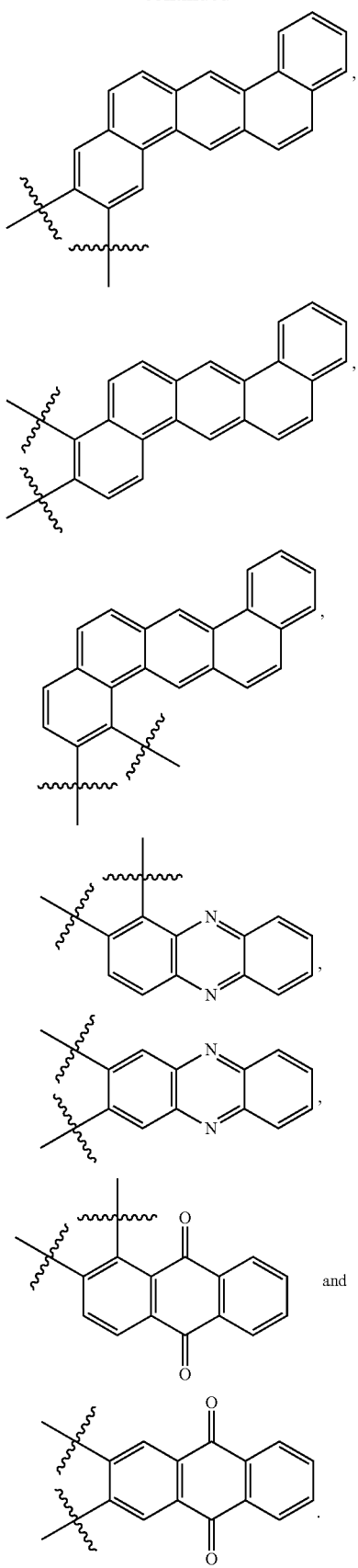

8. The compound according to claim 1, wherein the optionally substituted monocyclic aromatic ring is:

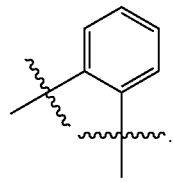 [SMILES: *c1ccccc1*]

9. The compound according to claim 1, wherein $R^{14}$ is an optionally substituted alkyl group or an optionally substituted perylene.

10. The compound according to claim 1, wherein n is 0.

11. The compound according to claim 1, wherein

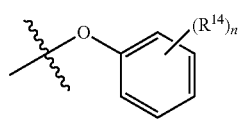

is selected from the group consisting of optionally substituted:

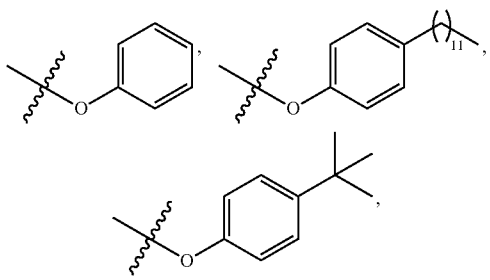

or a mixture thereof.

12. The compound according to claim 1, which meets at least one of the following criteria:

the compound has an absorbance in a range of about 600 nm to about 800 nm in a UV/Vis spectrum; and the compound has a fluorescence maxima in a range of about 625 nm to about 900 nm.

13. A dye composition comprising a compound of Formula (I):

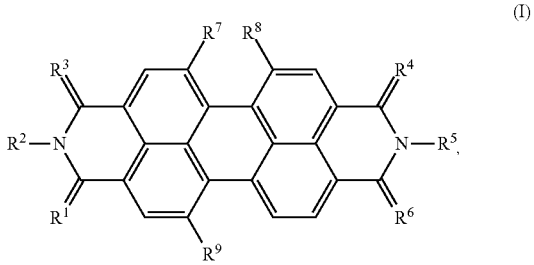

or a salt thereof, wherein:

for $R^1$, $R^2$ and $R^3$ either:

(i) $R^1$ is O, $R^3$ is N, and $R^2$ and $R^3$ are joined by a

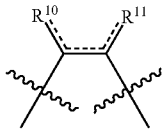

group; or (ii) $R^3$ is O, $R^1$ is N, and $R^1$ and $R^2$ are joined by a

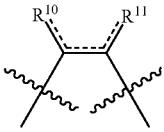

group;

for $R^4$, $R^5$ and $R^6$ either:

(i) $R^4$ is O, $R^6$ is N, and $R^5$ and $R^6$ are joined by a

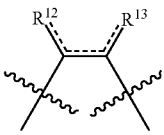

group; or (ii) $R^6$ is O, $R^4$ is N, and $R^4$ and $R^5$ are joined by a

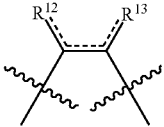

group;

$R^{10}$ and $R^{11}$ are joined to form: an optionally substituted monocyclic aromatic ring; or an optionally substituted polycyclic aromatic group;

$R^{12}$ and $R^{13}$ are joined to form: an optionally substituted monocyclic aromatic ring; or an optionally substituted polycyclic aromatic group;

each of $R^7$, $R^8$ and $R^9$ is independently selected from hydrogen or

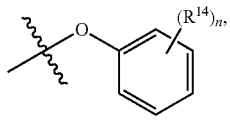

with the proviso that two of $R^7$, $R^8$ and $R^9$ are

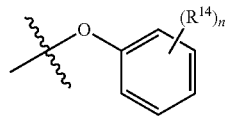

and the other is hydrogen;

each $R^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene groups, each of which optionally comprises one or more substituents;

===== represents the presence of a single or double bond; and n is an integer selected from 0, 1, 2, 3, 4 or 5;

wherein when:

a) $R^1$ is O, $R^3$ is N, and $R^2$ and $R^3$ are joined by a

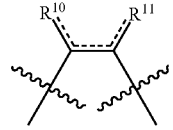

group; and $R^4$ is O, $R^6$ is N, and $R^5$ and $R^6$ are joined by a

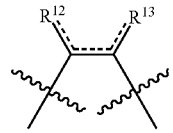

group; or b) $R^3$ is O, $R^1$ is N, and $R^1$ and $R^2$ are joined by a

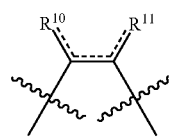

group; and $R^6$ is O, $R^4$ is N, and $R^4$ and $R^5$ are joined by a

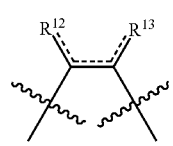

group, then $R^8$ is H and $R^7$ and $R^9$ are
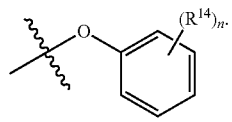
14. The dye composition according to claim 13, wherein the optionally substituted monocyclic aromatic ring or optionally substituted polycyclic aromatic group is selected from the group consisting of optionally substituted:
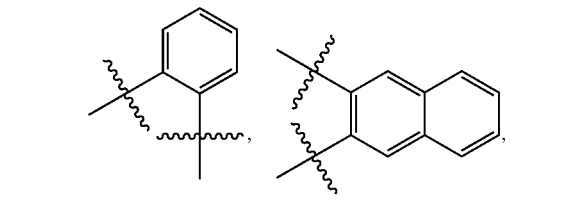
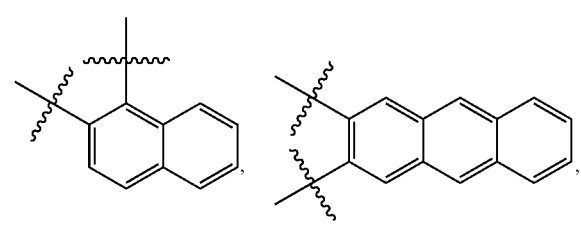
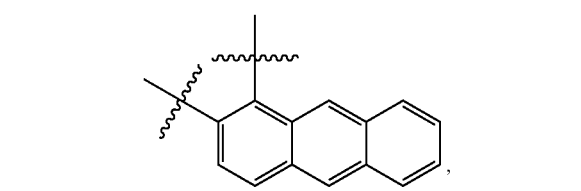
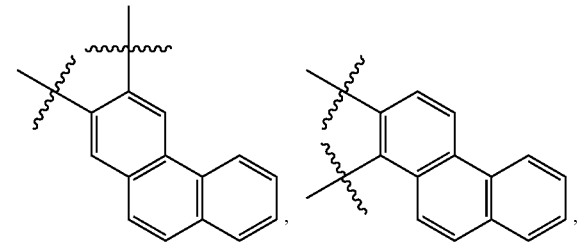
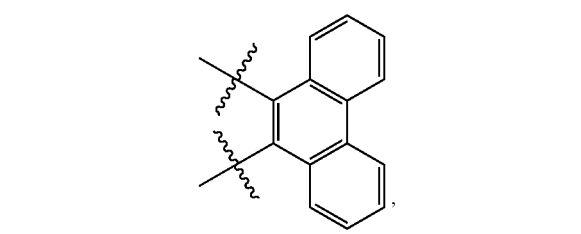
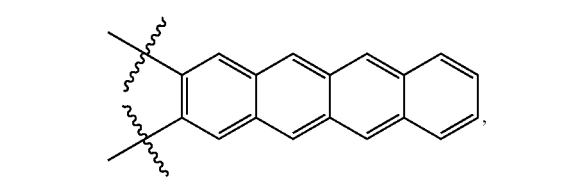
-continued
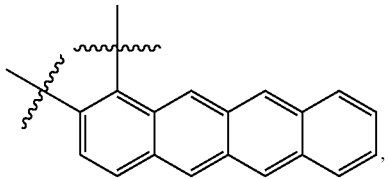
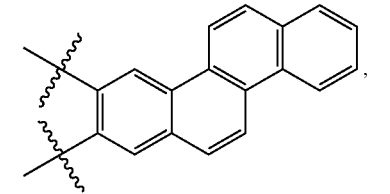
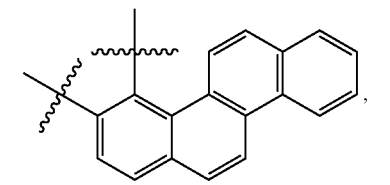
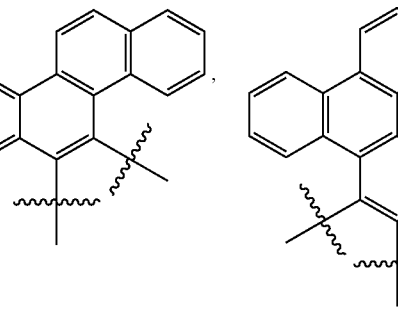
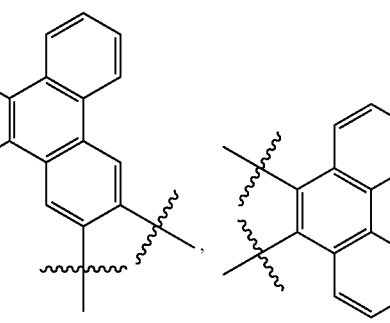
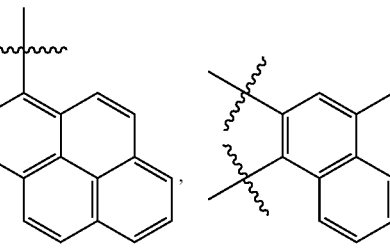
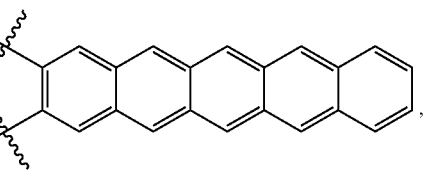

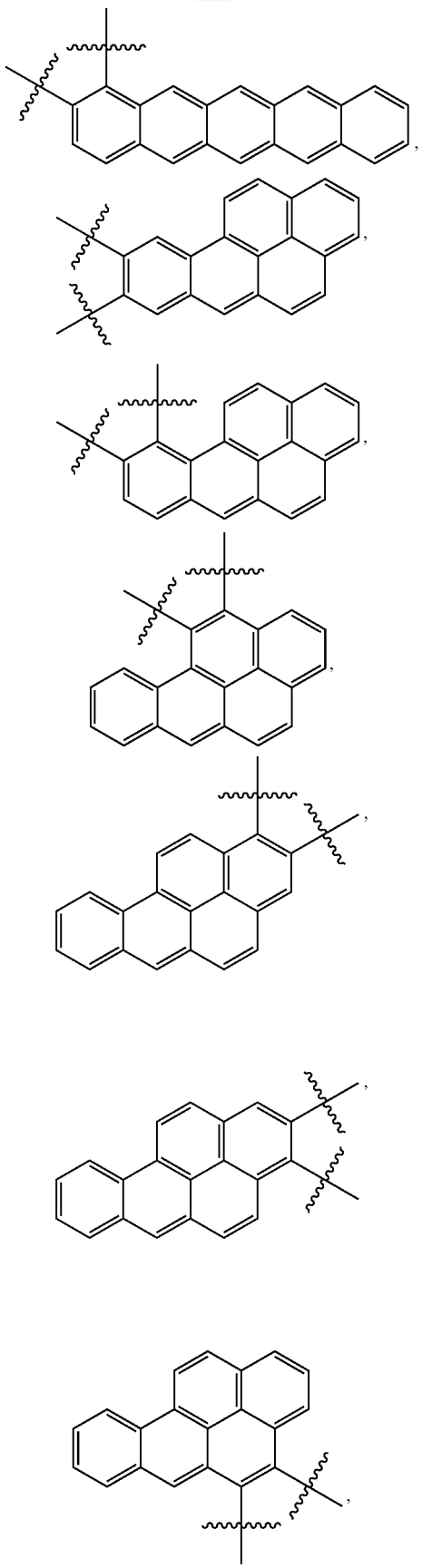
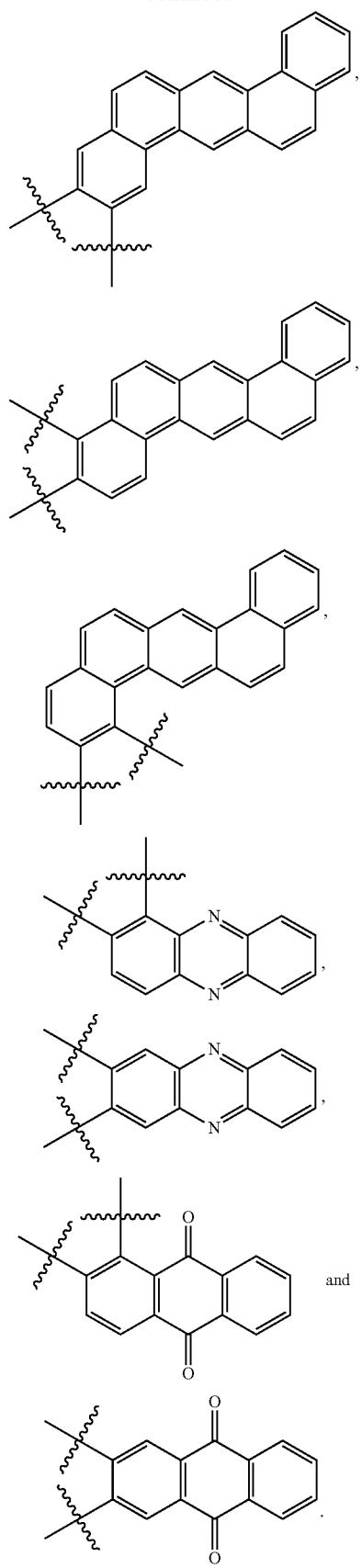
and

15. The dye composition according to claim 13, wherein:
R$^{14}$ is an optionally substituted alkyl group or an optionally substituted perylene; or

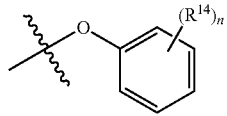

is selected from the group consisting of optionally substituted:

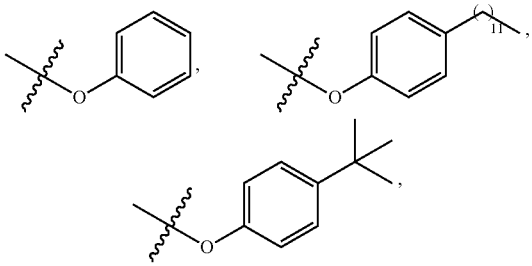

or a mixture thereof.

16. A method of synthesizing a compound of Formula (I):

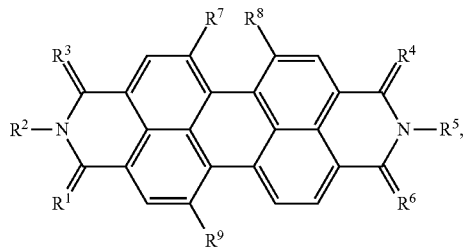 (I)

or a salt thereof, wherein:

for R$^1$, R$^2$ and R$^3$ either:
(i) R$^1$ is O, R$^3$ is N, and R$^2$ and R$^3$ are joined by a

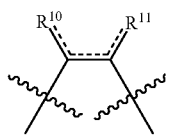

group; or
(ii) R$^3$ is O, R$^1$ is N, and R$^1$ and R$^2$ are joined by a

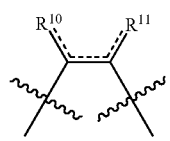

group;

for R$^4$, R$^5$ and R$^6$ either:
(i) R$^4$ is O, R$^6$ is N, and R$^5$ and R$^6$ are joined by a

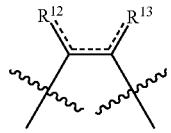

group; or
(ii) R$^6$ is O, R$^4$ is N, and R$^4$ and R$^5$ are joined by a

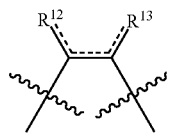

group;

R$^{10}$ and R$^{11}$ are joined to form: an optionally substituted monocyclic aromatic ring; or an optionally substituted polycyclic aromatic group;

R$^{12}$ and R$^{13}$ are joined to form: an optionally substituted monocyclic aromatic ring; or an optionally substituted polycyclic aromatic group;

each of R$^7$, R$^8$ and R$^9$ is
independently selected from hydrogen or

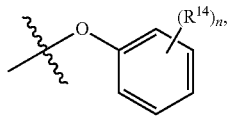

with the proviso that two of R$^7$, R$^8$ and R$^9$ are

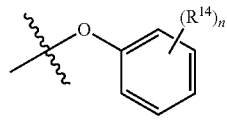

and the other is hydrogen;

each R$^{14}$ is independently selected from: alkyl, alkenyl, alkynyl, halogen, nitro, cyano, hydroxy, sulfonic, thiol, ether, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, carboxy, carboxyalkyl, cycloalkyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, (heteroaryl)alkyl, or perylene groups, each of which optionally comprises one or more substituents;

===== represents the presence of a single or double bond; and n is an integer selected from 0, 1, 2, 3, 4 or 5, wherein when:

a) $R^1$ is O, $R^3$ is N, and $R^2$ and $R^3$ are joined by a

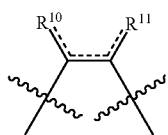

group; and $R^4$ is O, $R^6$ is N, and $R^5$ and $R^6$ are joined by a

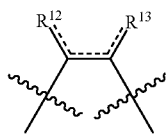

group; or b) $R^3$ is O, $R^1$ is N, and $R^1$ and $R^2$ are joined by a

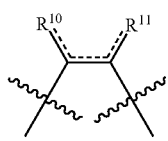

group; and $R^6$ is O, $R^4$ is N, and $R^4$ and $R^5$ are joined by a

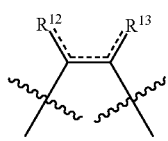

group, then $R^8$ is H and $R^7$ and $R^9$ are

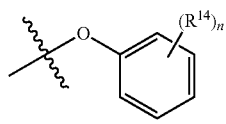

the method comprising the step of contacting a compound of Formula (II):

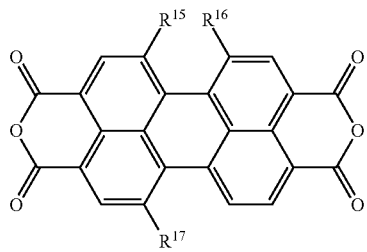

Formula (II)

wherein each of $R^{15}$, $R^{16}$ and $R^{17}$ is independently selected from hydrogen, bromine or chlorine, with the proviso that two of $R^{15}$, $R^{16}$ and $R^{17}$ are either bromine or chlorine, and the other is hydrogen, with a compound of Formula (III):

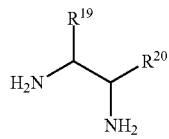

Formula (III)

wherein $R^{19}$ and $R^{20}$: are joined to form an optionally substituted monocyclic aromatic ring; or are joined to form an optionally substituted polycyclic aromatic group.

17. The method according to claim 16, wherein the compound of Formula (III) is selected from the group consisting of optionally substituted:

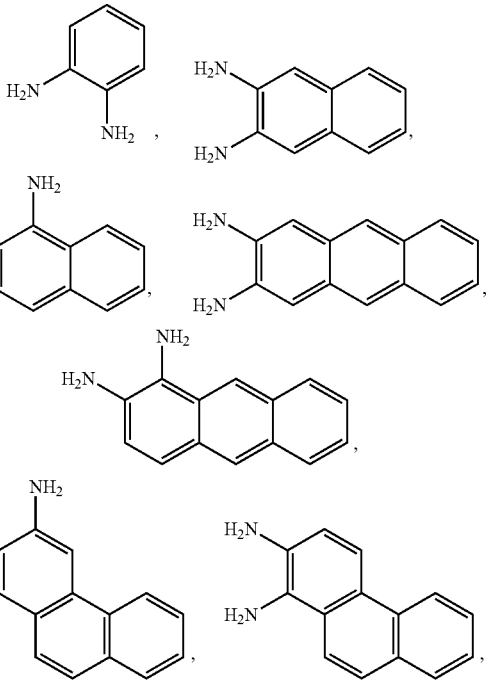

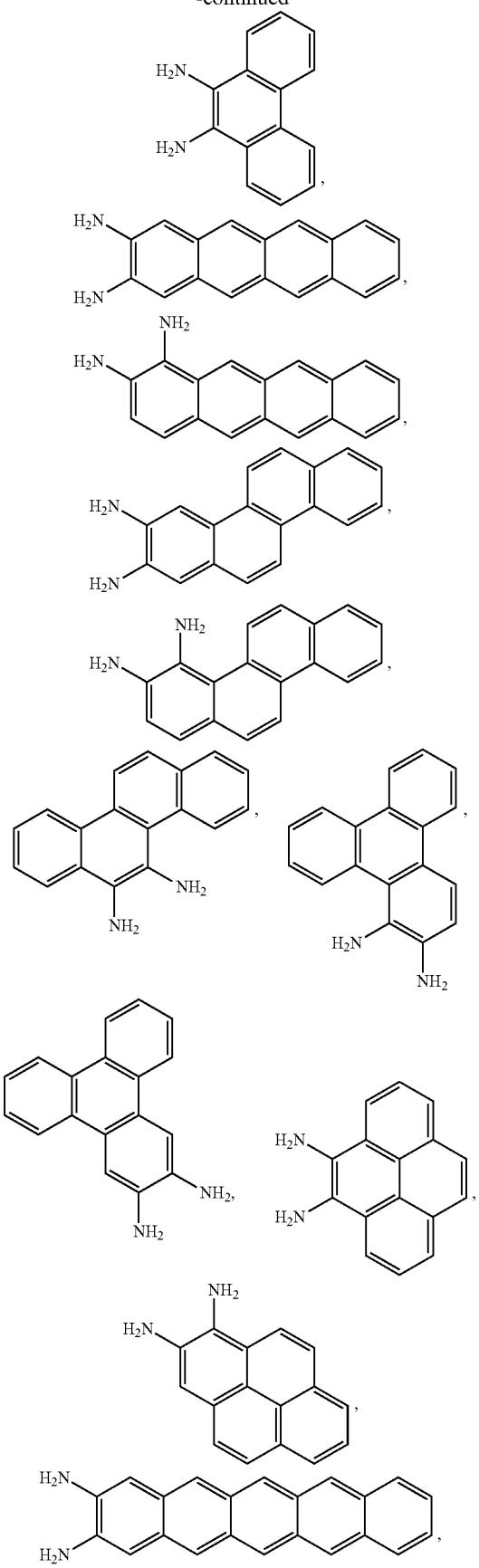
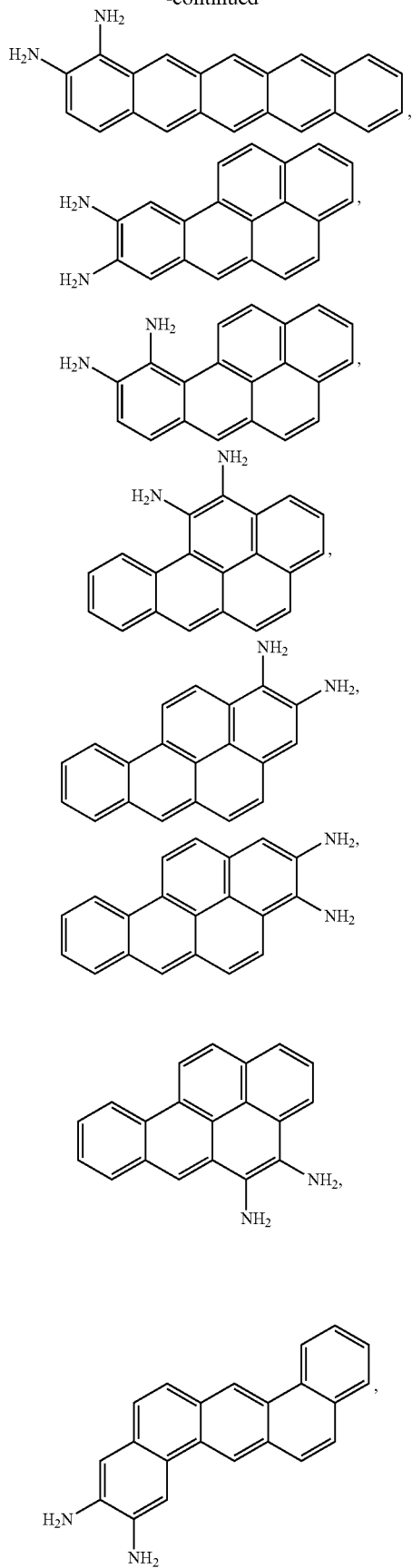

-continued
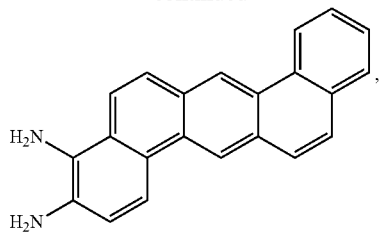
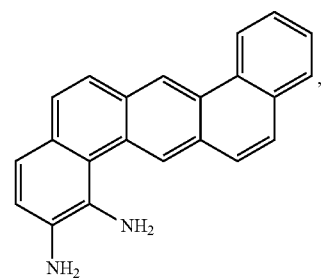
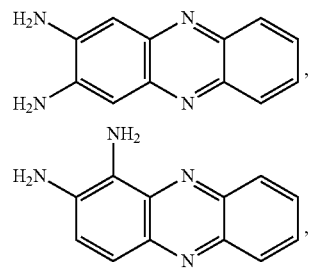
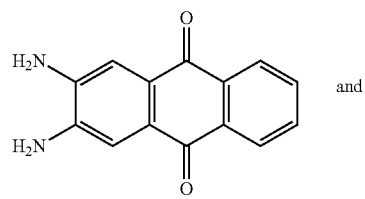
and
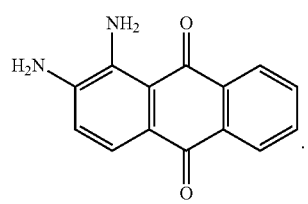
18. The compound according to claim 1, wherein $R^8$ and $R^9$ are
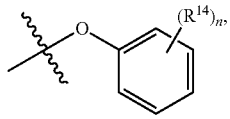
and $R^7$ is hydrogen.
19. The dye composition according to claim 13, wherein either:
   $R^7$ and $R^8$ are
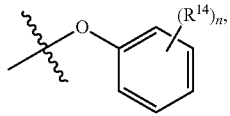
and $R^9$ is hydrogen; or
   $R^8$ and $R^9$ are
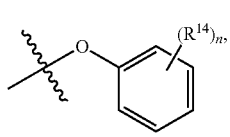
and $R^7$ is hydrogen.
20. The method according to claim 16, wherein either:
   $R^7$ and $R^8$ are
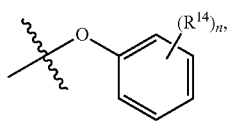
and $R^9$ is hydrogen; or
   $R^8$ and $R^9$ are
and $R^7$ is hydrogen.
* * * * *

UNITED STATES PATENT AND TRADEMARK OFFICE
CERTIFICATE OF CORRECTION

PATENT NO. : 10,995,217 B2
APPLICATION NO. : 16/637024
DATED : May 4, 2021
INVENTOR(S) : Alexander Falber Page 1 of 1

It is certified that error appears in the above-identified patent and that said Letters Patent is hereby corrected as shown below:

In the Claims

Claim 1, Column 75, Lines 56-65, should read:

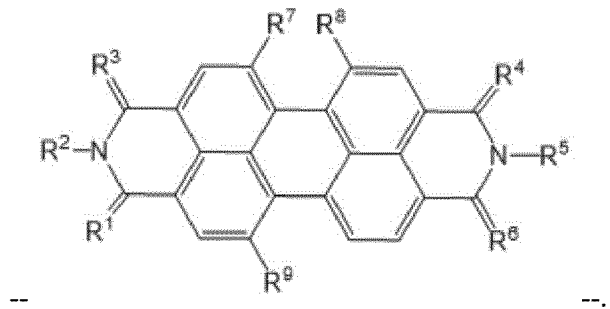

--                  --.

Signed and Sealed this
Thirty-first Day of August, 2021

Drew Hirshfeld
*Performing the Functions and Duties of the
Under Secretary of Commerce for Intellectual Property and
Director of the United States Patent and Trademark Office*